US008989348B2

(12) United States Patent
Cox

(10) Patent No.: US 8,989,348 B2
(45) Date of Patent: Mar. 24, 2015

(54) MULTI-LINEAR X-RAY SCANNING SYSTEMS AND METHODS FOR X-RAY SCANNING

(71) Applicant: Visuum, LLC, Gainesville, FL (US)

(72) Inventor: John D. Cox, Gainesville, FL (US)

(73) Assignee: Visuum, LLC, Gainesville, FL (US)

( * ) Notice: Subject to any disclaimer, the term of this patent is extended or adjusted under 35 U.S.C. 154(b) by 213 days.

(21) Appl. No.: 13/761,821

(22) Filed: Feb. 7, 2013

(65) Prior Publication Data

US 2013/0202087 A1   Aug. 8, 2013

Related U.S. Application Data

(63) Continuation-in-part of application No. 13/679,695, filed on Nov. 16, 2012.

(60) Provisional application No. 61/596,487, filed on Feb. 8, 2012, provisional application No. 61/718,491, filed on Oct. 25, 2012.

(51) Int. Cl.
   *G01N 23/04* (2006.01)
(52) U.S. Cl.
   CPC ........ *G01N 23/04* (2013.01); *G01N 2223/5015* (2013.01)
   USPC .............................. 378/62; 378/146; 378/149
(58) Field of Classification Search
   CPC ........... G01N 23/04; G01N 2223/5015; A61B 6/032; A61B 6/06; G21K 1/04; G21K 1/025; G21K 1/02
   USPC ........................... 378/62, 98.8, 146, 147, 149
   See application file for complete search history.

(56) References Cited

U.S. PATENT DOCUMENTS

| | | | |
|---|---|---|---|
| 5,644,614 A | 7/1997 | Toth | |
| 7,397,892 B2 | 7/2008 | Linev | |
| 7,519,160 B2 | 4/2009 | Vermeulen | |
| 7,873,142 B2 | 1/2011 | Beets | |
| 8,073,099 B2 | 12/2011 | Niu | |
| 2007/0223653 A1* | 9/2007 | Ullberg et al. | 378/62 |
| 2009/0274265 A1 | 11/2009 | Koehler | |
| 2011/0026668 A1 | 2/2011 | Wu | |
| 2011/0033024 A1 | 2/2011 | Dafni | |
| 2011/0280363 A1 | 11/2011 | Zou | |

OTHER PUBLICATIONS

International Search Report of PCT/US13/25264 dated Apr. 22, 2013.
Specification of EB8816 Series, Apr. 2010, Rev. 1.3, 2010 X-Scan Imaging Corp.
Specification of X-ray Line Scan Camera C9750, 2010 Hamamatsu Photonics K.K.
International Search Report of PCT/US12/65828 dated Feb. 7, 2013.

* cited by examiner

*Primary Examiner* — Courtney Thomas
(74) *Attorney, Agent, or Firm* — Mayback & Hoffman, P.A.; Gregory L. Mayback

(57) ABSTRACT

An x-ray scanner includes an x-ray source producing a fan of x-rays, an x-ray detector array, a collimator between the source and array, fixed to the source, and defining one or more slits collimating the x-ray fan into a linear x-ray beam. The array is spaced from the source such that a linear extent of the linear x-ray beam is no greater than a detector dimension of the array. An x-ray processing unit processes detection of the linear x-ray beam by the array. A processor-controlled motor moves the x-ray source about a source movement axis to pan the linear x-ray beam and create an x-ray emission cone and moves the array correspondingly with the source. The x-ray processing unit form an x-ray scanned image of an object disposed between the collimator and the array within the x-ray emission cone when the linear x-ray beam is panned across the object.

18 Claims, 64 Drawing Sheets

Plan View

Elevation View

Plan View

Elevation View

Plan View

Elevation View

MULTI-LINEAR X-RAY SCANNING SYSTEMS AND METHODS FOR X-RAY SCANNING

CROSS-REFERENCE TO RELATED APPLICATIONS

This application is:
claims priority to U.S. Provisional Application Ser. No. 61/596,487, filed on Feb. 8, 2012;
claims priority to U.S. Provisional Application Ser. No. 61/718,491, filed on Oct. 25, 2012; and
is a continuation-in-part of U.S. patent application Ser. No. 13/679,695, filed Nov. 16, 2012 (which claims priority to U.S. Provisional Application Ser. No. 61/561,613 filed on Nov. 18, 2011),
the entire disclosures of which are hereby incorporated herein by reference in their entireties.

STATEMENT REGARDING FEDERALLY SPONSORED RESEARCH OR DEVELOPMENT

Not Applicable

FIELD OF THE INVENTION

This invention relates to x-ray imaging systems and methods for x-ray scanning and, particularly, to x-ray imaging systems and methods that use a scanning x-ray detector.

BACKGROUND OF THE INVENTION

Transmission x-ray scanners used for personnel screening already exist in the market and are used in high-security areas where access is restricted from the general public, such as prisons, diamond and gold mines, and other places where small, high-value or dangerous items can be smuggled into or out from a secure area. One such system is described in U.S. Pat. No. 7,397,892 B2 to Linev, which issued on Jul. 8, 2008, and is incorporated herein in its entirety. Linev teaches the use of an x-ray source that produces a single, fan-shaped x-ray beam that is collimated to produce a vertical beam of x-rays that is further collimated down to a very narrow slit. These collimated x-rays illuminate a single linear array of photo diodes coated with a scintillating phosphor. The person to be scanned stands on a motor-driven platform that moves the person slowly in between the source and the diode detector array exposing their entire body to the x-ray beam, thereby producing an x-ray image of their entire body. The x-ray image then reveals any objects they may have ingested, hidden in their clothing, or inserted in a body cavity.

The system taught by Linev, while effective because it can reveal the hidden items described above, suffers from a number of limitations. One of the primary limitations that the preferred embodiment of the Linev system suffers from is the inability to scan someone who has difficulty standing or is in a wheelchair. The platform (described in Linev as a walk-gate floor or movable door that is moving at constant speed) that is used to move the person being screened across the x-ray beam is small and difficult to access. It would, then, be a simple matter for a person to circumvent the scanner by claiming to need crutches, a walker, or a wheelchair. The scanning speed of the platform is necessarily slow to prevent the person standing on the platform from falling down or being injured. The slow scanning speed reduces throughput of the system and, thereby, the rate at which people can be scanned. Another limitation of this system is that x-ray radiation scattered from the person being scanned exposes anyone in the vicinity of the system to harmful radiation. This is because the system taught by Linev does not fully enclose and shield the walk-gate area. To mitigate this problem, a large exclusion area around the system must be established. This exclusion area greatly increases the amount of space required and increases the cost to install and operate the system. Any rooms adjacent to or in the floors above or below the system would also be similarly affected by this scattered radiation.

Yet another disadvantage of the system taught by Linev is a lack of control of the amount of radiation dose to which the person being scanned is exposed. The Linev system teaches the use of a fixed collimator and a detector positioning system. The exposure dose to the person being scanned is greatly affected by the accuracy in which the x-ray beam covers the detector array. If the width of the collimated fan beam of the x-ray source is larger than the width of the detector array, then x-rays that do not contribute to the image being formed are exposing the person being scanned, causing excess and unwarranted x-ray exposure. Linev also does not teach the use of varying the x-ray beam technique to optimize exposure parameters for each person being scanned. An x-ray beam technique refers to the x-ray energy (kVp), the integrated intensity (mAs), and the filtration used to acquire the image. If these x-ray exposure parameters are not adjusted to the specific body mass and anatomical region being scanned, then the exposure used to acquire the image is not optimal and, consequently, the dose used to acquire the image is not minimized. This could result in over-exposure or require a repeat exposure if the parameters are inadequate for an acceptable image (underexposure).

Yet another disadvantage of the system taught by Linev is the inability to create different configurations of the system that could provide flexibility in the installation and use of the system in different facilities. There are places, for example, such as office buildings, hotels, and private residences where the need for security exists but the physical presence of x-ray systems and equipment creates problems with available space and a desire to obscure or hide the security apparatus from view.

X-ray scanning systems already exist in the market and are used for whole-body imaging in applications like triage in trauma centers and emergency rooms in hospitals. One such system is described in U.S. Pat. No. 7,519,160 B2 to Vermeulen, issued on Apr. 14, 2009, which is incorporated herein in its entirety. Vermeulen teaches the use of a linear scanning x-ray apparatus that generates a collimated fan beam that is moved together with a detector relative to an object to generate a composite x-ray image of the subject. The x-ray generator and detector array is mounted on a C-arm that allows the generator and detector array to rotate about the patient being scanned, thereby obtaining a variety of views including chest and cross-table laterals.

The system of Vermeulen teaches an image acquisition mode where the x-ray source and detector array move together along an axis (the scanning direction) and a collimator creates a transverse fan beam of x-rays that illuminate a linear array of detectors. The divergent fan beam used by the linear scanning apparatus results in distortion of the image in a direction transverse to the scanning direction. In order to deal with the problem, the technique of x-ray computed tomography (CT) is used to correct for the distortion. This correction method is the subject of U.S. Pat. No. 7,873,142 B2 to Beets, issued on Jan. 18, 2011, which is incorporated herein in its entirety. Because the C-arm assembly holding the x-ray source and detector array has to be moved during a scan, the scanning speed must be kept at a slow rate to avoid significant hazards from collisions that could occur if the C-arm was moved at a high speed. Accordingly, the system requires up to 13 seconds to perform a whole-body scan of a patient.

Medical x-ray imaging systems require significantly higher spatial resolution than the x-ray imaging systems used in security applications. Accordingly, a significantly higher radiation dose is required to obtain a medical diagnostic image compared with an image obtained for security screening purposes. The spatial resolution used in security screening applications is about 0.5 line-pairs per millimeter (lp/mm) with an exposure dose of about 0.25 microSieverts. Medical diagnostic images require a spatial resolution of 2-4 lp/mm and require a dose of about 20 microSieverts. In order to minimize the exposure dose for medical applications when scanning systems are used, a technique called time delay and integration (TDI) is used. Special detector arrays that are designed for TDI image acquisition are currently available in the market today. One type is based on frame-transfer Charge Coupled Device (CCD) integrated circuit camera technology. Another type is based on a photodiode-CMOS integrated circuit TDI camera technology.

A linear array has a single row of detector elements that can be used in a scanning system to acquire an image by moving the source in the transverse direction of the linear array. In contrast, a TDI sensor array has several rows of detectors that are lined up in the direction of the scanning source. The image acquired by the TDI sensor is clocked out at a speed equal to the scanning speed in the opposite direction of the scanner. The result of this process is that the image signal acquired from each row of detectors is passed on to the next row of detectors where it is added to the next acquisition by superposition. If the clocking speed and scanning speed is equal and opposite in direction, the image signal is increased for each row of detectors. A TDI sensor with 128 rows will acquire an image with a signal intensity that is 128-times higher than a single linear array can produce. Alternatively, the scanner can scan at a higher velocity and acquire an image with less exposure dose. TDI image acquisition is taught by Vermeulen.

SUMMARY OF THE INVENTION

The multi-linear x-ray scanner and methods for scanning described herein overcome certain limitations of existing transmission x-ray scanners by using a novel design that permits different configurations to accommodate the user's individual needs. The multi-linear x-ray scanner contains no external moving parts that require secure mounting or that restrict the movement of people coming in and out of the scanner. As a result, the multi-linear x-ray scanner offers distinct advantages in terms of work flow, security options, and aesthetics.

The multi-linear x-ray scanner can be constructed out of two or three separate cabinet features: a generator cabinet; an imaging cabinet; and an optional scanning cabinet or booth. The scanning booth can completely surround (and, if necessary, by adding a ceiling feature, even enclose) the generator and imaging cabinets, or the system can have an open configuration without any enclosure. In other words, the scanning booth can operate as a "closed" system (which, for example, uses a wall, door and/or curtain type of shielding to completely surround the scanning subject) or a "partially-closed" system (which, alternatively for example, uses walls, partitions, or curtains to partially enclose the scanning subject). Both of these configurations thus provide physical shielding for the scattered x-ray radiation emitting from the person during the scan (more commonly known as radiation scatter) to protect others in the immediate vicinity from radiation scatter.

In an entirely open system configuration, the generator and imaging cabinets are not surrounded by any shielding; rather, an exclusion or buffer zone surrounding the system can be used to protect others in the immediate vicinity from radiation scatter.

In another alternative embodiment, the generator cabinet and imaging cabinet can be placed within or behind walls of a room or hallway to hide them from view. To place such a cabinet/cabinets behind a wall/walls, the walls would need x-ray translucent panels to allow the x-rays to penetrate through the walls and/or floor.

The present invention overcomes the limitations of existing transmission x-ray scanners used for medical applications and produces a system and method that is less expensive and does not require image processing to correct for image distortions caused by an x-ray scanner that uses a moving source. The present invention also speeds up the scanning process so that a whole-body scan of a patient can be accomplished in less than one second.

In one embodiment, in order to eliminate the distortion caused by a moving source, it is necessary to fix the position of the x-ray source during image acquisition. In the present invention, the x-ray source is stationary and the collimator and detector array are moved. In order to increase the rate at which the person can be scanned, a plurality of detector arrays are employed. For example, if two horizontal arrays (spaced apart by half the total distance to be scanned) are used, then the distance over which the scanner needs to travel is only half of the length of the person, thereby increasing the speed at which a full-body scan can be accomplished. Accordingly, the collimator used to expose two such arrays has two separate slit apertures. The multi-slit collimator and detector arrays move in synchronicity with each other to ensure that the collimated horizontal x-ray beams accurately track the motion of the arrays during a scan. The motion control for the collimator and detector arrays is, in an exemplary embodiment, accomplished with a microprocessor-controlled set of motors and encoders to move and monitor the position of the collimator and detector array assembly during scanning.

The scanning speed of the detectors can be significantly increased compared with the system taught by Vermuelen because the x-ray source does not move and the detectors are mounted on rails inside the patient table. This configuration prevents anyone from coming in contact with the moving components of the system and, as a result, they can move at much higher speeds. In order to accommodate a higher scanning speed, the intensity of the x-rays produced by the source is increased proportionally to the increased scanning speed. Because the total scanning time is reduced proportionally to the speed, the total exposure dose to the patient does not change.

The geometry and quality of the x-ray beam produced by the x-ray source according to the present invention is tightly controlled to optimize image quality and minimize patient radiation exposure dose by ensuring that the dimensions of the x-ray beams are confined to the dimensions of the detector arrays during a scan and that the technique factors used to acquire the image are optimal for the anatomical region and patient body mass. The x-ray tube is housed in a lead-lined housing containing an aperture that confines the emitted x-ray beam to the height and width of the imaging area defined by the x-ray detector array and scanning assembly. A set of x-ray filters is also enclosed in the x-ray housing placed just in front of the x-ray tube. The filter set contains one or more aluminum and copper filters that attenuate and modify the x-ray spectra emitted by the source. The x-ray beam then passes through a dosimeter where the exposure dose is measured before the beam enters the collimator assembly. The x-ray dose measured by the dosimeter is then used to calculate the exposure dose incident on the person being scanned through an algorithm commonly used in medical radiographic equipment.

The collimator assembly includes a plurality of horizontal slits that collimate the incident x-ray beam into a plurality of parallel horizontal x-ray beams that move synchronously with the detector array. A motor drive and position sensing device, such as an optical encoder, is used to control motion of the collimator. The motion of the collimator is controlled by a microprocessor controller that measures the speed and position of the detector array simultaneously with the collimator from data provided by optical encoders to ensure that both components move as required to acquire the image and prevent the beam from wandering off of the detector array during a scan. The microprocessor controller also measures and provides a series of control signals that are used to ensure that the system is operating properly. A number of interlocks are required to maintain personnel safety including, but not limited to, the proper functioning of all moving components in the system, such as the detector and collimator motion, as well as generator performance.

In an exemplary embodiment where the detector array includes a plurality of time delay and integration (TDI) charge-coupled device (CCD) arrays, these arrays are approximately 27 inches long. The individual pixels on the CCD array are 48×48 microns and are coated with a scintillating phosphor to convert the incident x-rays into visible light. The detector arrays are connected to a clock driver circuit (camera). There are 128 rows of CCD pixels in the TDI sensor array. The CCD-TCI array can be substituted with a photodiode-CMOS integrated circuit TDI camara array or any similar technology.

The output of the detector array is then sent to a computer workstation where the x-ray image is formed, processed, and displayed. The CCD pixels are mapped into pixels in the output x-ray image by a binning process to produce the desired spatial resolution. The computer workstation also provides the operator interface used to operate and perform routine service functions. The interface is facilitated through a graphical user interface (GUI) program that interacts with the operator to control image acquisition and display and to optimize x-ray imaging parameters. Image and control data signals are received from the detector array and microprocessor controller through a plurality of universal serial bus (USB) interfaces. The GUI and image data are displayed on a high-resolution flat-panel display monitor.

Because the source does not move during the scan, geometric distortion created by a moving source is not developed and the geometric magnification of the acquired image is similar to standard x-ray imaging acquisition methods used for diagnostic x-ray images. Therefore, no separate processing steps are required to correct for such distortions. This configuration reduces the cost and complexity of the system and methods of the invention and increases the speed at which acquired images can be displayed.

Although the invention is illustrated and described herein as embodied in a multi-linear x-ray scanner and methods for scanning, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Additional advantages and other features characteristic of the present invention will be set forth in the detailed description that follows and may be apparent from the detailed description or may be learned by practice of exemplary embodiments of the invention. Still other advantages of the invention may be realized by any of the instrumentalities, methods, or combinations particularly pointed out in the claims.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present invention. Advantages of embodiments of the present invention will be apparent from the following detailed description of the exemplary embodiments thereof, which description should be considered in conjunction with the accompanying drawings in which.

DETAILED DESCRIPTION OF THE EMBODIMENTS

Figure 1:
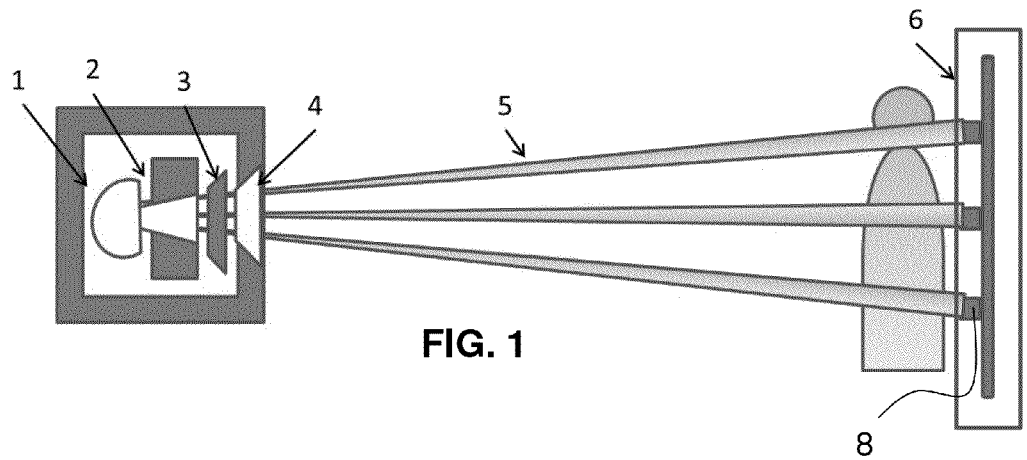
FIG. 1 is a schematic diagram of an exemplary embodiment of an implementation of an x-ray beam forming and imaging system including a shielded housing containing an x-ray generator, a filter, a dosimeter, and a collimator with a plurality of horizontal x-ray beams passing through a person being scanned and impinging on a detector array including a plurality of linear x-ray detectors.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

The terms "program," "software," "software application," and the like as used herein, are defined as a sequence of instructions designed for execution on a computer system. A "program," "software," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments of the present invention are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 2:
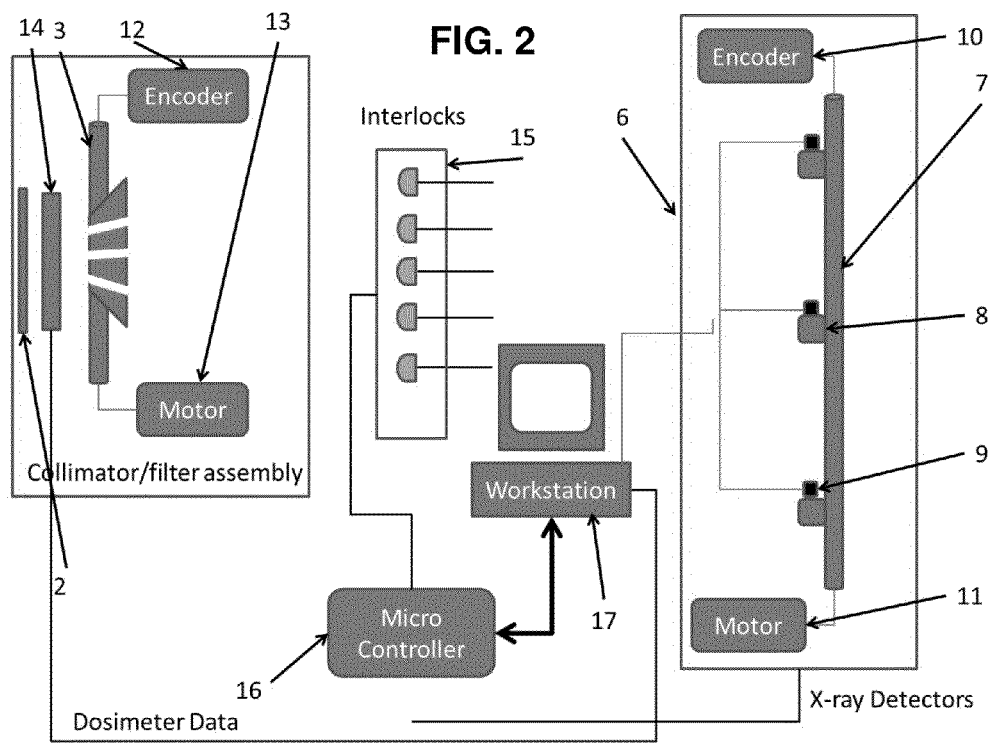
FIG. 2 is a block and schematic circuit diagram of an exemplary embodiment of an implementation of an image acquisition system with microprocessor controller that interact with one another to control production of x-rays and formation of an image with the x-ray generator not shown in the drawing.
Figure 3:
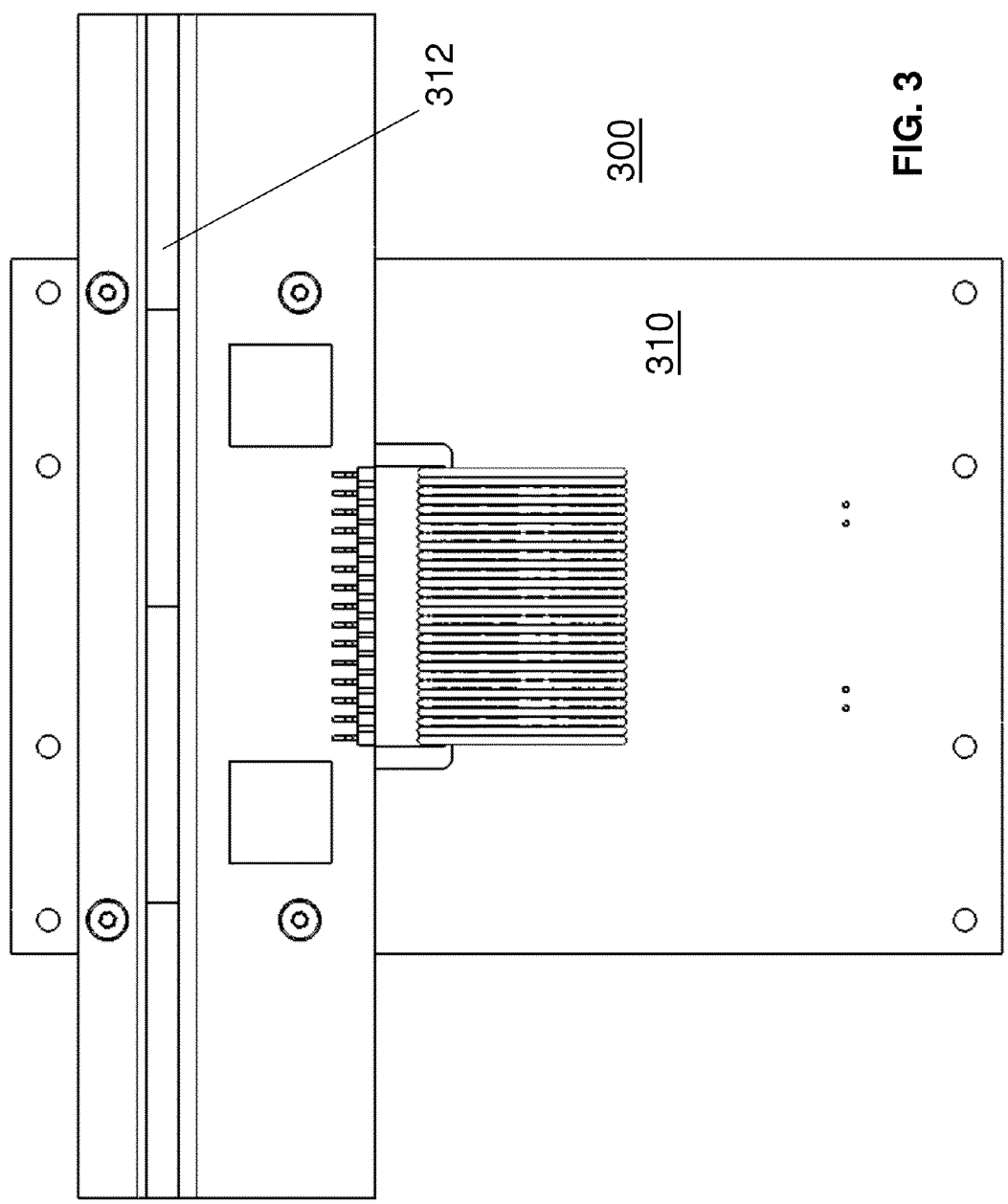
FIG. 3 is an elevational view of an exemplary embodiment of an x-ray detector from a detector side.
Figure 4:
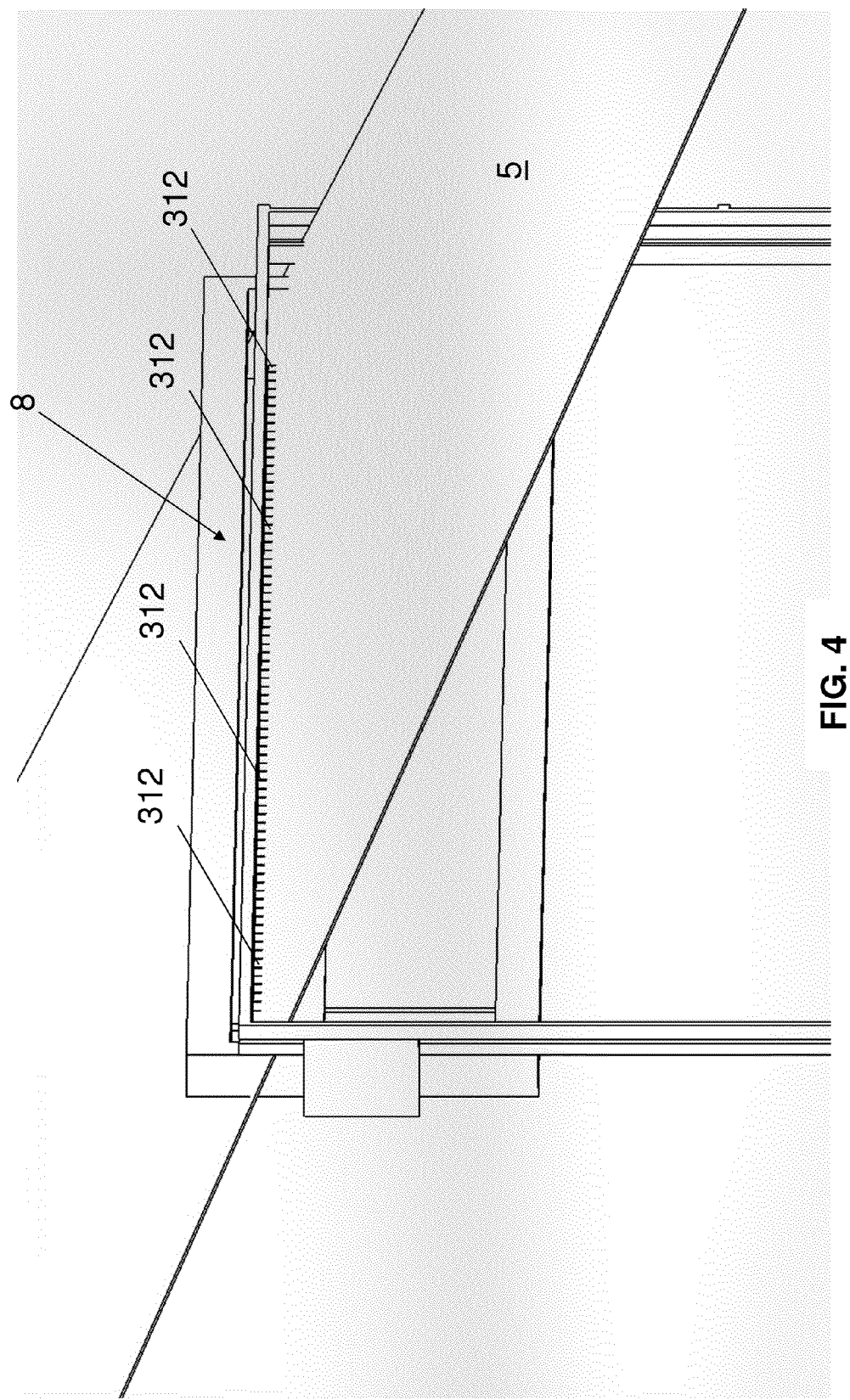
FIG. 4 is a fragmentary, perspective view of the x-ray detector of FIG. 3 with an impinging x-ray beam.

Described now are exemplary embodiments of the scanning systems and methods. Referring now to the figures of the drawings in detail and first, particularly to FIGS. 1 and 2, there is shown an x-ray source 1 as a monoblock generator capable of producing a fan beam of x-rays with a maximum energy of at least 150 keV and a maximum tube current of at least 3 milliamperes. An example of such a generator is made by Spellman High Voltage Electronics Corporation (model XRB201) in Hauppauge, N.Y. The x-ray generator is mounted on a platform 2 to 3 feet high and housed in a lead-lined cabinet with the x-ray output pointed toward a detector assembly 6 having at least one detector array 8 (see FIG. 2), an example of which can be a photodiode array. Examples of the array 8 are made by X-Scan Imaging Corporation and another Hamamatsu Photonics, K.K. A filter wheel 2 containing one or more filters made of aluminum and copper of varying thicknesses (Al 1-2 mm, Cu 0.1-0.2 mm) is placed in close proximity (within a few centimeters) to the output of the generator to intercept and filter the x-ray beam. A collimator 3 containing a plurality of horizontal slits is placed adjacent the filter 2 to intercept and collimate the filtered x-ray beam into a plurality of horizontal beams of x-rays such that the height of the x-ray beams are the same dimension as the photodiodes in the detector arrays 8. The collimator 3 is moved up and down by a motor 13 that is controlled by a microprocessor controller 16. The microprocessor controller 16 receives data from an encoder 12 mounted on the collimator assembly that provides data on the position and speed of the collimator 3. X-rays emitted by the collimator 3 pass through an aperture 4 that confines the dimension and movement of the x-ray beams 5 within the active area defined by the detector arrays 8, which are moved along vertical supports 7 by a slide drive motor 11. The position and speed of the detector arrays 8 is monitored by an encoder 10 that sends data to the microprocessor controller 16.

Each detector array 8 in the embodiment of a photodiode array is a linear array containing a plurality of individual photodiodes. In an exemplary embodiment, there are a total of 320 diodes in each array 8 and a total of three individual linear arrays 8. The length of the individual linear arrays 8 is approximately 28 inches. Each of these linear arrays 8 is illuminated by the collimated x-ray beams 5 emitted by the x-ray source 1. When the amount of x-rays is absorbed in the diode array to produce an adequate exposure, the diode arrays are read out and three rows of the x-ray image are formed. The slide motor drive 11 for the diode array then indexes the size of a photodiode (2.5 mm) and rests while the diodes acquire another exposure to acquire three additional rows of pixels in the output x-ray image. This process is repeated until the entire length of the image size has been scanned. The slide motor 11 moves the arrays 8 a total distance of 670 mm (26 inches), thereby simultaneously creating three images that are 28 inches wide and 26 inches tall. These three images are stacked one on top of another and are stitched together by the image processing software or program in the workstation 17 to produce a composite image that is two meters tall (78 inches) by 0.67 meters wide (28 inches).

In accordance with an exemplary embodiment, the arrays 8 are photodiode arrays manufactured by Detection Technology Oy (Micropolis, Finland). The photodiodes are mounted on a linear array x-ray detector card (X-Card SE). In one exemplary embodiment, fifteen X-Cards (five cards on each of the three separate linear arrays 8) are connected to a single data acquisition board (X-DAQ) associated with the workstation 17 and/or the microcontroller 16. Each X-Card contains sixty-four photodiodes. The X-DAQ contains on-board signal processing functions and real-time image data acquisition to send to the computer workstation 17, for example, via Ethernet.

Figure 5:
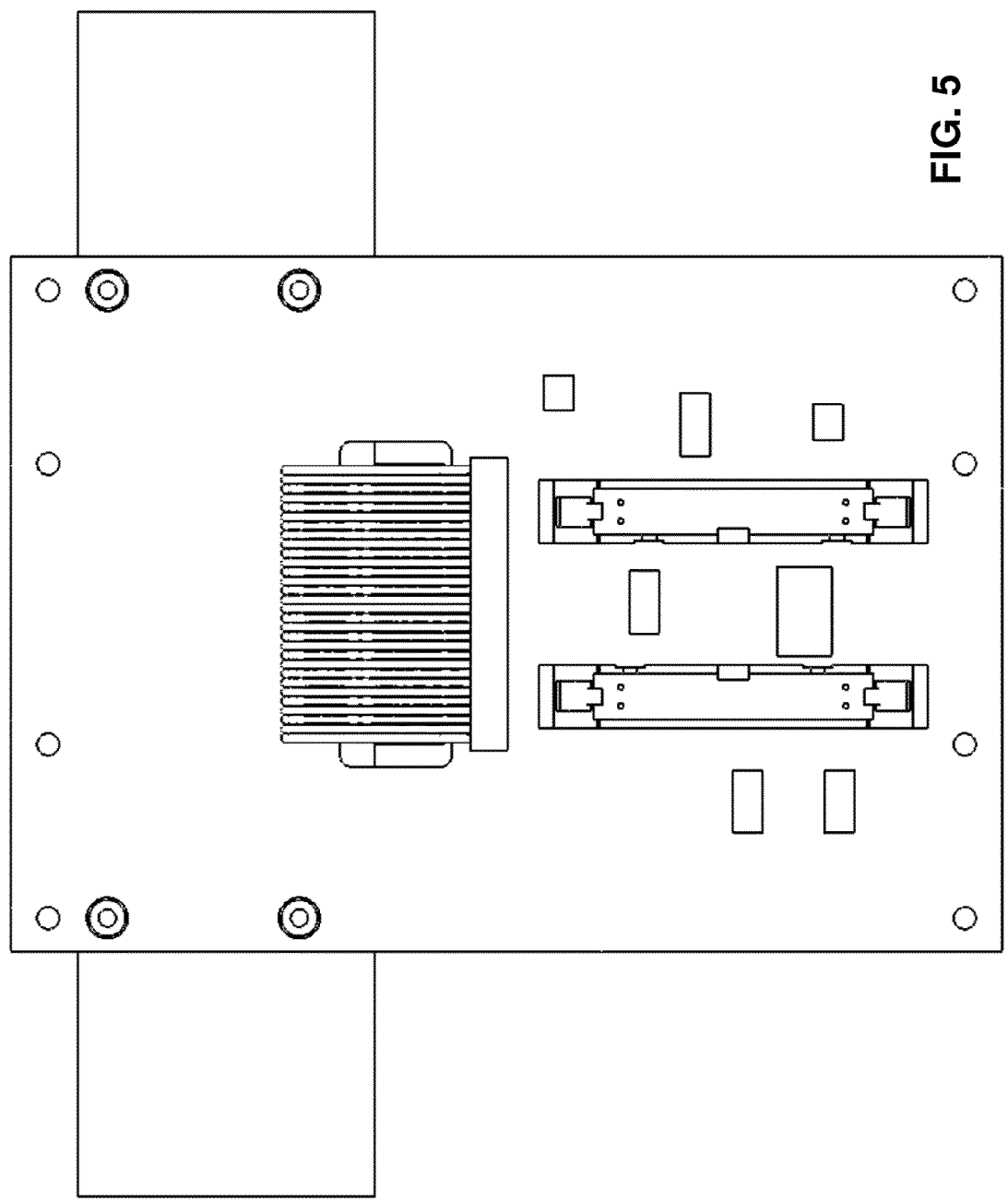
FIG. 5 is an elevational view of the x-ray detector of FIG. 3 from opposite the detector side.
Figure 7:
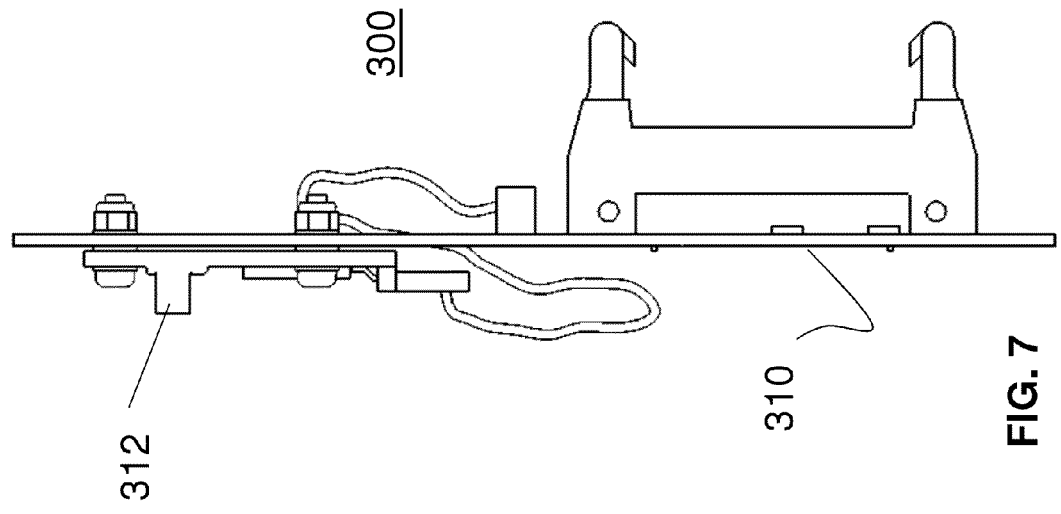
FIG. 7 is a right-side elevational view of the x-ray detector of FIG. 3.
Figure 6:
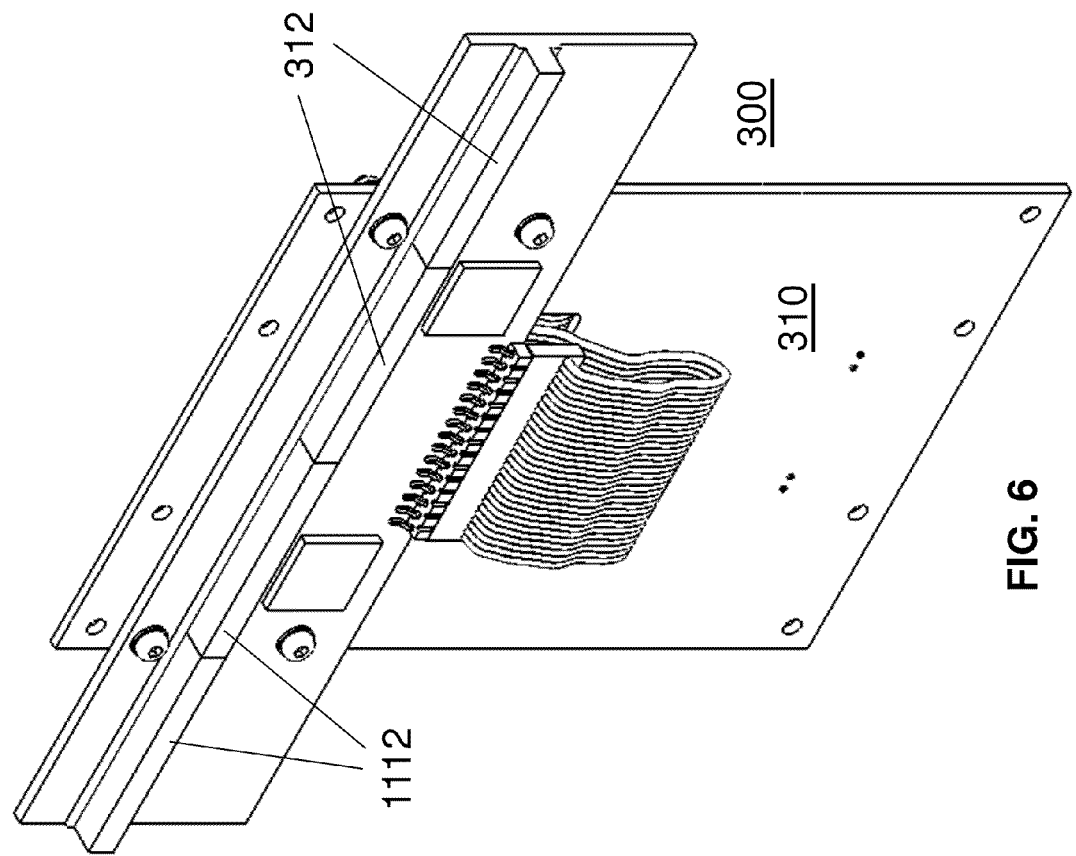
FIG. 6 is a perspective view of the x-ray detector of FIG. 3 from the detector side.
Figure 8:
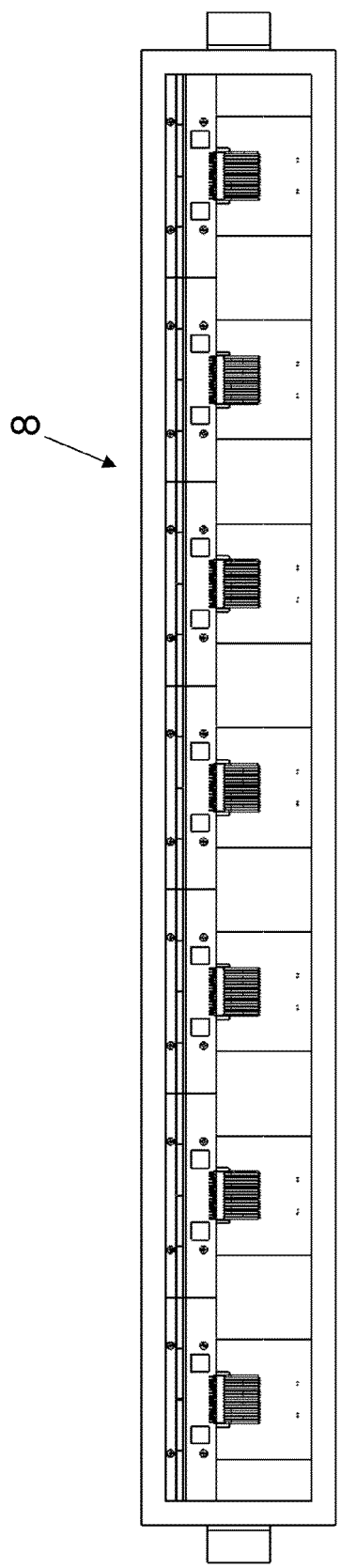
FIG. 8 is an elevational view of an exemplary embodiment of an x-ray detector array having a plurality of the x-ray detectors of FIG. 3 from a detector side.
Figure 9:
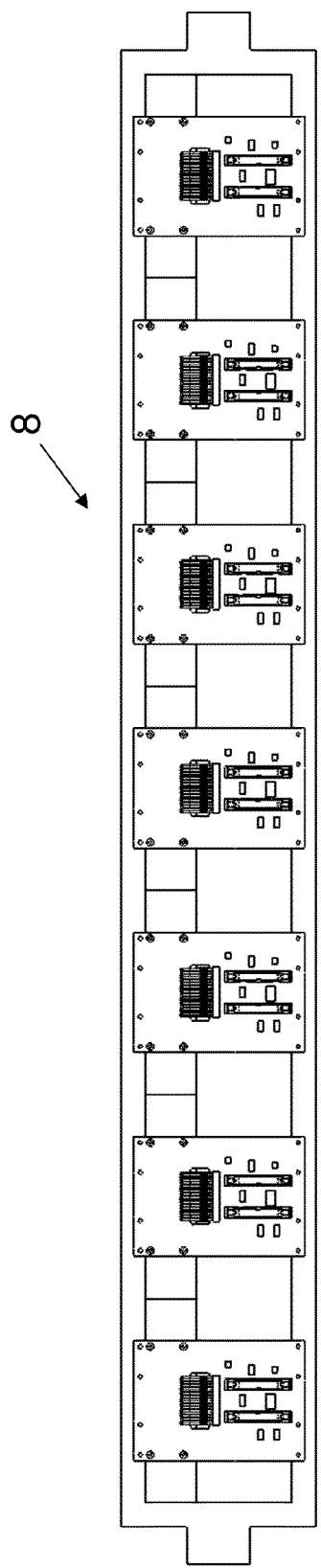
FIG. 9 is an elevational view of the x-ray detector array of FIG. 8 from opposite the detector side.
Figure 10:
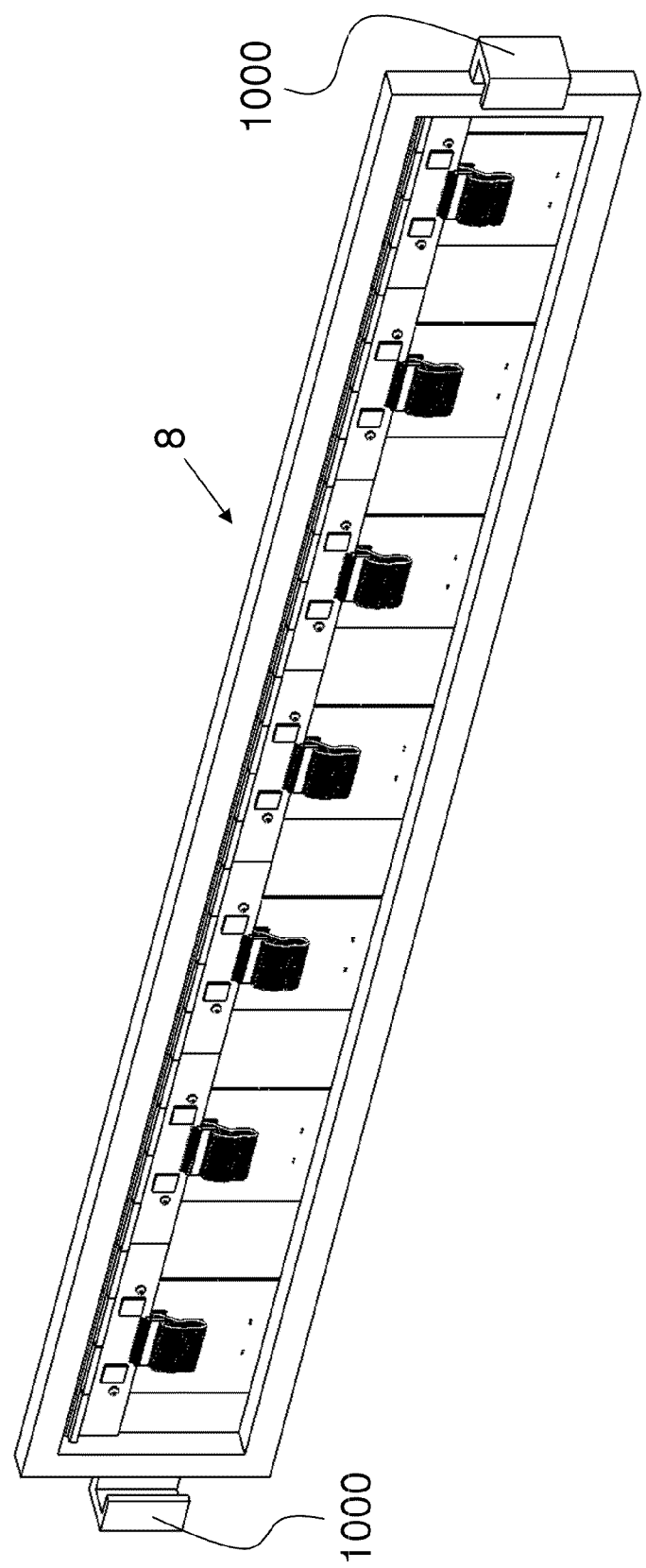
FIG. 10 is a perspective view of the x-ray detector array of FIG. 8.

One exemplary embodiment of an x-ray detector card 300 usable in the various embodiments described herein is shown in FIGS. 3 to 7. The card 300 has a detector side 310 on which resides an x-ray detector 312. Here, there are four individual x-ray detectors 312 set along an axis that is to be aligned with an incoming beam of x-rays, as shown, for example, by the beam 5 in FIG. 4. Various views of the card 300 are shown in FIGS. 5, 6, and 7. The card 300 is modular and, therefore, can be set up in a linear array 8 of photodiodes shown, for example, in FIGS. 8, 9, and 10. Appropriate connectors 1000 can be used to secure the array 8 to the vertical support 7 of the detector assembly 6 for movement, for example, effected by the slide motor drive 11, or to any other detector assembly described herein in the various exemplary embodiments.

The technique factors (filtration, kV, mA, and exposure time) used to expose the person being scanned are optimized by software installed on the workstation 17. This software monitors the exposure level of the arrays 8 and data from the microprocessor controller 16 while the x-ray beams 5 are exposing the arrays 8 to adjust the technique factors produced by the x-ray generator 1 such that the intensity and contrast of the x-ray image is maximized while the exposure dose is minimized for each person being scanned. This program is similar in nature to programs and devices used by medical diagnostic x-ray equipment for fluoroscopic imaging to dynamically control exposure and image quality commonly referred to as Automatic Brightness Systems (ABS).

In accordance with an exemplary embodiment utilizing photodiode arrays, the ABS system is carried out by taking the digital output value from each photodiode after exposure, defining a region of anatomical exposure (those photodiodes located behind the person and not directly exposed to the x-ray source), and averaging those values into a single value. This single average value is then compared to a target value that is equal to one half of the saturated value of the photodiode (from an exposure just large enough to saturate the photodiode). If the average value is lower than the target value, then the x-ray intensity (mA) is increased or the kV of the x-ray spectrum is increased to drive the average value to the target value during the next line of exposure. Conversely, if the average value is higher than the target value, then the kV and mA values are lowered. Alternatively, the scanning speed could be adjusted to change the exposure time for each photodiode, thereby changing the mAs or integrated exposure value. The kV and mA values are changed according to a pre-determined relationship or look-up table (LUT) that is created and optimized by experimentation with the image quality produced at various x-ray technique values (kV and mA) using anatomically correct phantoms.

In an alternative exemplary embodiment, dedicated single photodiodes 9 are mounted on each of the individual arrays 8 of photodiodes 9. These photodiodes 9 are exposed and produce the digital output value used to compare with the target value. Accordingly, the shape of the collimator openings have notches in them to permit x-rays to pass through and expose the photodiodes 9.

Figure 11:
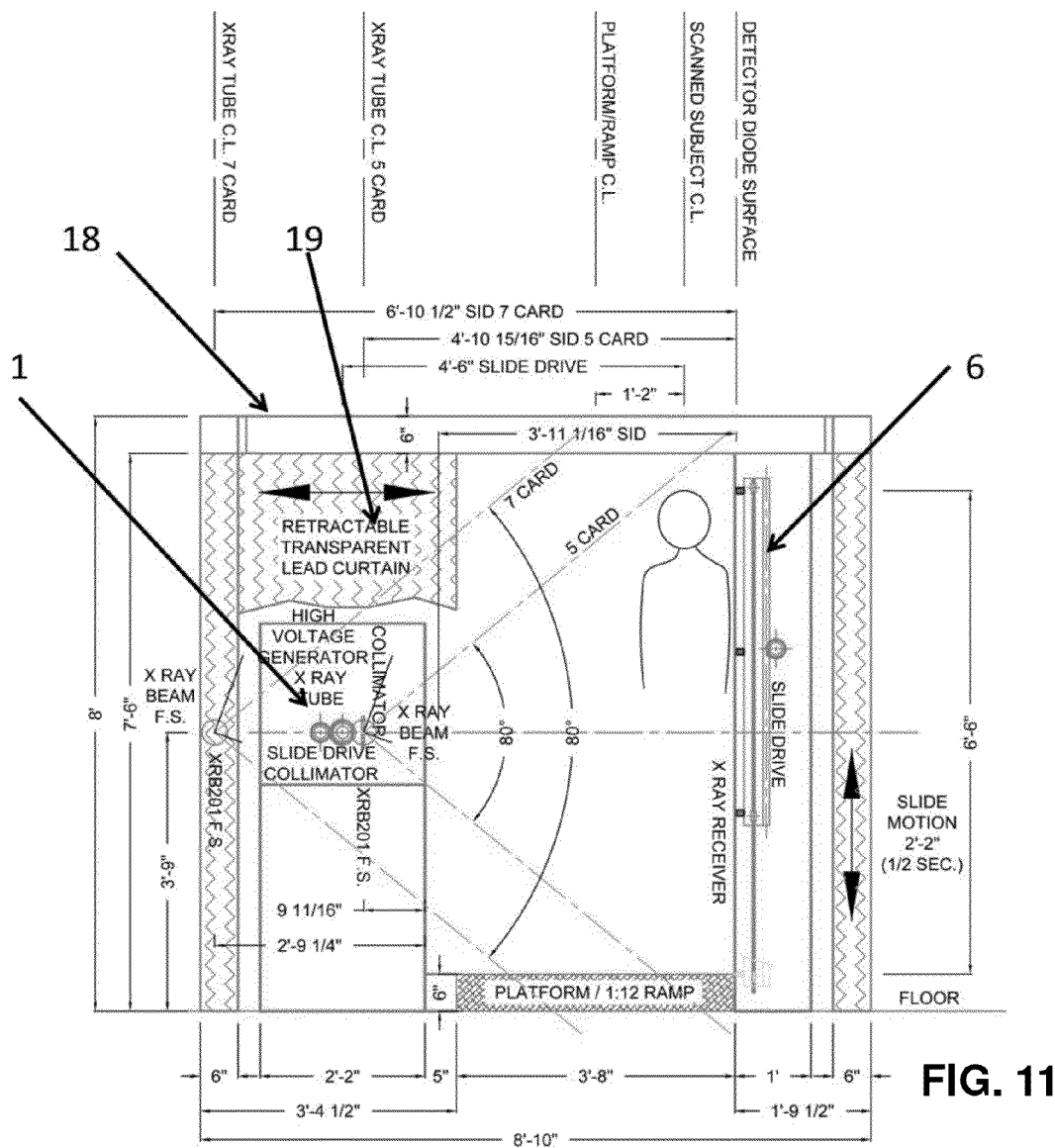
FIG. 11 is a schematic side elevational view of an exemplary embodiment of a multi-linear x-ray scanner having a partially-closed configuration that includes a scanning booth with a retractable curtain to completely cover the entry point and, thereby, complete an x-ray enclosure.
Figure 12:
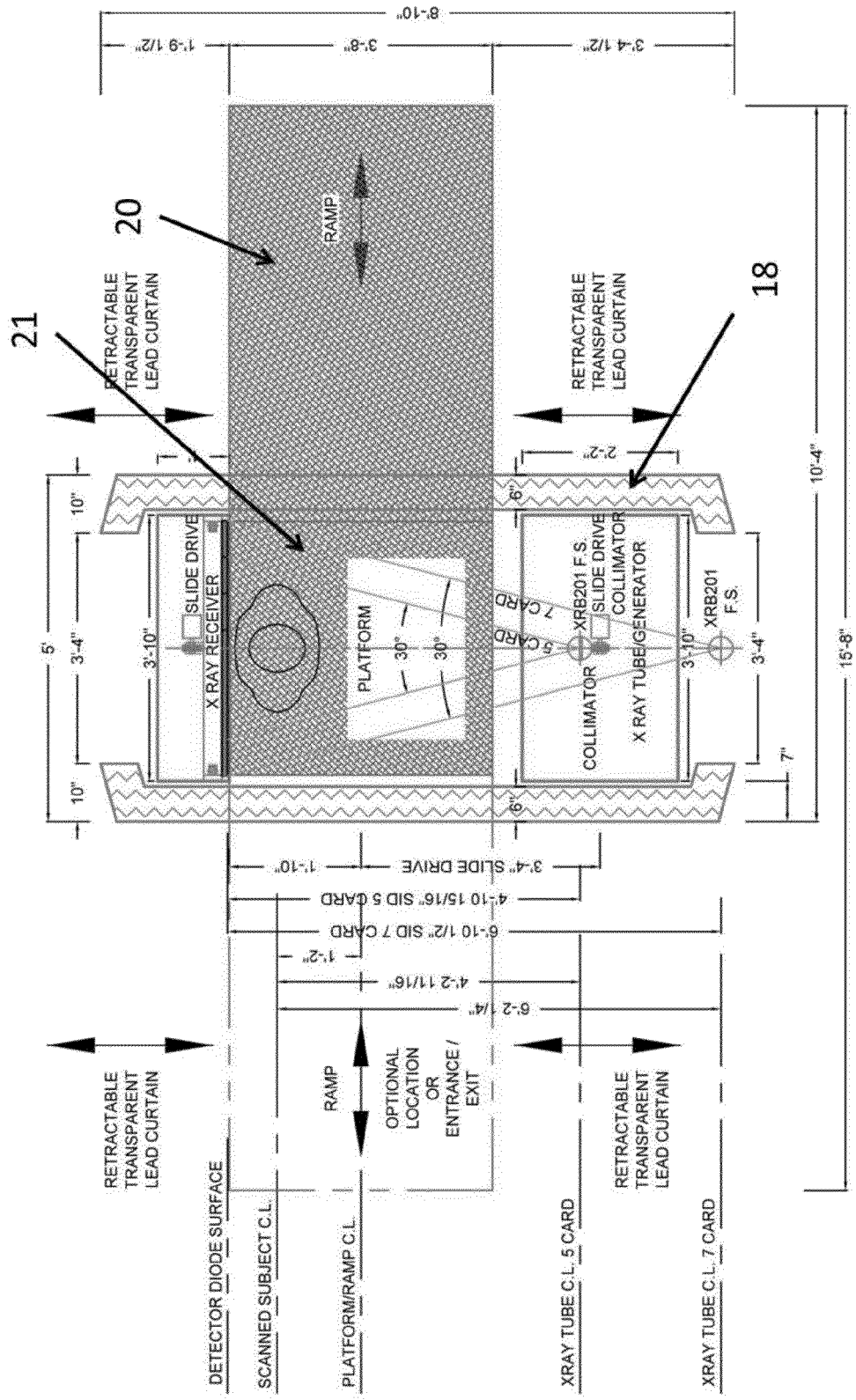
FIG. 12 is a schematic top plan view of the multi-linear x-ray scanner of FIG. 11.

An exemplary method of operating the x-ray scanner begins when the operator initializes the scanner from the GUI on workstation 17. The person to be scanned enters the scanner through an opening in the scanner housing 18 created by the sliding shielded door 19 as shown, for example, in FIGS. 11 and 12. The person enters the scanner by walking up a ramp 20 and stands facing the x-ray generator 1 on a platform 21. A person using a walker, crutches, or a wheelchair can also enter the scanner on the ramp 20. The platform 21 and all interior surfaces of the scanning area are made from a material that is transparent to x-rays and is structurally sound, such as a carbon-fiber composite. Once the person is properly positioned, the sliding door 19 closes and the x-ray scan is initiated. Approximately 0.5 seconds later, the scan is complete and, if the operator is satisfied with the quality of the image, the door 19 is opened.

The image produced by the scanner can be studied to determine if any items of interest are hidden on the person being scanned. The images can be saved on a memory (e.g., a hard drive) of the workstation 17 for later review. The dose used to acquire each image can also be stored as well.

Safe operation of the scanner is ensured by the use of several interlocks 15 that are connected to, but are not limited to, the sliding door 19, the x-ray generator 1, the array 8, and other components such as the collimator 3 to ensure that x-rays are not emitted unless the door is closed and that x-rays are properly aligned with the movement of the array 8. The interlocks 15 are managed by the microprocessor controller 16.

Figure 13:
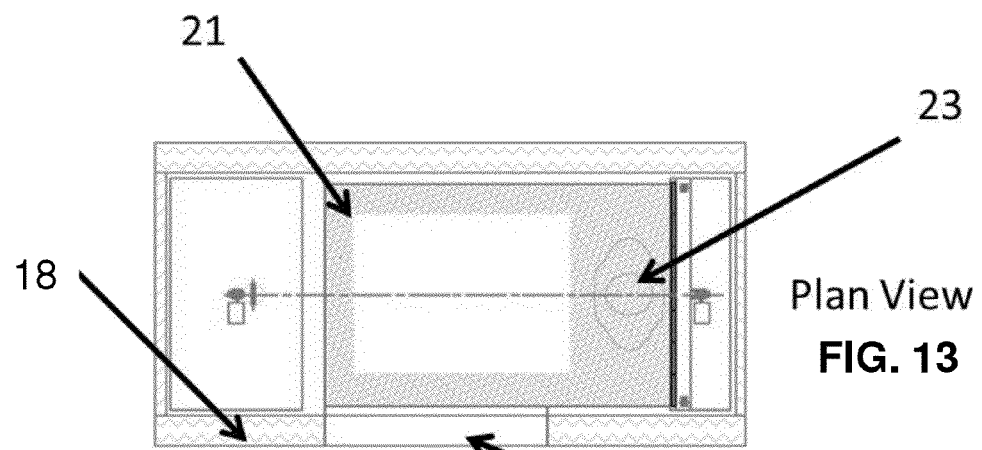
FIG. 13 is a schematic top plan view of an exemplary embodiment of a multi-linear x-ray scanner having a partially-closed configuration that includes a scanning booth without completely covering the entry point but with a partition offset from a plane of the detector array so that the scanning subject sits or stands behind an alcove-like cavity that creates a shielded area to apply a technique referred to as "shadow-shielding" that reduces an exposure dose around the booth.
Figure 14:
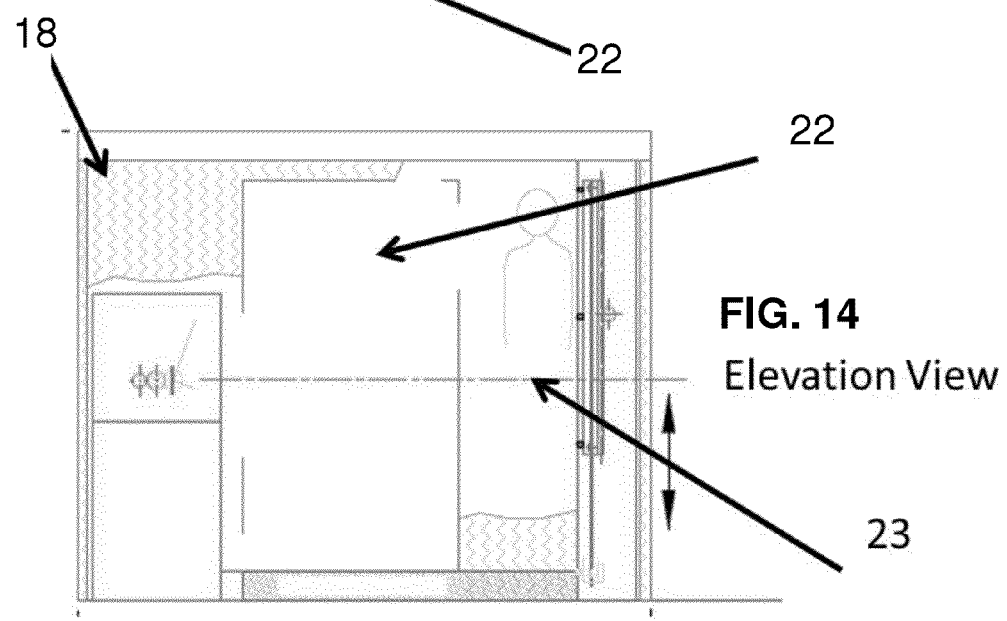
FIG. 14 is a schematic side elevational view of the multi-linear x-ray scanner of FIG. 13 from a door side of the scanner booth.
Figure 15:
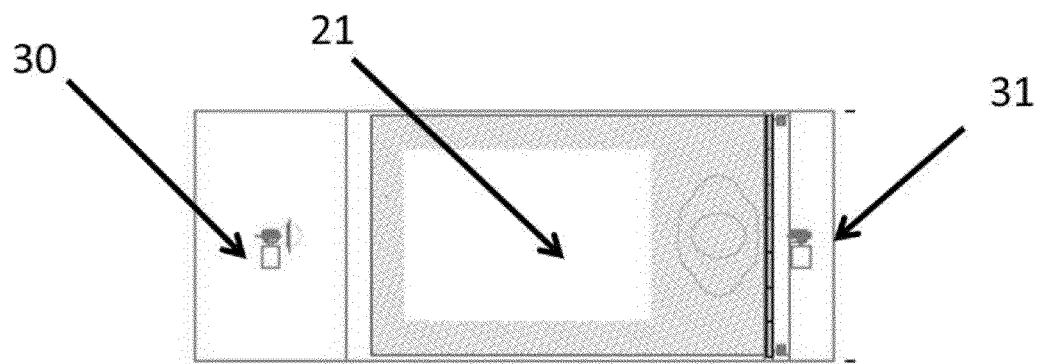
FIG. 15 is a schematic top plan view of an exemplary embodiment of a multi-linear x-ray scanner with a configuration that includes only a generator cabinet and an imaging cabinet, neither of which are enclosed, to result in an open scanning area utilizing no external shielding desirable where a small footprint is required.
Figure 16:
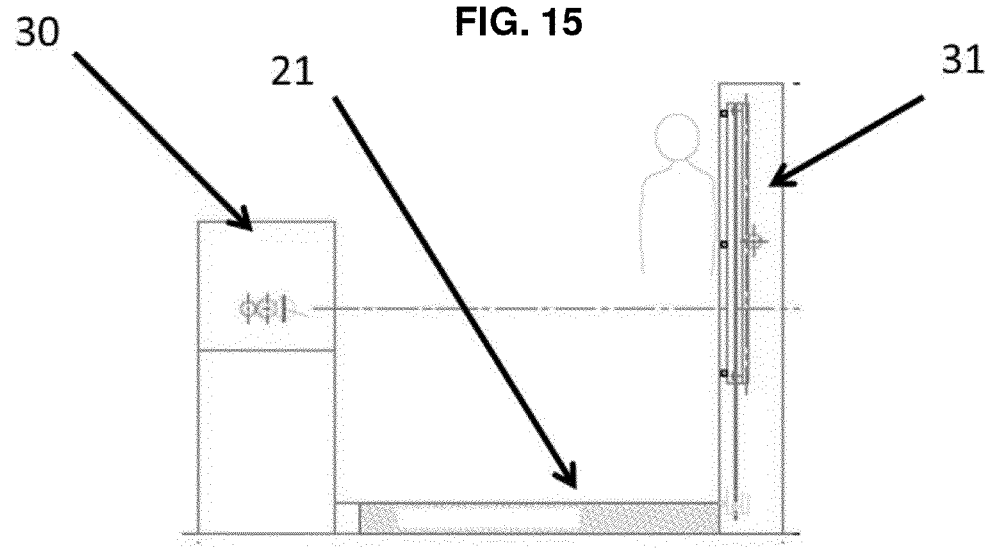
FIG. 16 is a schematic side elevational view of the multi-linear x-ray scanner of FIG. 15.

FIGS. 13 to 18 show other exemplary embodiments of a scanning system that can be configured in several different ways to accommodate the needs of different market applications. For example, as shown in FIGS. 13 and 14, the system can be configured to eliminate the sliding door 19 and to move the door opening 22 to the scanner housing 18 away from the plane of the array 8 to create a shielded cavity 23 that can shield scattered x-rays produced during a scan. In this exemplary, configuration there no need for a sliding door 19, thereby reducing the cost of the system and simplifying the operation of the system.

Another system configuration can be created by eliminating the scanner housing 18 entirely. In this exemplary configuration, illustrated in FIGS. 15 and 16, all of the components that produce the scanning x-ray beams 5 including the x-ray source 1, filter wheel 2, collimator 3 and aperture 4 are enclosed in a lead-lined generator cabinet 30. All of the components used to make the image including the arrays 8, vertical support 7, slide drive motors 11 and encoder 19, and microprocessor controller are enclosed in an imaging cabinet 31. The position and distance between the generator cabinet 30 and the imaging cabinet 31 must be precisely controlled and is dictated by the geometry of the scanning system. In particular, the cone beam width of the x-ray source 1 and array 8 (e.g., the number of photodiodes in the array) of the scanner determine the relative position and distance between the two cabinets. The platform 21 is placed in the space between the cabinets to form an open scanning area having no shielded walls. The platform 21 allows the arrays 8 to scan below the level of the feet of the person being scanned to create a view of their shoes and feet.

Figure 17:
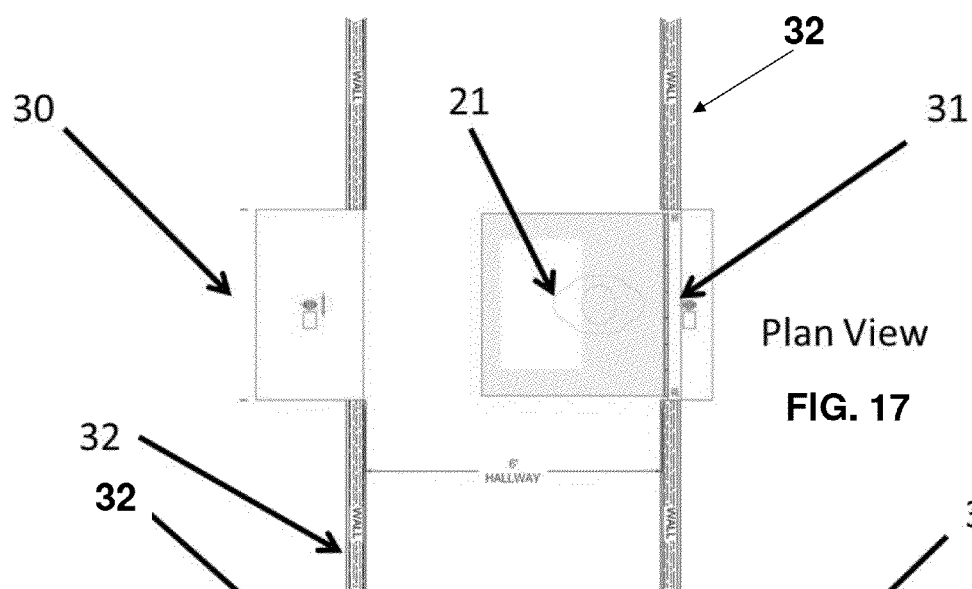
FIG. 17 is a schematic top plan view of another exemplary embodiment of a multi-linear x-ray scanner with the generator and imaging cabinets recessed in or positioned behind walls where the walls and the space in between form the scanning area.
Figure 18:
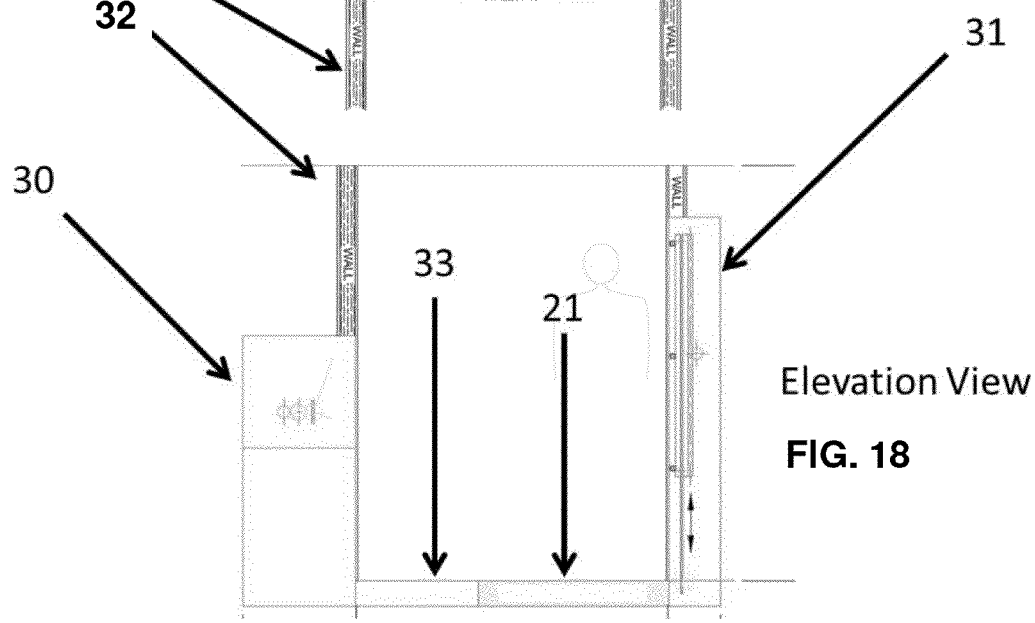
FIG. 18 is a schematic side elevational view of the multi-linear x-ray scanner of FIG. 17.
Figure 19:
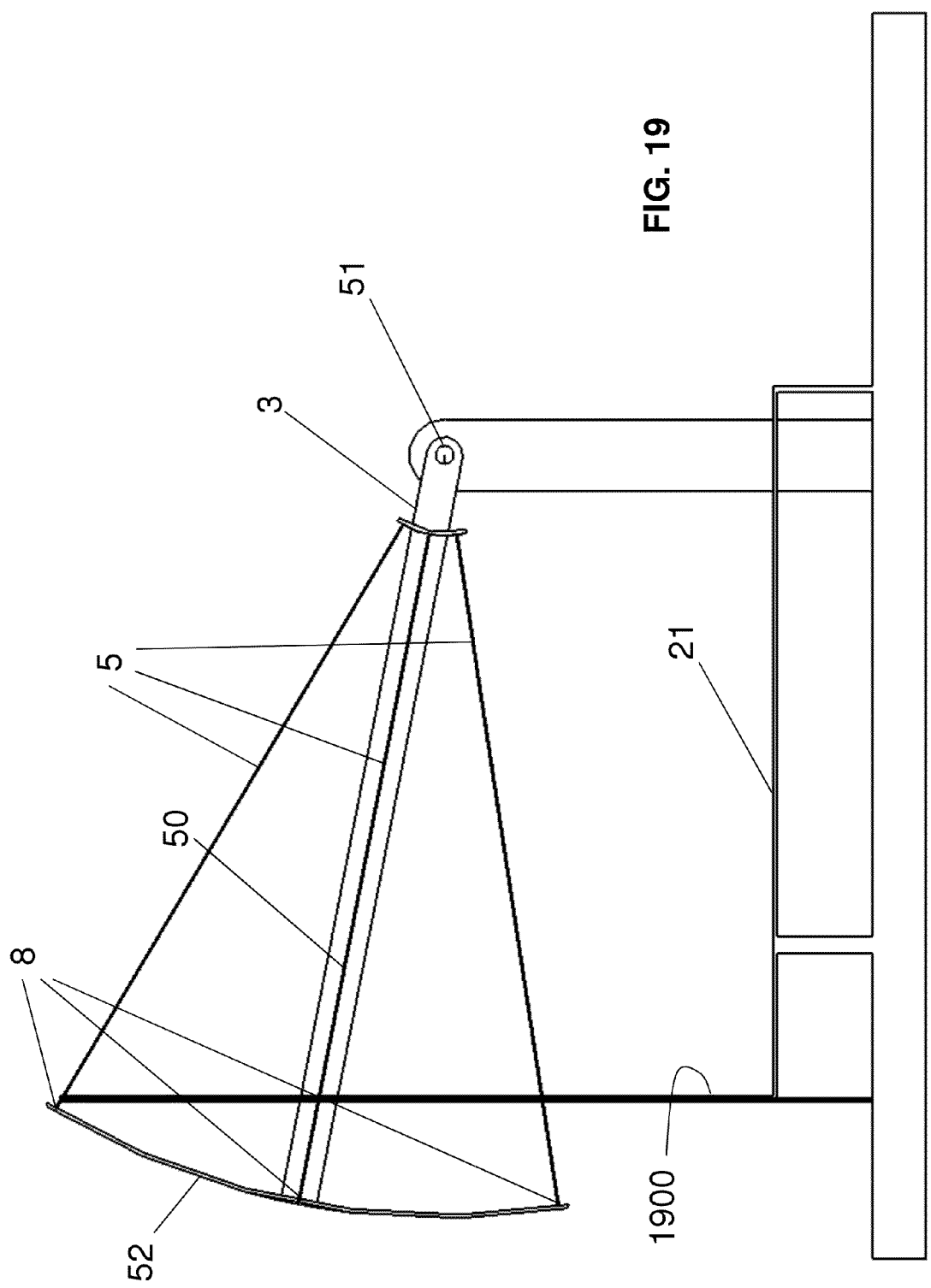
FIG. 19 is a side elevational view of an exemplary embodiment of a multi-linear x-ray scanner with the generator cabinet removed but showing a collimator and with a detector array sub-assembly in a raised position.
Figure 20:
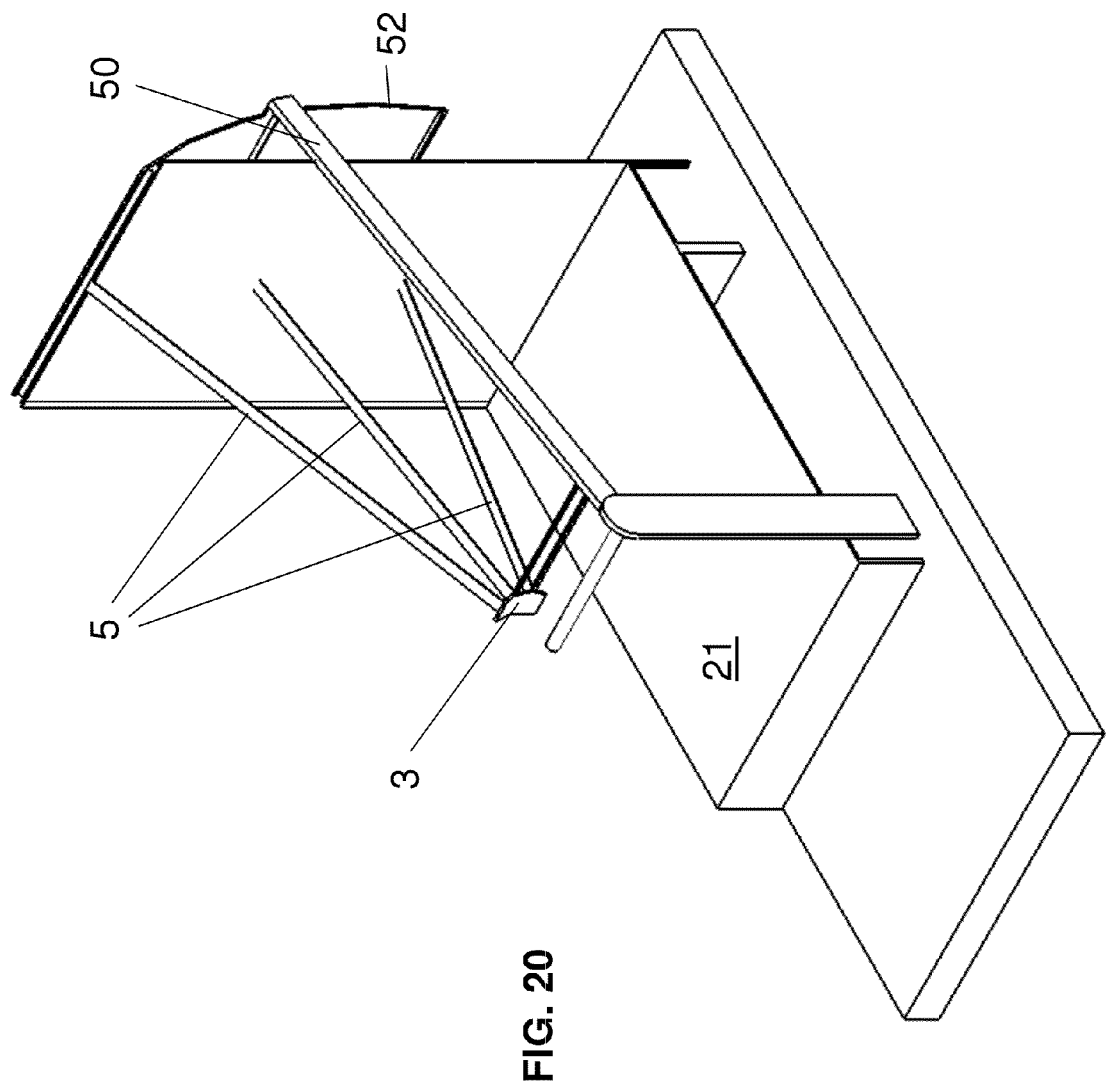
FIG. 20 is a perspective view of the multi-linear x-ray scanner of FIG. 19.
Figure 21:
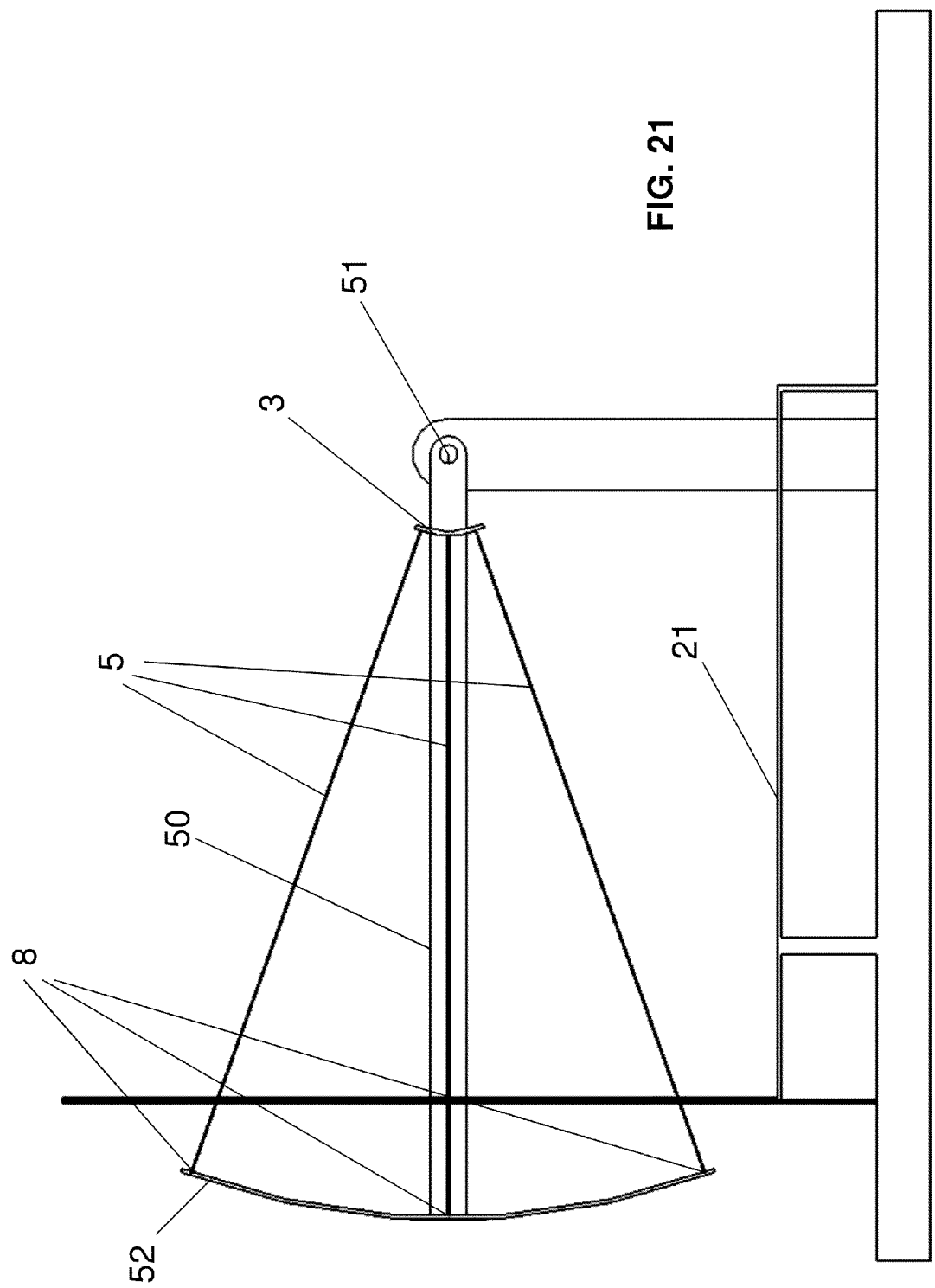
FIG. 21 is a side elevational view of the multi-linear x-ray scanner of FIG. 19 with the detector array sub-assembly in an intermediate position.
Figure 22:
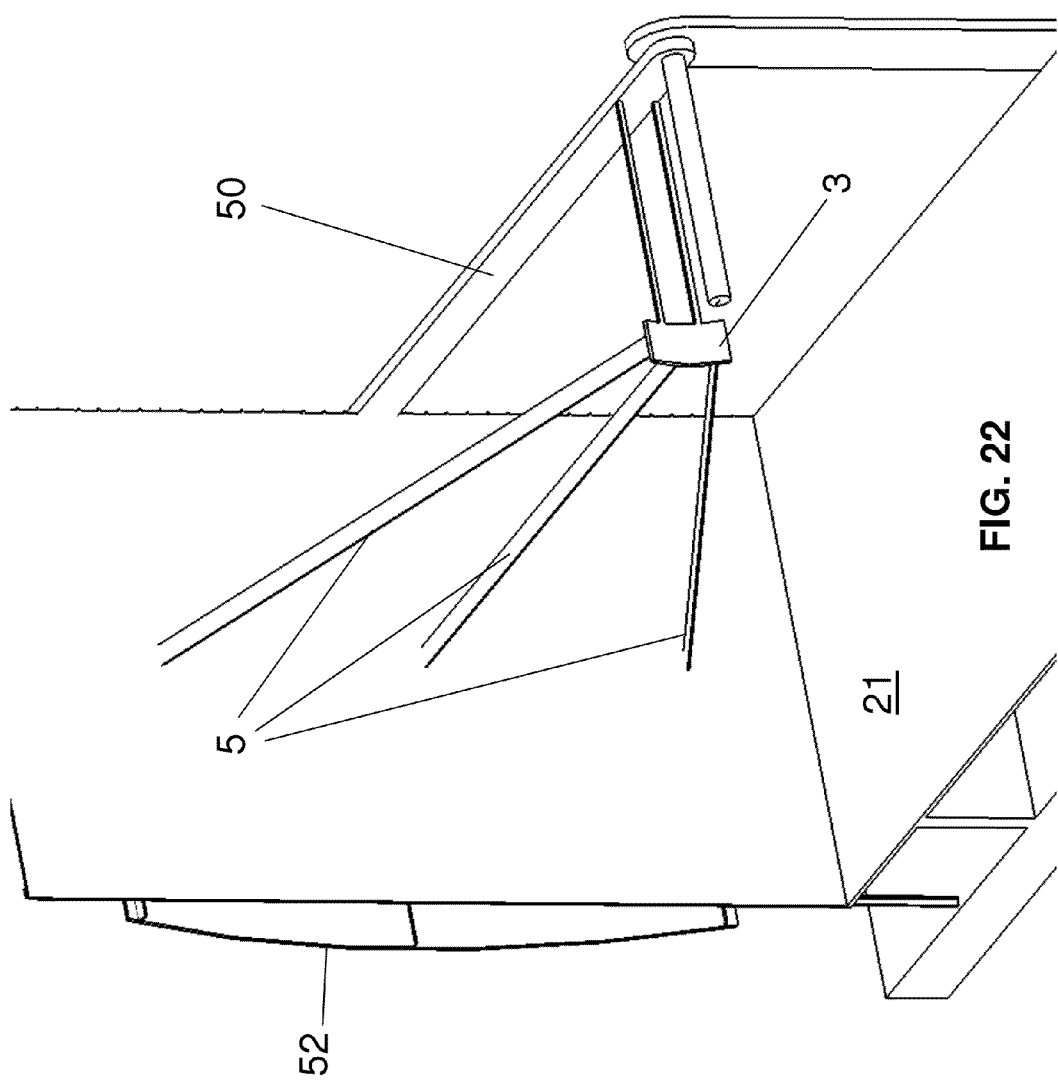
FIG. 22 is a perspective view of the multi-linear x-ray scanner of FIG. 21.

An advantage of this "open" configuration is that the system can be installed in buildings and rooms such that none of the components of the system are visible. This configuration can be created by placing the generator cabinet 30 behind or in a wall 32 of a room or hallway and placing the imaging cabinet 31 behind or in an opposing wall, as shown in FIGS. 17 and 18. The opposing walls 32 of the room or hallway are closer together than the distance required between the generator cabinet 30 and the imaging cabinet 31. The walls 32 have x-ray translucent materials, such as a carbon-fiber composite, to minimize the x-ray attenuation and scatter. To avoid the need of a raised platform 21, the imaging cabinet 31 can be placed several inches or more below ground level to allow imaging of the feet and shoes. In such a configuration, none of the components of the system are visible to anyone, providing very discrete measures for providing security in facilities like hotels, private residences, and other venues where the security apparatus must keep a very low profile.

Another advantage of the open cabinet design is that the scanner housing 18 can be customized to provide additional security and safety features. The need for such additional features is particularly important in areas of the world where terrorists are known to operate. Specifically, it is advantageous to make the scanner housing 18 blast-proof and/or bullet-proof. This feature protects occupants of the building from a suicide bomber setting off a bomb when confronted with discovery. Other features could be incorporated in the scanner housing 18 including both lethal and non-lethal measures for subduing an armed and dangerous person being scanned.

Figure 23:
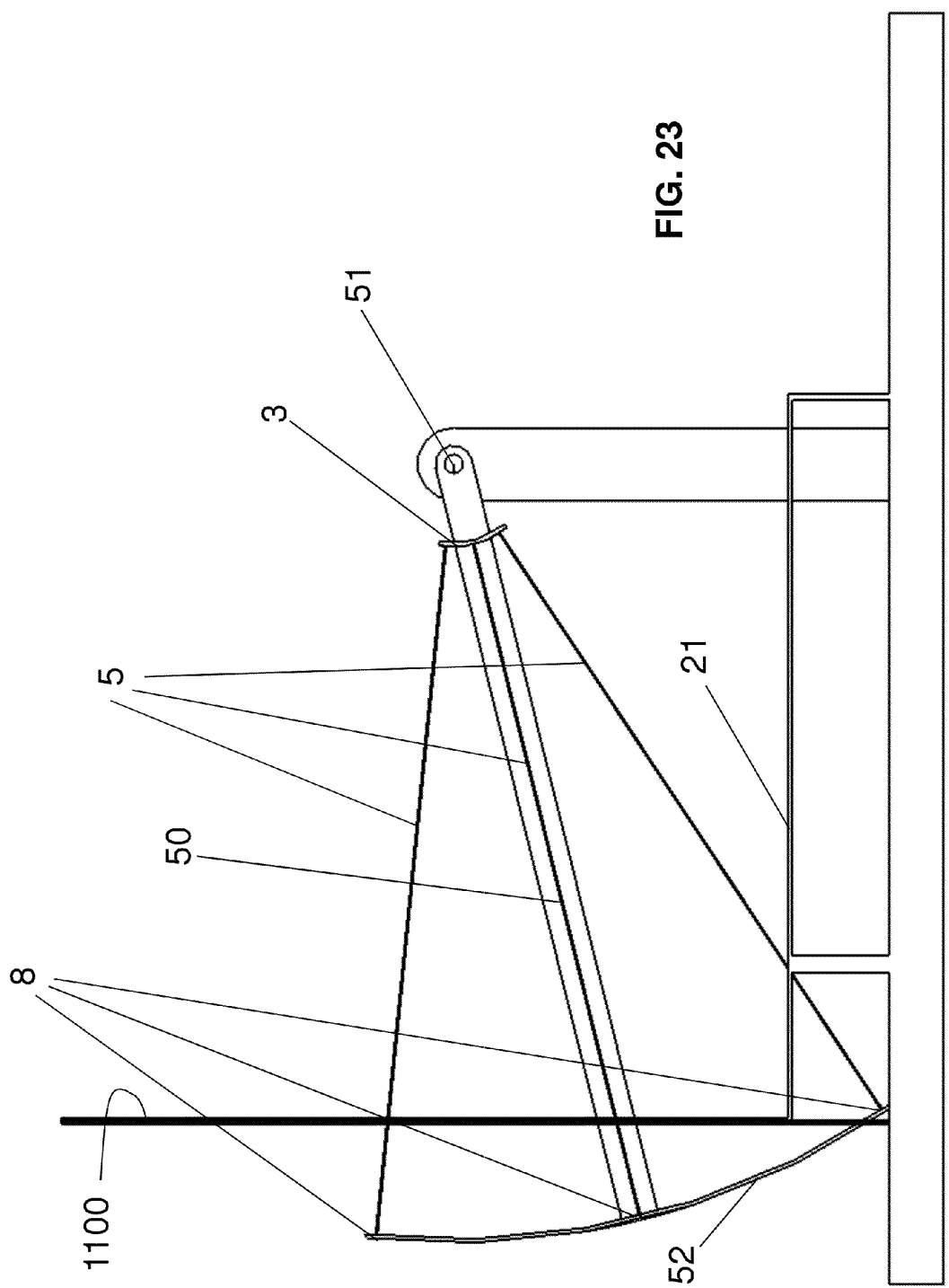
FIG. 23 is a side elevational view of the multi-linear x-ray scanner of FIG. 19 with the detector array sub-assembly in a lowered position.
Figure 24:
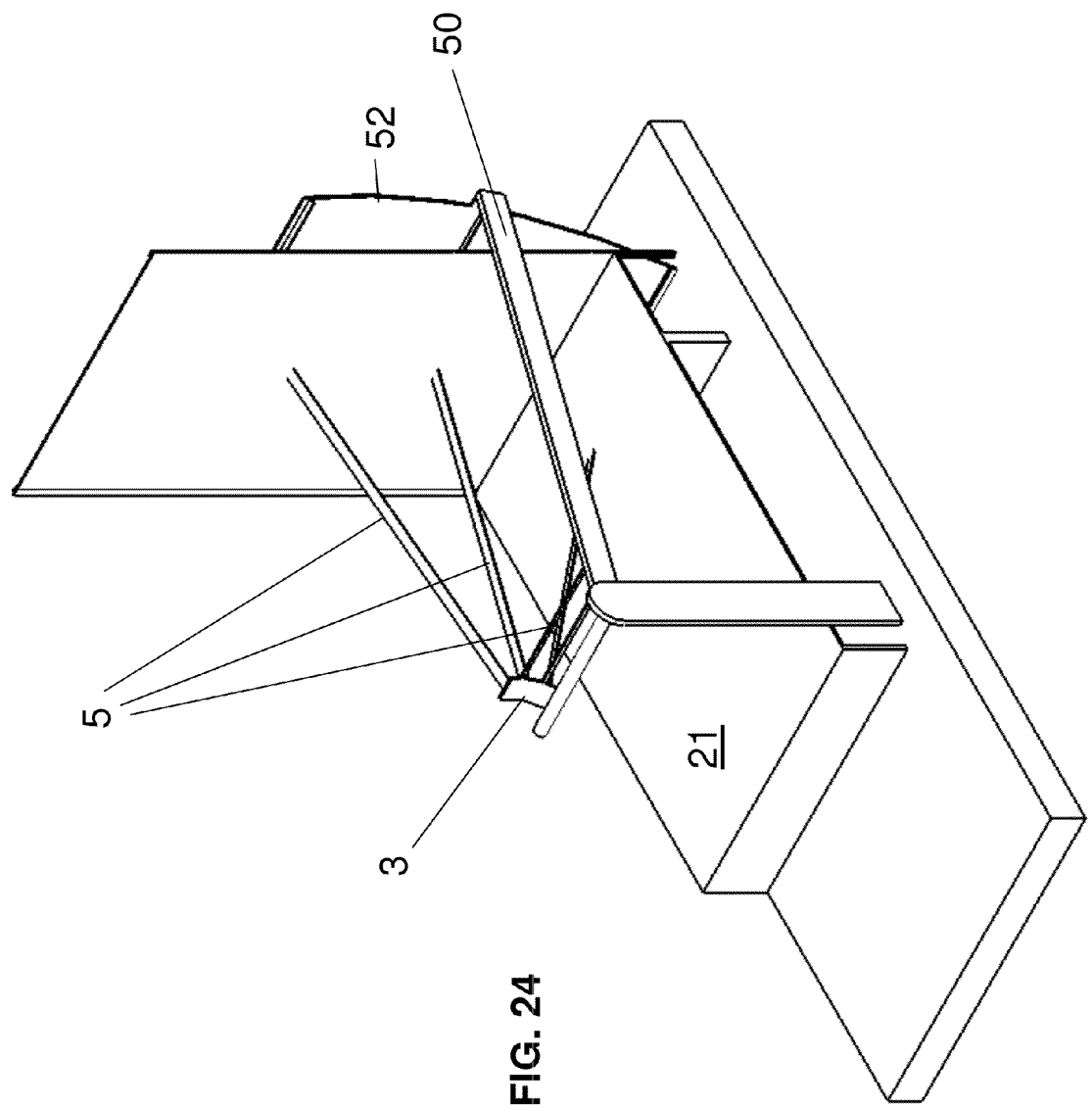
FIG. 24 is a perspective view of the multi-linear x-ray scanner of FIG. 23.
Figure 25:
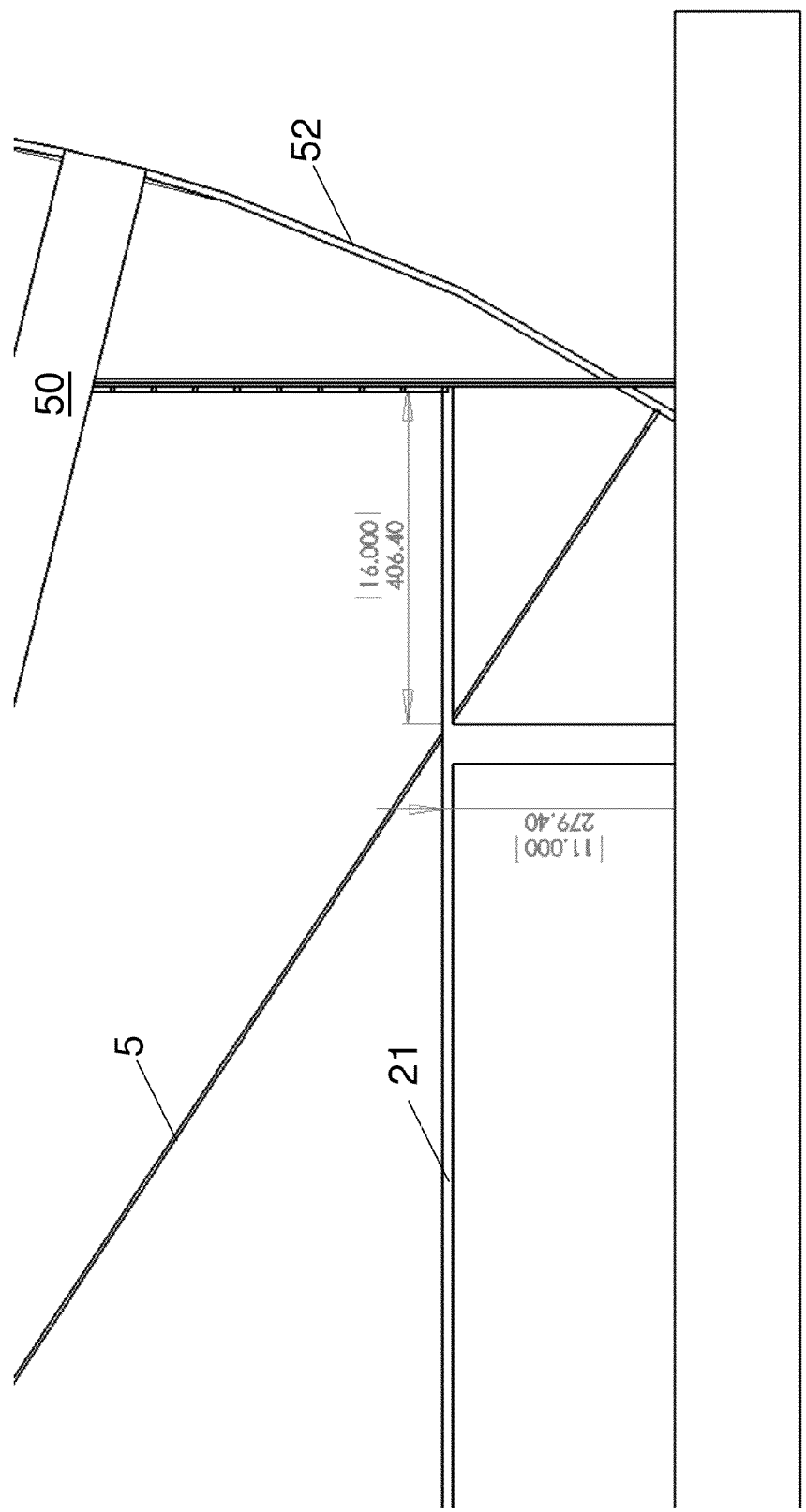
FIG. 25 is a fragmentary, enlarged, side elevational view of the multi-linear x-ray scanner of FIG. 23.

In accordance with an exemplary embodiment shown in FIGS. 19 to 25, it is advantageous to mechanically link the collimator 3 and the arrays 8 with an arm 50 that pivots about a point in space parallel to the focal spot of the x-ray source 1. The collimator 3 is attached to the arm 50 in a position so that it rotates on the circumference of a circle that lies in a plane intersecting the x-ray source 1 focal spot with a center that is also located at the focal spot of the x-ray source 1. The arrays 8 are mounted on a second arm 52 that is attached and perpendicular to the end of arm 50 opposite the pivot point 51 so that, together, the two arms 50, 52 are approximately L-shaped. The second support arm 52 is curved facing the focal spot of the x-ray source 1 with a radius equal to the distance to the focal spot of the x-ray generator 1. In this manner, the arm 50 can be rotated about its pivot point 51 to produce a set of scanning x-ray beams 5 that will remain in alignment with and perpendicular to the arrays 8 mounted on the support arm 52 at all times during a scan. In this way, during a scan, the arm 50 is rotated so that the collimator 3 and arrays 8 sweep vertically to expose a person or object standing on the platform while the x-ray source 1 remains stationary as shown in the progression of FIGS. 19, 21, and 23 or 20, 22, and 24. Various portions of the x-ray source are eliminated for reasons of clarity A person standing on the platform 21 with their back against the front wall 1900 of the imaging cabinet 31 would have their feet project out in front of the wall 1900 by at least a foot and, possibly, sixteen inches. To acquire an image that would include the feet of such a person, it is necessary to bring the scanning arm 52 down below the height of the platform 21 so that the lowest x-ray beam 5 can expose the person's feet. Such an orientation is illustrated in FIGS. 23 and 24. In this exemplary embodiment, even if the support arm 52 was brought down until it touched the floor as shown, the platform 21 would have to be at least 11 inches high in order to provide enough clearance for the support arm 52 to reach far enough below the platform to scan 16 inches in front of the imaging cabinet 31, the geometry of which is illustrated in FIG. 25.

If a person to be scanned was sitting in a wheelchair, the platform 21 would have to be raised even higher. In such a situation, forward parts of the seated person might be located twenty-four or more inches away from the wall 1900. This presents a problem with the overall height and area that the system of FIGS. 19 to 25 would occupy and is a significant limitation of this exemplary embodiment because, according to most rules regarding wheelchairs, a wheelchair ramp 20 must be at least twelve inches long for every inch of height. Accordingly, a ramp for an eleven-inch platform height would have to be eleven feet long. If the platform 21 is even higher to accommodate a person in a wheelchair, the ramp 20 would be significantly longer than eleven feet, which is costly and, in many cases, architecturally problematic. Another limitation of this exemplary embodiment is that the mechanical arm 50 blocks access along one side of the platform 21. This configuration, in particular, requires people to enter and leave the platform from the same side.

Figure 26:
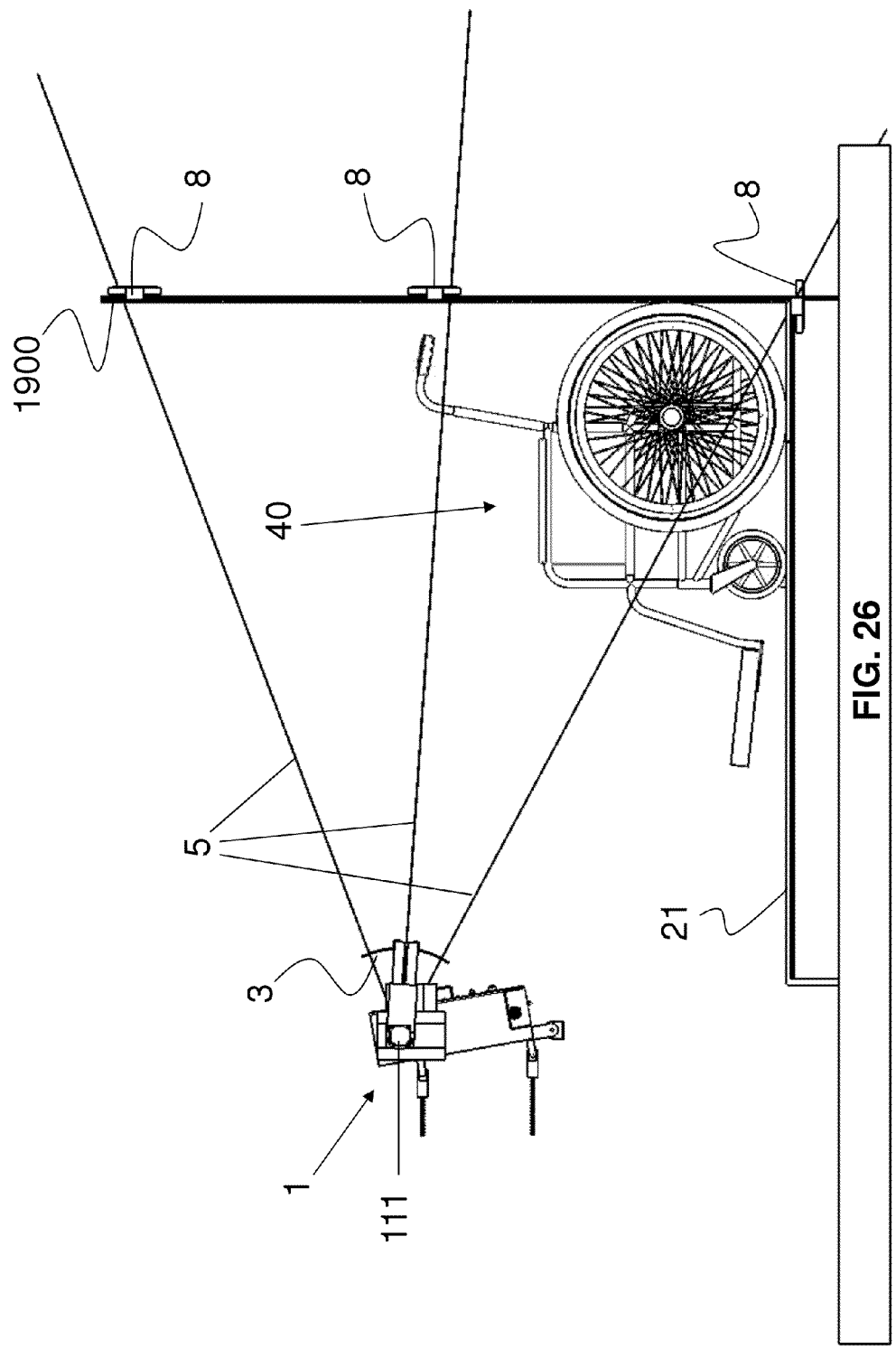
FIG. 26 is a side elevational view of an exemplary embodiment of a multi-linear x-ray scanner with a portion of the generator cabinet removed and with a collimator and a detector array sub-assembly in a raised position scanning a wheelchair.
Figure 27:
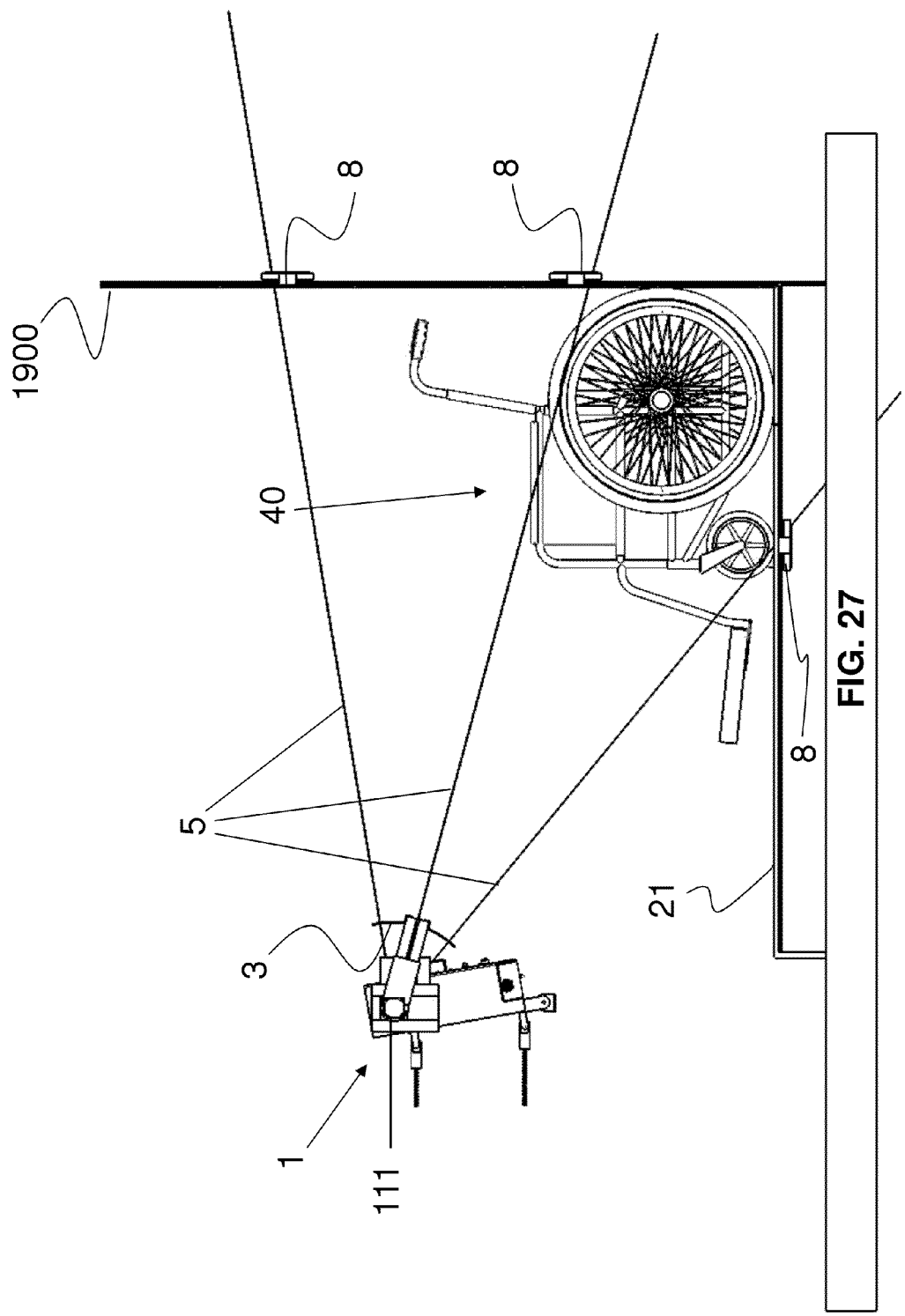
FIG. 27 is a side elevational view of the multi-linear x-ray scanner of FIG. 26 with the collimator and the detector array sub-assembly in an intermediate position.
Figure 28:
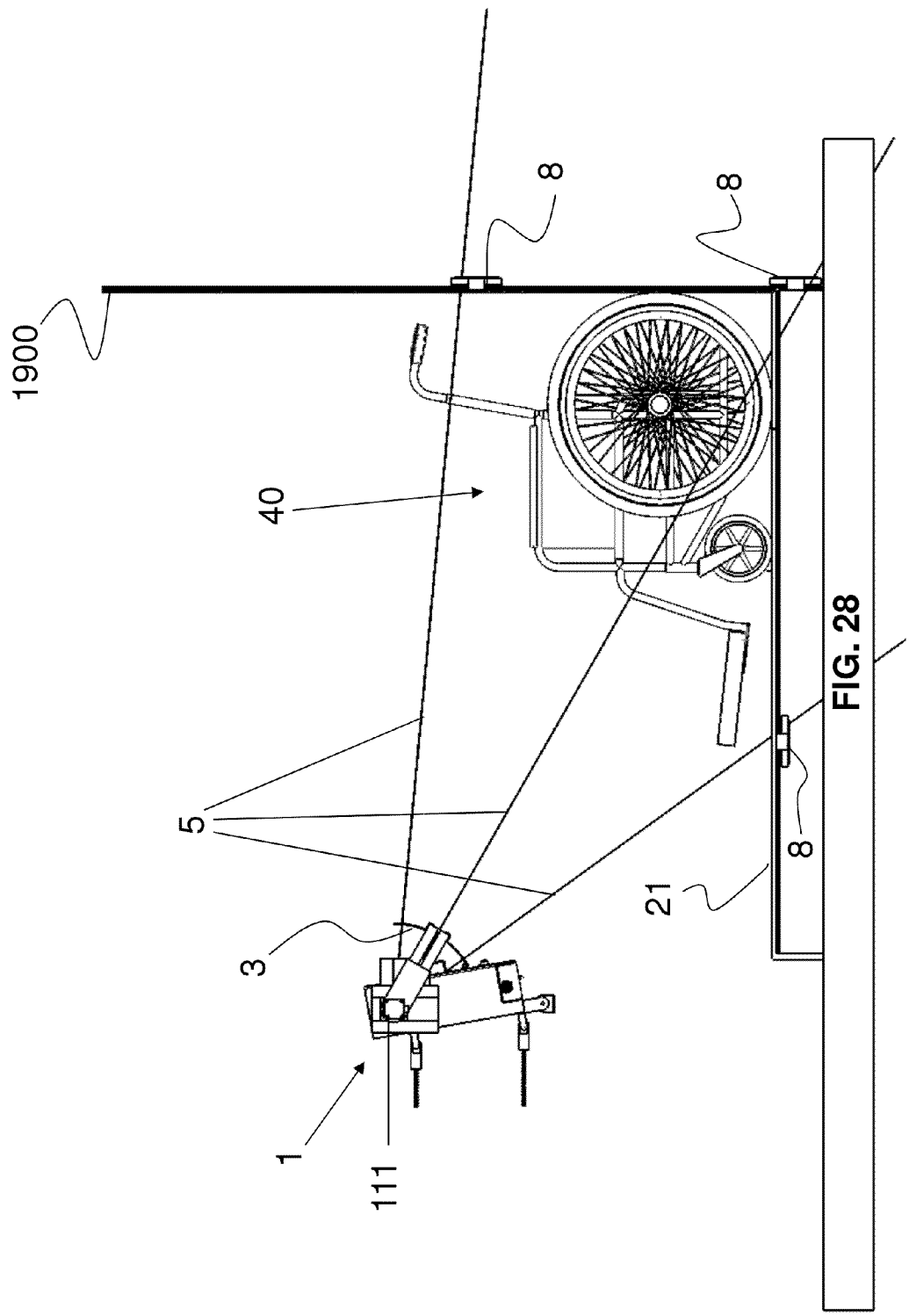
FIG. 28 is a side elevational view of the multi-linear x-ray scanner of FIG. 26 with the collimator and the detector array sub-assembly in a lowered position.
Figure 29:
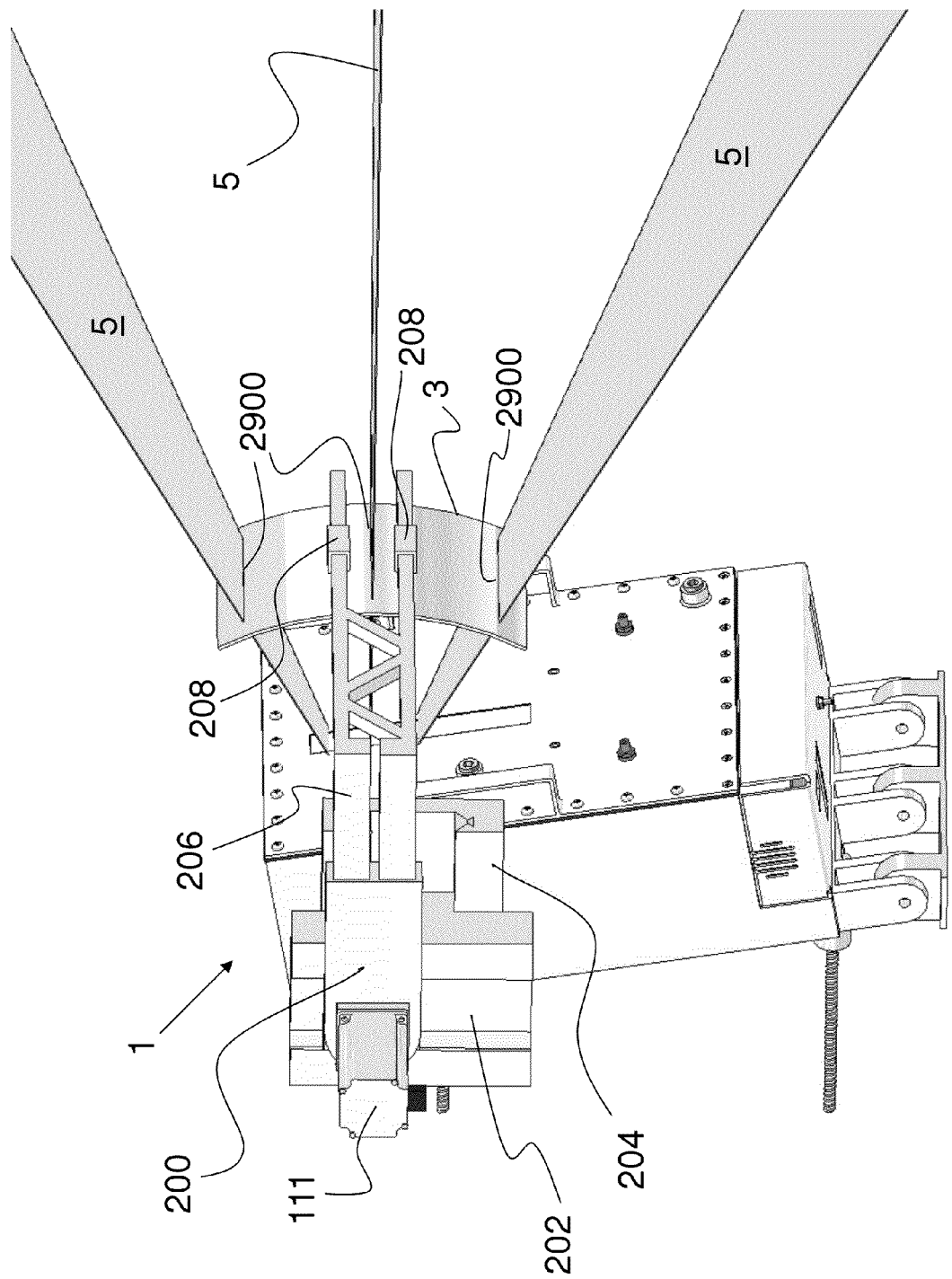
FIG. 29 is a fragmentary, enlarged, perspective view of a portion of the generator cabinet of FIG. 26 from a front side thereof.
Figure 30:
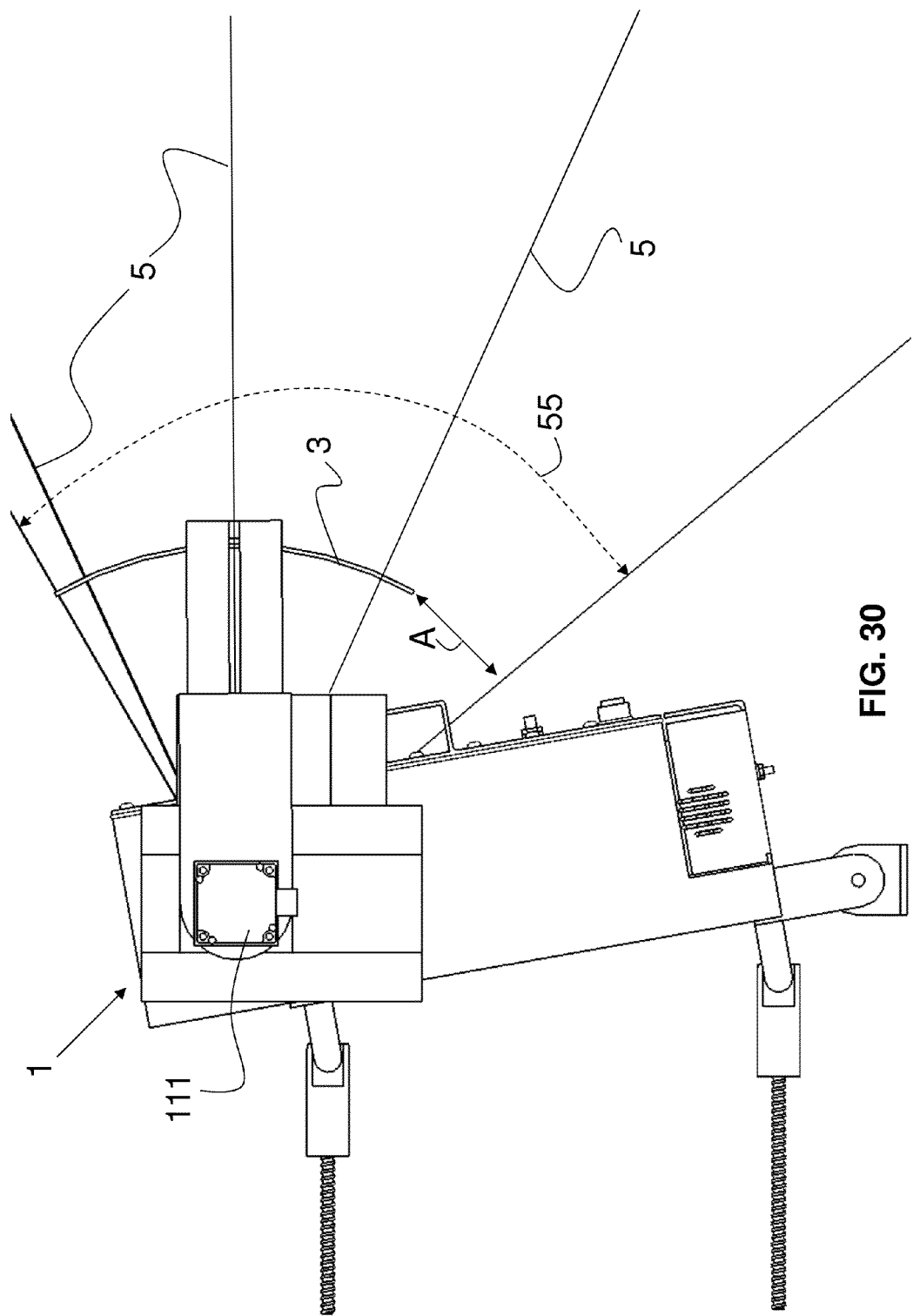
FIG. 30 is a fragmentary, enlarged, side elevational view of the portion of the generator cabinet of FIG. 29 from a right side thereof with the collimator in a raised position.
Figure 31:
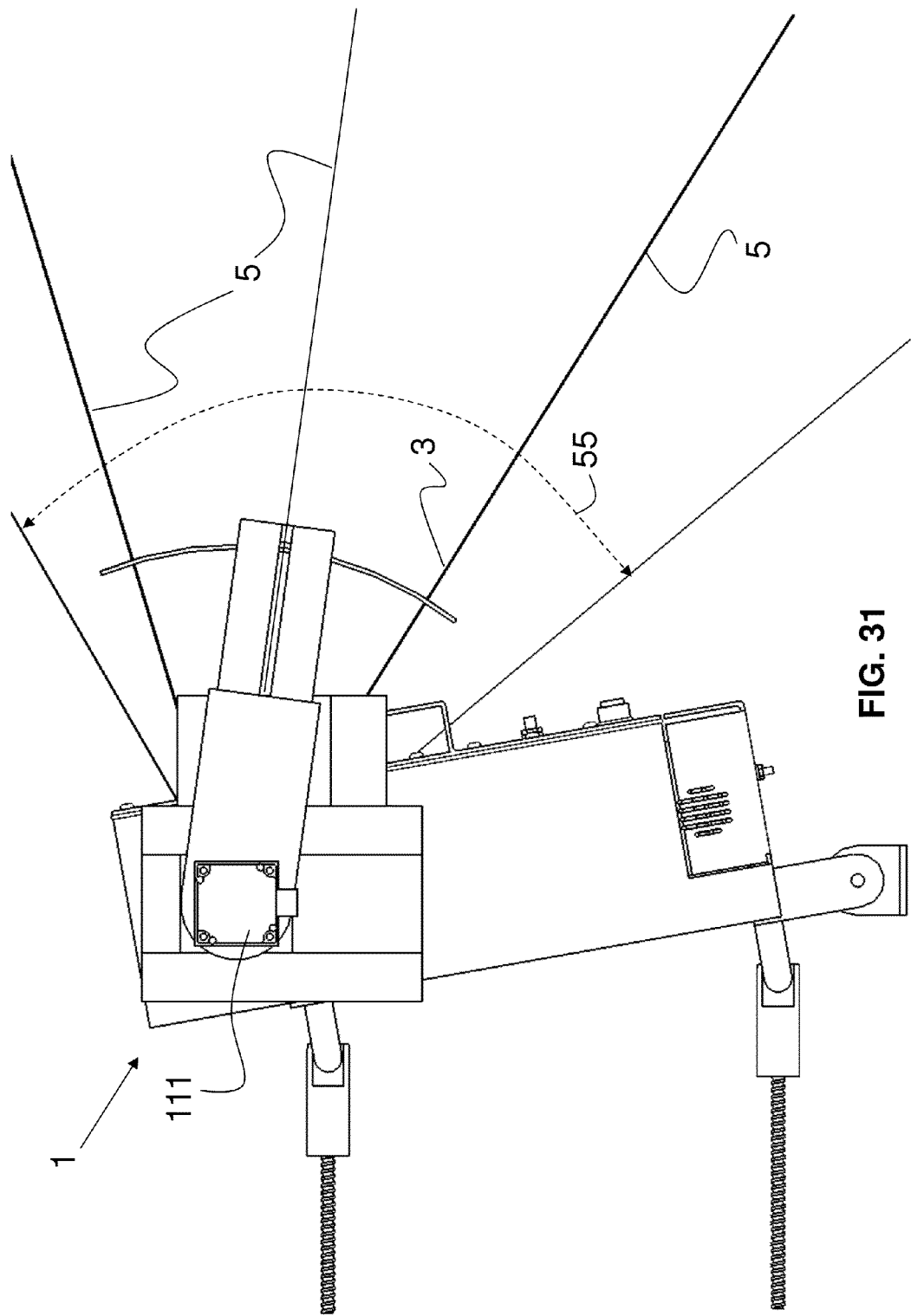
FIG. 31 is a fragmentary, enlarged, side elevational view of the portion of the generator cabinet of FIG. 29 from a right side thereof with the collimator in an intermediate position.
Figure 32:
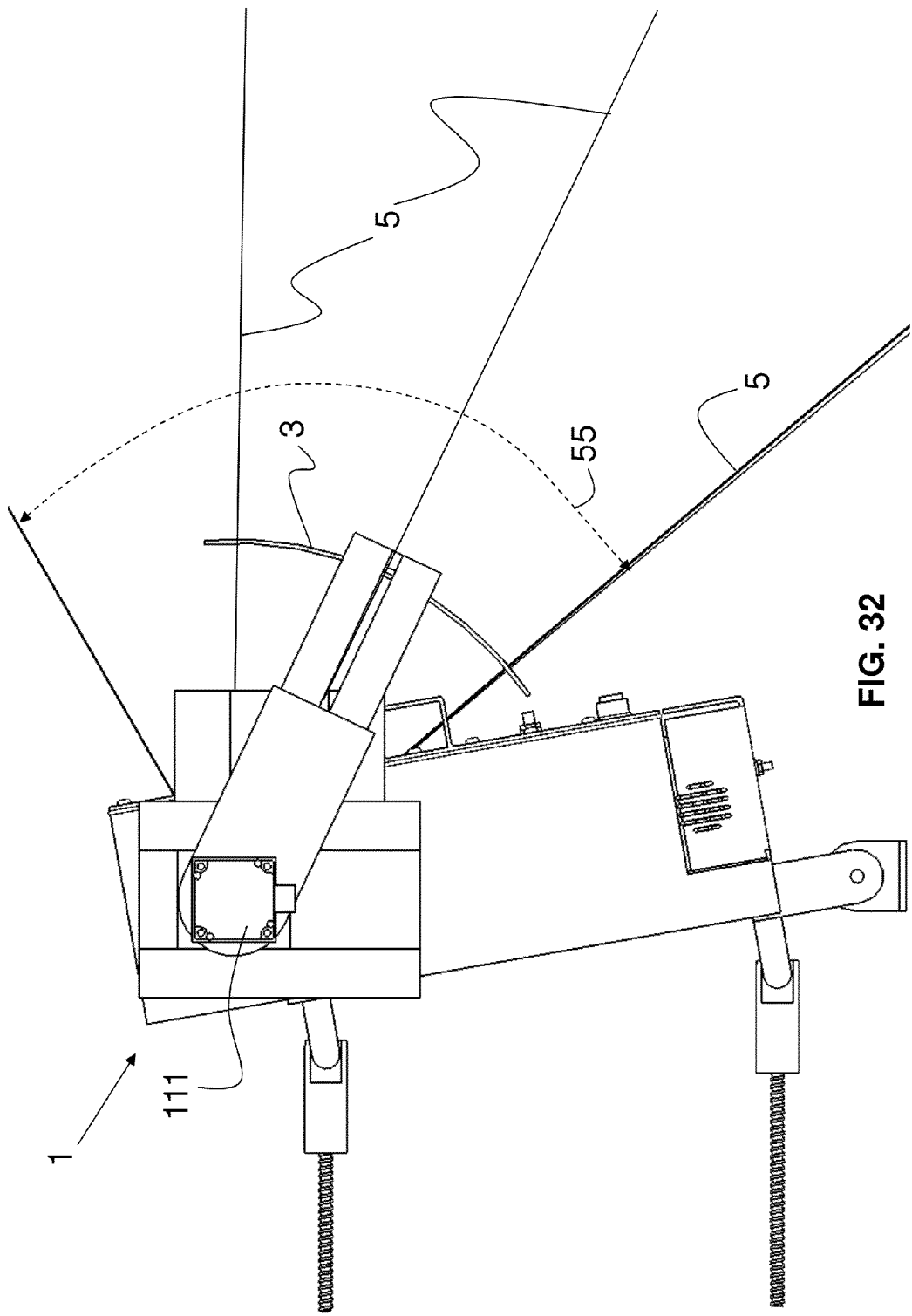
FIG. 32 is a fragmentary, enlarged, side elevational view of the portion of the generator cabinet of FIG. 29 from a right side thereof with the collimator in a lowered position.
Figure 33:
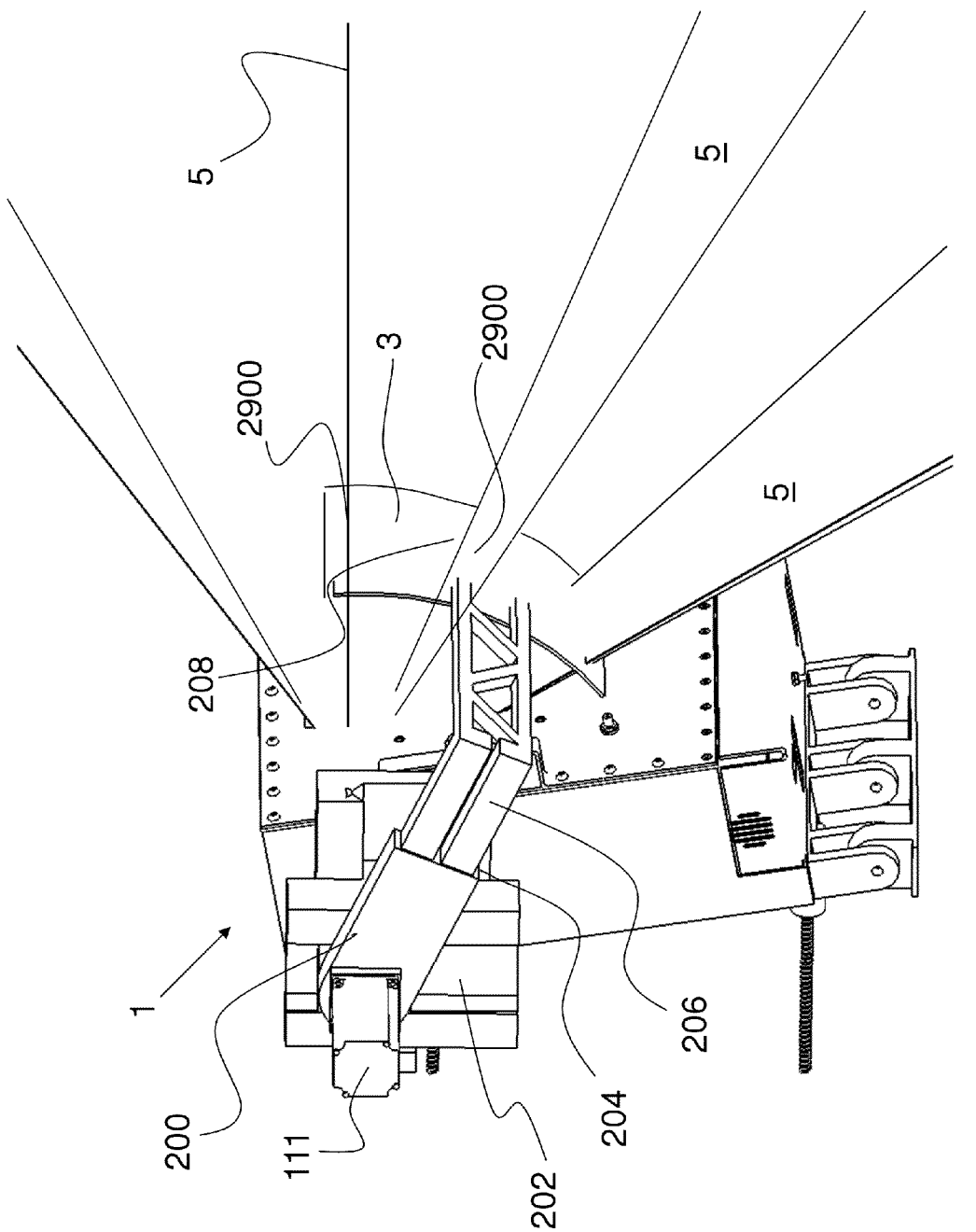
FIG. 33 is a fragmentary, enlarged, perspective view of the portion of the generator cabinet of FIG. 32 from in front the right side thereof.

In order to scan people sitting in wheelchairs 40, therefore, another exemplary embodiment of the system scans along the underside of the platform 21 in addition to the front wall 1900 of the imaging cabinet 31. In accordance with this exemplary embodiment shown in FIGS. 26 to 40, the detector arrays 8 are mounted on a set of horizontal rails—two of the arrays 8 being mounted behind the 1900 wall of the imaging cabinet 31 and one array 8 being mounted under the platform 21. Each of the three arrays 8 are driven by separate drive motors 11. The position of each array 8 is measured by separate encoders 10. In this configuration, the mechanical arms 50 and 52 are, therefore, replaced by independently controlled motors 11 that move the arrays 8 synchronously with the x-ray beams 5 as the collimator 3 sweeps through its vertical motion. Synchronizing the motion of the arrays 8 with the motion of the x-ray beams 5 can be accomplished by a feedback mechanism where the output of one or more of the photodiodes 9 on the extreme ends of each array 8, for example, are used to control the motion of each of the arrays by adjusting the speed of each drive motor 11 so that the intensity of the output from the photodiodes 9 is maintained at a maximum value during the scan. Alternatively, a set of sentinel photodiodes 9 are mounted directly above and below each of the arrays 8 to sense the x-ray beams 5. If any of the arrays 8 moves out of alignment with their respective x-ray beams 5, the sentinel diodes 9 will begin to produce a signal that can be used to speed up or slow down the drive motor 11 and keep the array 8 moving synchronously with the x-ray beams 5. FIGS. 26 to 28 show the progression of the x-ray beams 5 as they move from above a person in a wheelchair to below.

In this exemplary embodiment, the collimator 3 has a plurality of slit openings 300, is mounted to the x-ray source 1 with an adjustable mounting bracket 200 and is rotated with a drive motor 111. These features are shown in the enlarged view of the x-ray source 1 in FIGS. 29 to 33. The mounting bracket 200 has two adjustable slides 202 and 204 to align the collimator 3 with the focal spot of the x-ray source 1. The mounting bracket 200 also has an L-shaped bracket 206 that is rotated by drive motor 111 to hold and position the collimator 3 in alignment with the focal spot of the x-ray source 1.

The collimator 3 has a set of slots 2900 shaped to emit the x-ray beams 5 and adjustment assemblies 208 that allow it to slide back and forth along the L-shaped bracket 206 so that it can be aligned with the focal spot of the x-ray source 1. Once alignment has been achieved, the collimator 3 can be fixed in place with set screws. The collimator 3 defines emission slots 290 for emitting the x-ray beams 5.

Figure 34:
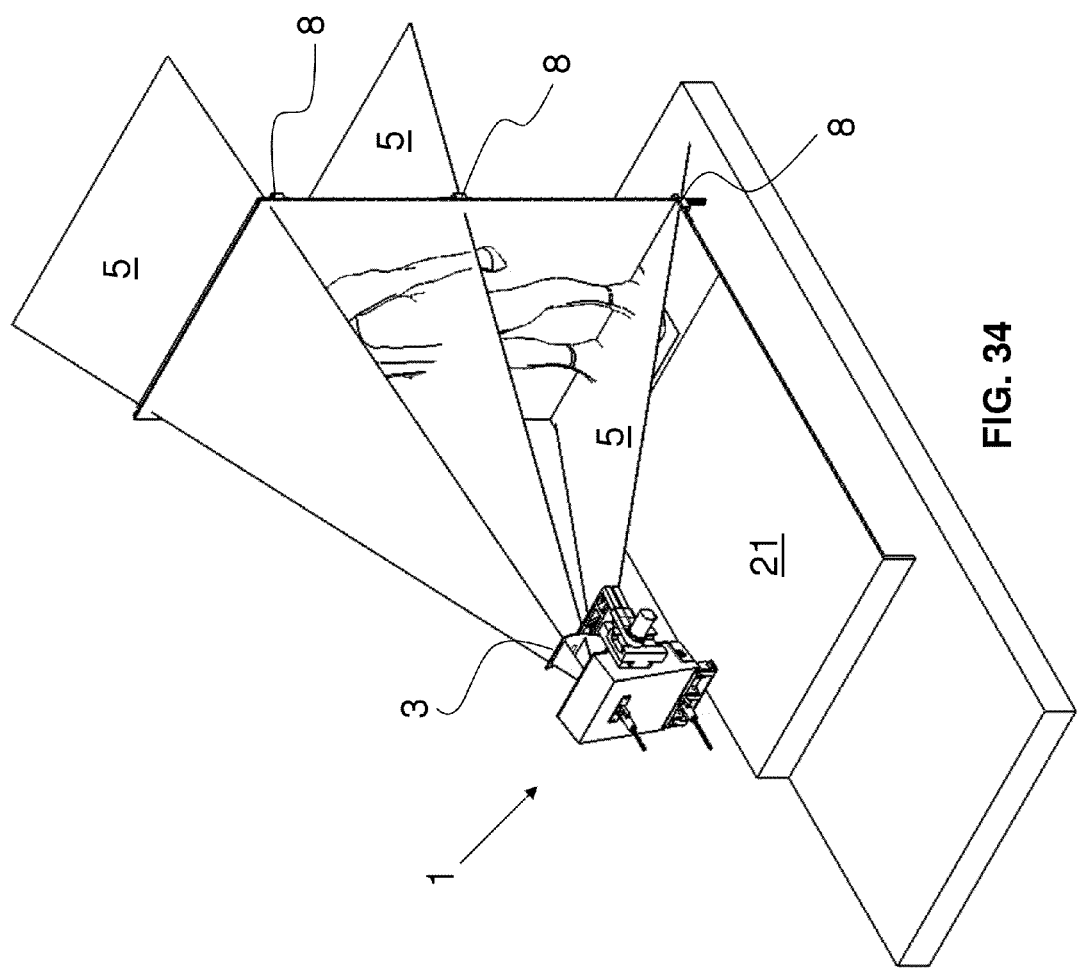
FIG. 34 is a side elevational view of the multi-linear x-ray scanner of FIG. 26 with a collimator and a detector array sub-assembly in a raised position scanning a person.
Figure 35:
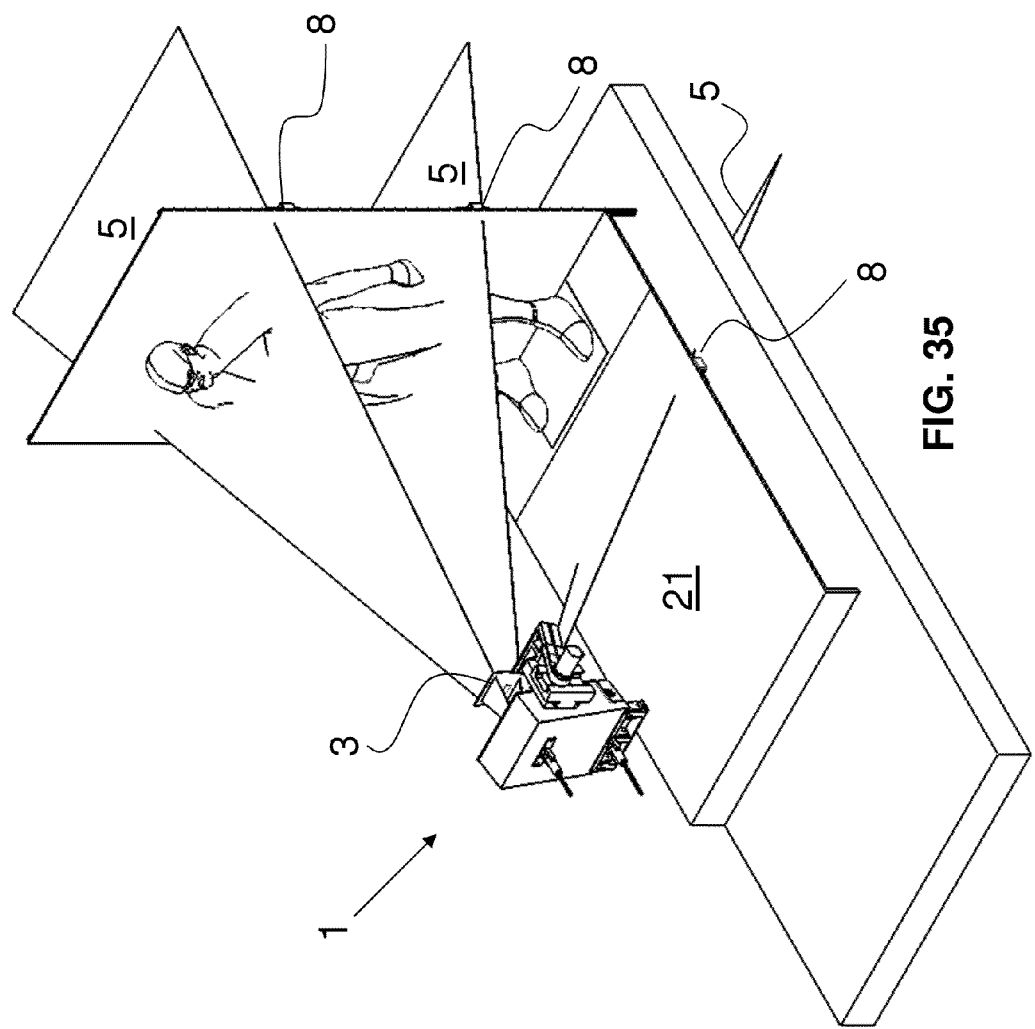
FIG. 35 is a side elevational view of the multi-linear x-ray scanner of FIG. 34 with the collimator and the detector array sub-assembly in an intermediate position.
Figure 36:
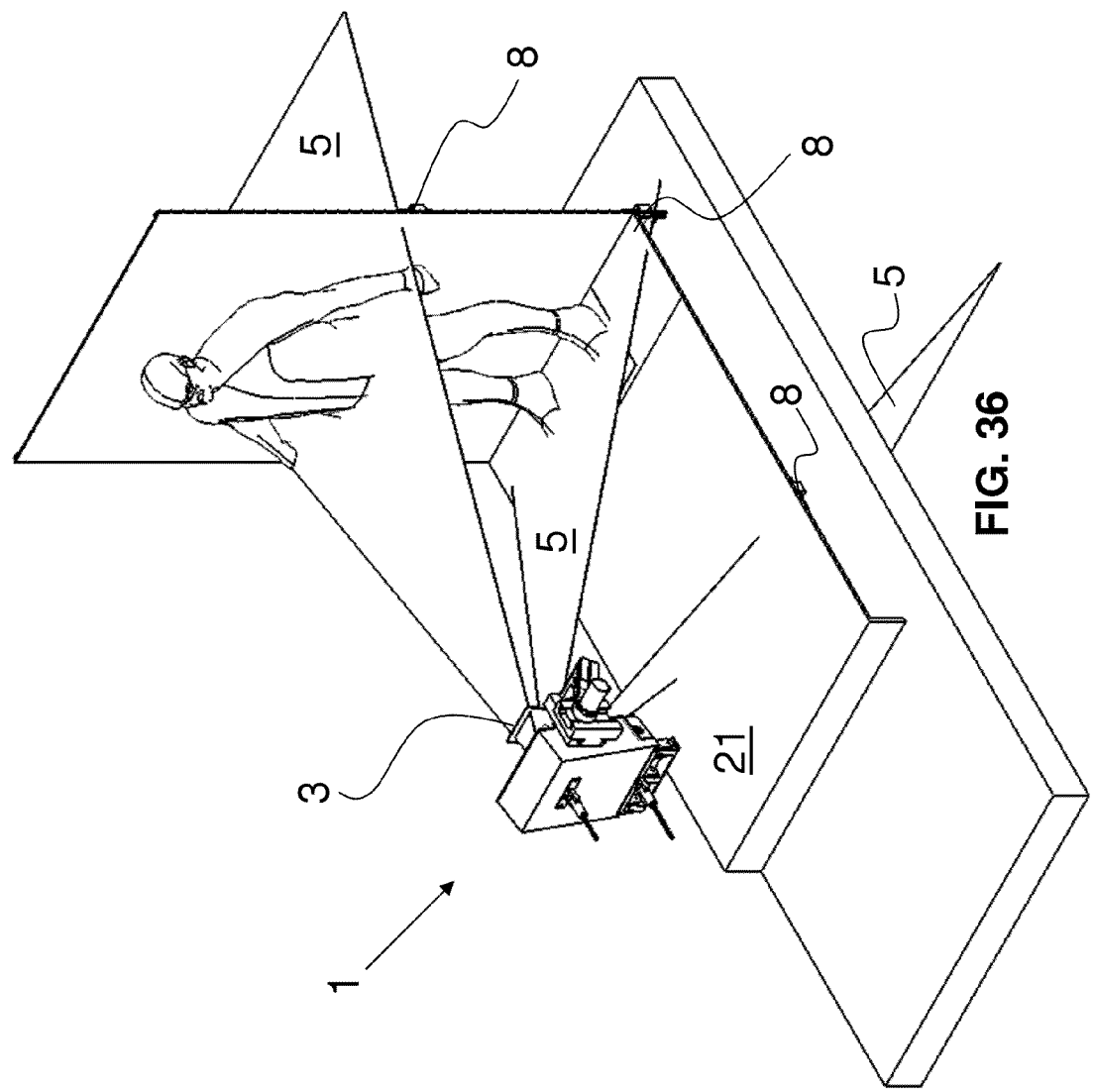
FIG. 36 is a side elevational view of the multi-linear x-ray scanner of FIG. 34 with the collimator and the detector array sub-assembly in a lowered position.
Figure 37:
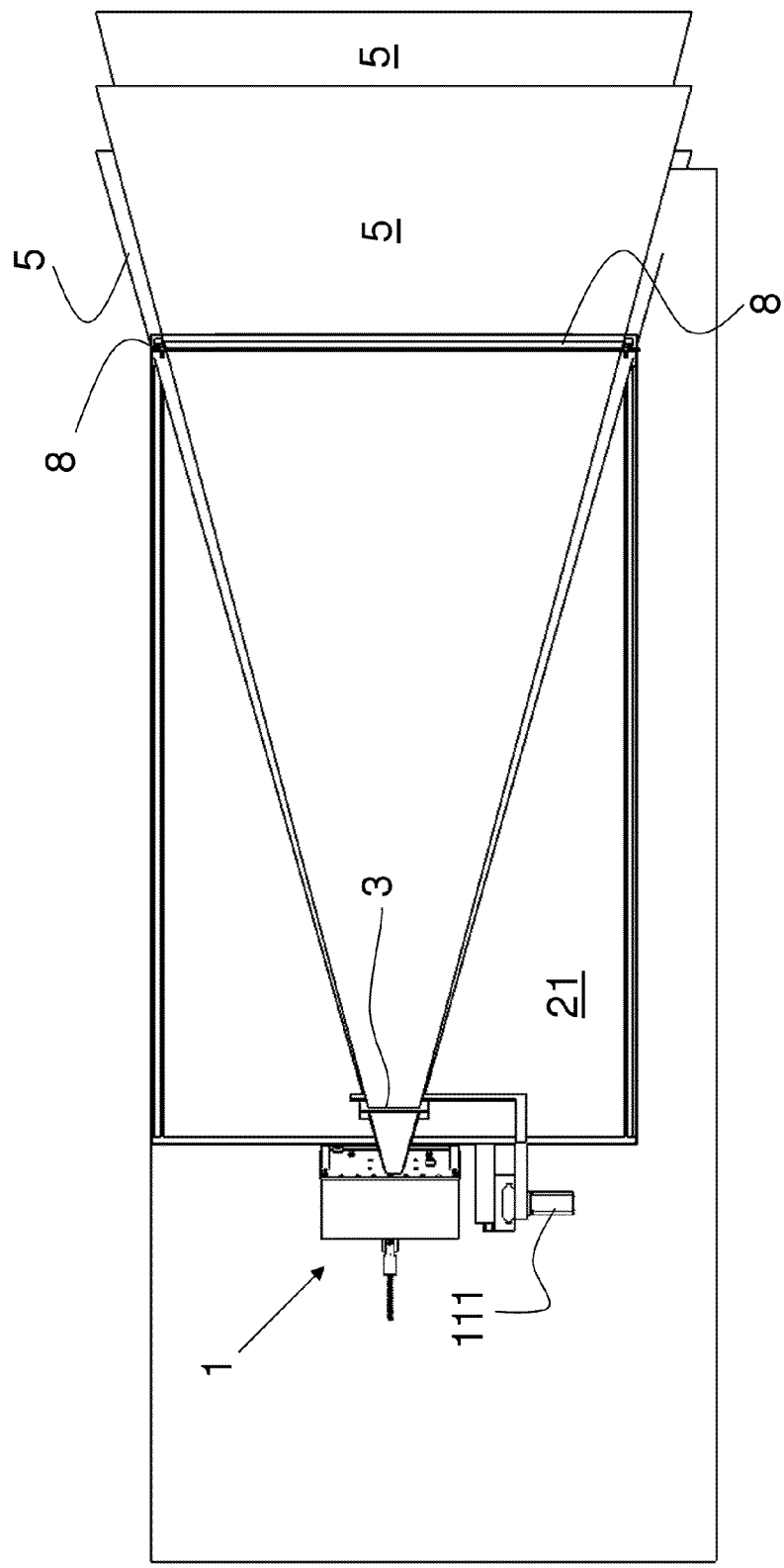
FIG. 37 is a side elevational view of the multi-linear x-ray scanner of FIG. 26 with the collimator and the detector array sub-assembly in a raised position.
Figure 38:
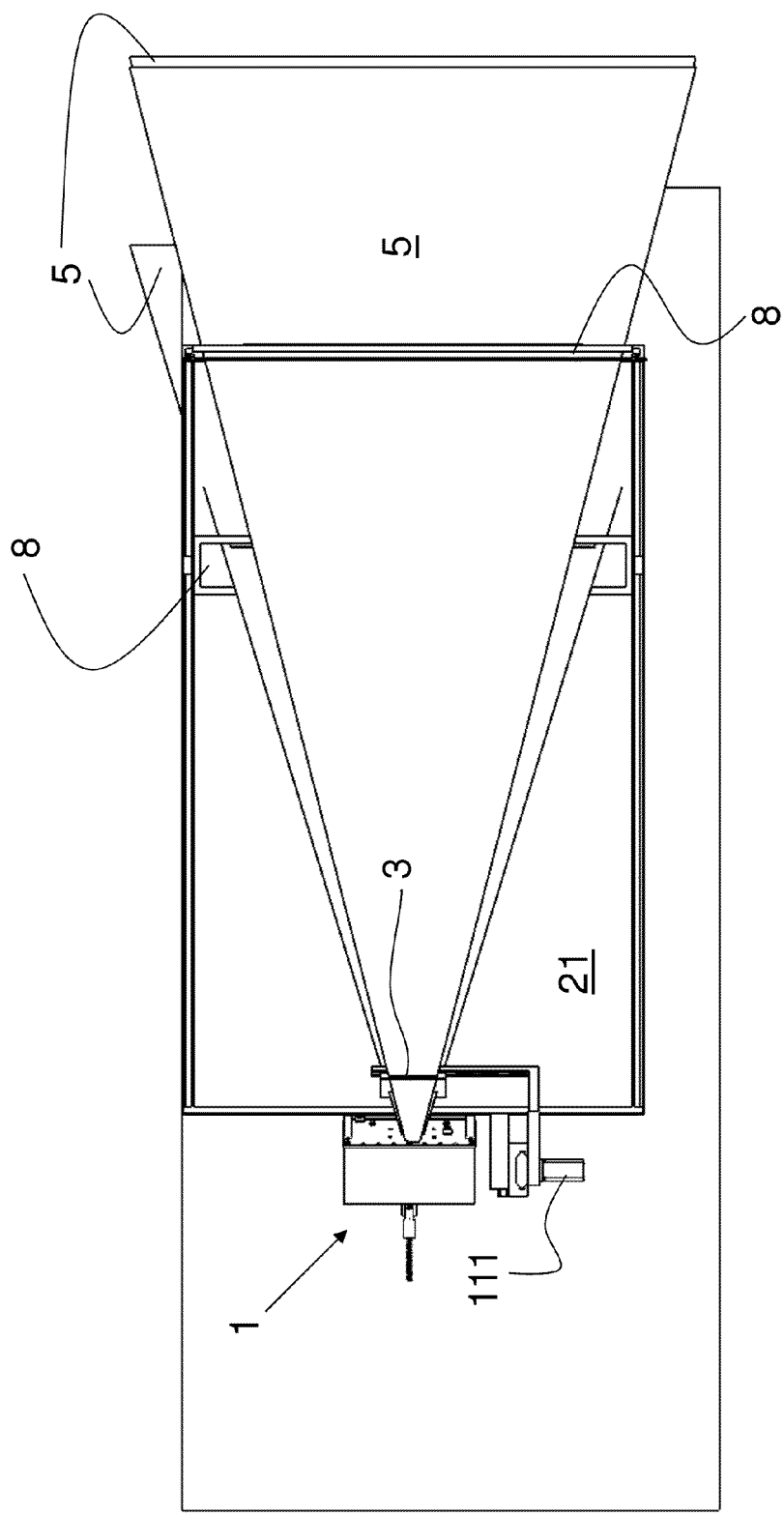
FIG. 38 is a side elevational view of the multi-linear x-ray scanner of FIG. 37 with the collimator and the detector array sub-assembly in an intermediate position.
Figure 39:
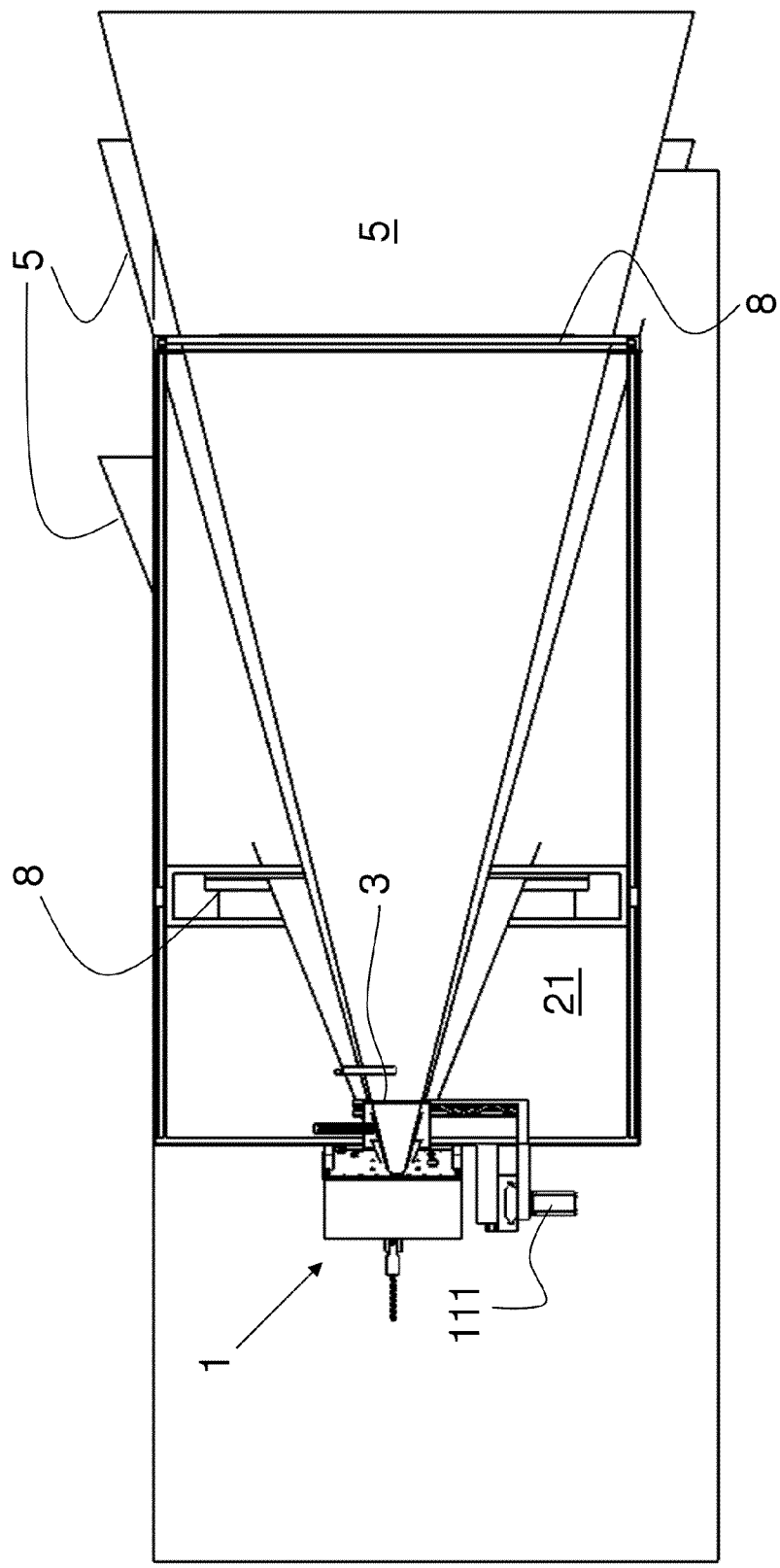
FIG. 39 is a side elevational view of the multi-linear x-ray scanner of FIG. 37 with the collimator and the detector array sub-assembly in a lowered position.
Figure 40:
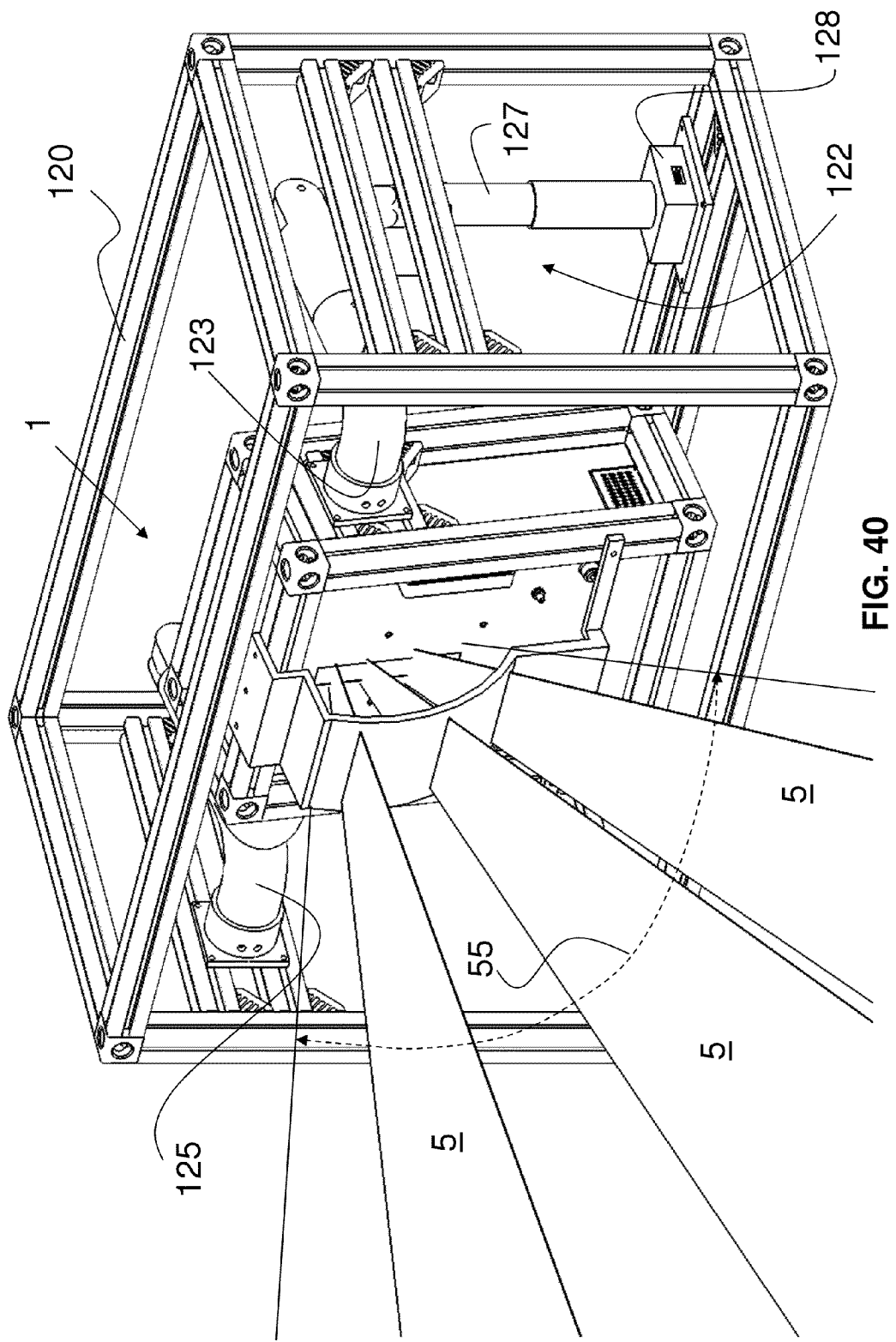
FIG. 40 is a fragmentary, perspective view of an exemplary embodiment of a multi-linear x-ray scanner from a front side thereof with a portion of the generator cabinet removed and with a collimator pivoted to an intermediate position.
Figure 41:
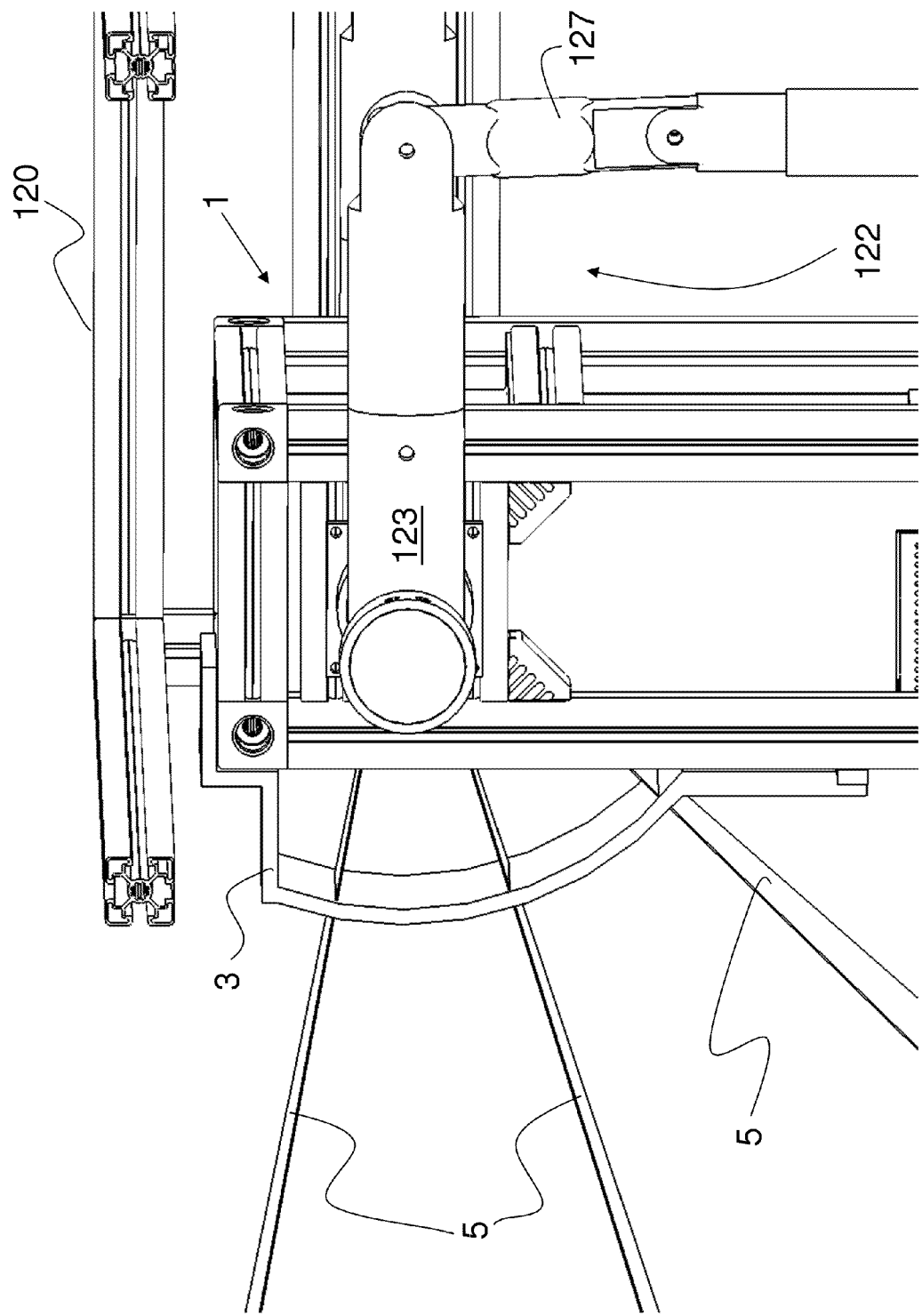
FIG. 41 is a fragmentary, partially cross-sectional, perspective view of the multi-linear x-ray scanner of FIG. 40 from behind a side thereof.

There are a number of embodiments of the system 1 that are possible using a fixed x-ray source 1 with a moving collimator 3 to produce one or more scanning x-ray beams 5 and with one or more arrays 8. These embodiments include synchronization of the scanning x-ray beams 5 and the arrays 8 by mechanical linkage (using mechanical arms 50 and 52) and synchronization by microprocessor control using, for example, a feedback signal from the arrays 8 or sentinel diodes 9 to keep the detectors in the arrays 8 in alignment with the x-ray beams 5 during the scan. To acquire images of people sitting in wheelchairs 40, it is necessary to scan in two perpendicular planes (a vertical plane behind the person and a horizontal plane beneath them) in order to completely cover the entire volume of space they occupy. In these embodiments, the x-ray source 1 has an x-ray emission cone 55 that is at least 80 degrees high by 30 degrees wide in order to cover a volume in the scanning booth large enough to image a person sitting in a wheelchair 40. The x-ray source 1 is placed approximately 2.2 meters from the arrays 8 and the total length of the scanned image is at least 1.1 meters horizontally (under the platform 21) and 2.2 meters vertically (behind the front wall 1900 of the imaging cabinet 31). An exemplary embodiment of this is shown in FIGS. 26 through 33. As shown, the x-ray source 1 is fixed and the collimator 3 is rotated by the motor 111 to sweep three of the x-ray beams 5 to scan an "L-shaped" area that is tracked by a set of three arrays 8 in the form of photodiodes to obtain an image of a person sitting in a wheelchair 40 on a platform 21. FIGS. 34 through 36 show this same embodiment scanning a person standing on the platform 21. FIGS. 37 through 39 show the progression of the scan of this exemplary embodiment without a person or a wheelchair present from above the system 1 and the array 8 below the platform 21 is shown moving from the rear to the front of the system 1.

The embodiments described above that incorporate a fixed x-ray source 1 and moving collimator 3 have a limitation that must be overcome with additional shielding components in the aperture 4 of the generator cabinet 30. This problem is illustrated in FIGS. 29 through 33. As shown in these figures, the x-ray emission cone 55 is intercepted by the moving collimator 3 as it moves up and down to create the scanning x-ray beams 5. The shape of the moving collimator 3 and its slit openings 300 are determined by the distance of the collimator 3 from the focal spot of the x-ray generator 1. The collimator 3 must have a curved surface whose radius is equal to the distance from the collimator 3 to the focal spot of the x-ray generator 1 and must move along an arc whose radius is also equal to the distance to the focal spot. It is advantageous to keep the distance from the collimator 3 to the focal spot small to reduce the weight and size of the collimator 3 and to reduce the length of travel that the collimator 3 must go through to scan the entire length required. If the x-ray source 1 is a mono-block generator, the size and shape of the generator prevents the collimator 3 from completely blocking the entire x-ray emission cone 55 during the scan. As shown in FIGS. 29 through 33, the emission cone 55 of the x-ray source 1 extends above and below the position of the collimator 3 as it scans through the image. See, for example, arrow A in FIG. 30. The arc length of the collimator 3 must be kept short to prevent it from colliding with the x-ray source 1 at the top and bottom of the scan. The portion of the x-ray emission cone 55 that extends laterally on both sides of the collimator 3 can be blocked by the aperture 4 in the front of the x-ray generator cabinet 30. To prevent x-rays in the emission cone 55 that are not blocked by the collimator 3 from escaping from the generator cabinet 30, a set of lead blades is incorporated in the aperture 4 to intercept the unblocked x-rays. These lead blades move up and down while the collimator 3 is scanning. Alternatively, the collimator 3 has to be moved farther away from the x-ray source 1 so that the arc length of the collimator 3 can be extended enough to block the entire emission cone 55 and not come in contact with the x-ray source 1 at the top and bottom of the scan. Doing this, however, increases the size and weight of the collimator 3 and increases the arc length the collimator 3 has to travel to complete the scan.

If the x-ray source 1 was configured as a separate x-ray generator and x-ray tube, it is possible to make a collimator 3 with a sufficiently large arc length to block the radiation in the emission cone 55 both above and below the collimator 3 through its entire scan while keeping the size and position of the collimator 3 small and compact. This is due to the smaller size and shape of an x-ray tube compared with a mono-block generator. The cylindrical shape of the x-ray tube is ideal for keeping the size and position of the collimator 3 small and compact. This reduces the size and cost of the drive motor 111 for the collimator 3. An exemplary embodiment of the system 1 with an x-ray tube is shown in FIGS. 57 to 68.

Another limitation of the fixed-x-ray-source/moving-collimator embodiments herein is that the precision required to keep the motion of the collimator 3 in synchronization with the motion of the arrays 8 is very exacting. Because the collimator 3 is only about 10 percent of the distance that the arrays 8 are from the focal spot of the x-ray source 1, the precision of its travel must be 100-times greater than that of the arrays 8. In the embodiment where a mechanical arm 50 is used to keep the collimator 3 and arrays 8 aligned during the scan, this is not a problem. In the microprocessor controlled embodiment of the scanner geometry, in comparison, the problem of the precision scanning is present although it removes the problem of blocking one side of the scanning platform 21 that the mechanical arm 50 presents. One way to mitigate the precision scanning problem and avoid needing a mechanical linkage between the collimator 3 and arrays 8 is to fix the collimator 3 to the x-ray source 1 and, instead of moving the collimator with respect to the x-ray source 1, move the x-ray source 1, itself, up and down to sweep the x-ray beams 5 through the scanning motion. In this fashion, because they move together, the collimator 3 always stays in alignment with the x-ray source 1 focal spot. Such an exemplary embodiment is illustrated in FIGS. 40 through 56.

FIGS. 40 to 47 show an exemplary embodiment of the system configuration where the x-ray source 1 is mounted in a frame 120 via two pivoting arm assemblies 122. The pivoting arm assemblies 122 are attached, in this exemplary configuration, to the sides of the x-ray source 1 and to the bottom of the frame 120. The pivoting arm assemblies 122 are mounted on the x-ray source 1 in line with the focal spot of the x-ray source 1. In this way, the center of rotation of the x-ray source 1 is lined up with the center of the focal spot of the x-ray source 1 so that, when the x-ray source 1 moves, it does so about the center of the focal spot. The pivoting arm assemblies 122 include Y-shaped pivot arms 123 on either side of the x-ray source 1. The Y-shaped pivot arms 123 have inside ends 124 fixedly attached to the x-ray source 1 and outside ends 125 pivotally connected to the frame 120. Opposite the ends 124, 125 is a movement end 126 pivotally connected to the distal end of a telescoping arm 127 of a drive motor 128.

Actuation of the drive motor 128 telescopes the telescoping arm 127 in and out to translate the movement end 126 and rock the Y-shaped pivot arms 123 about their pivoting axis to, thereby, move the x-ray source 1 to sweep the x-ray beams 5 emitted through the collimator 3 through the scanning area and create the x-ray emission cone 55.

Figure 42:
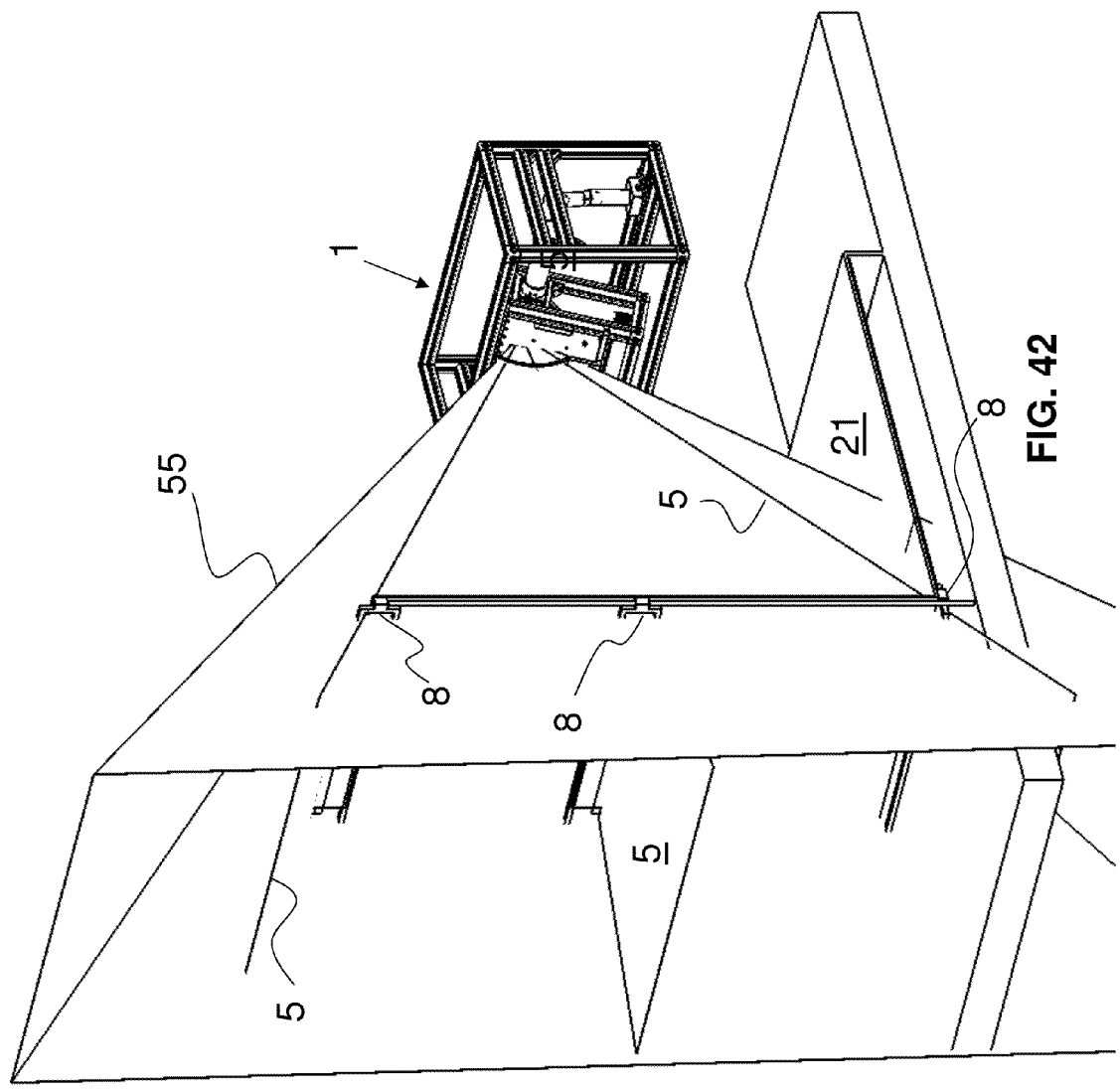
FIG. 42 is a perspective view of the multi-linear x-ray scanner of FIG. 40 with the collimator and detector arrays in a raised position.
Figure 43:
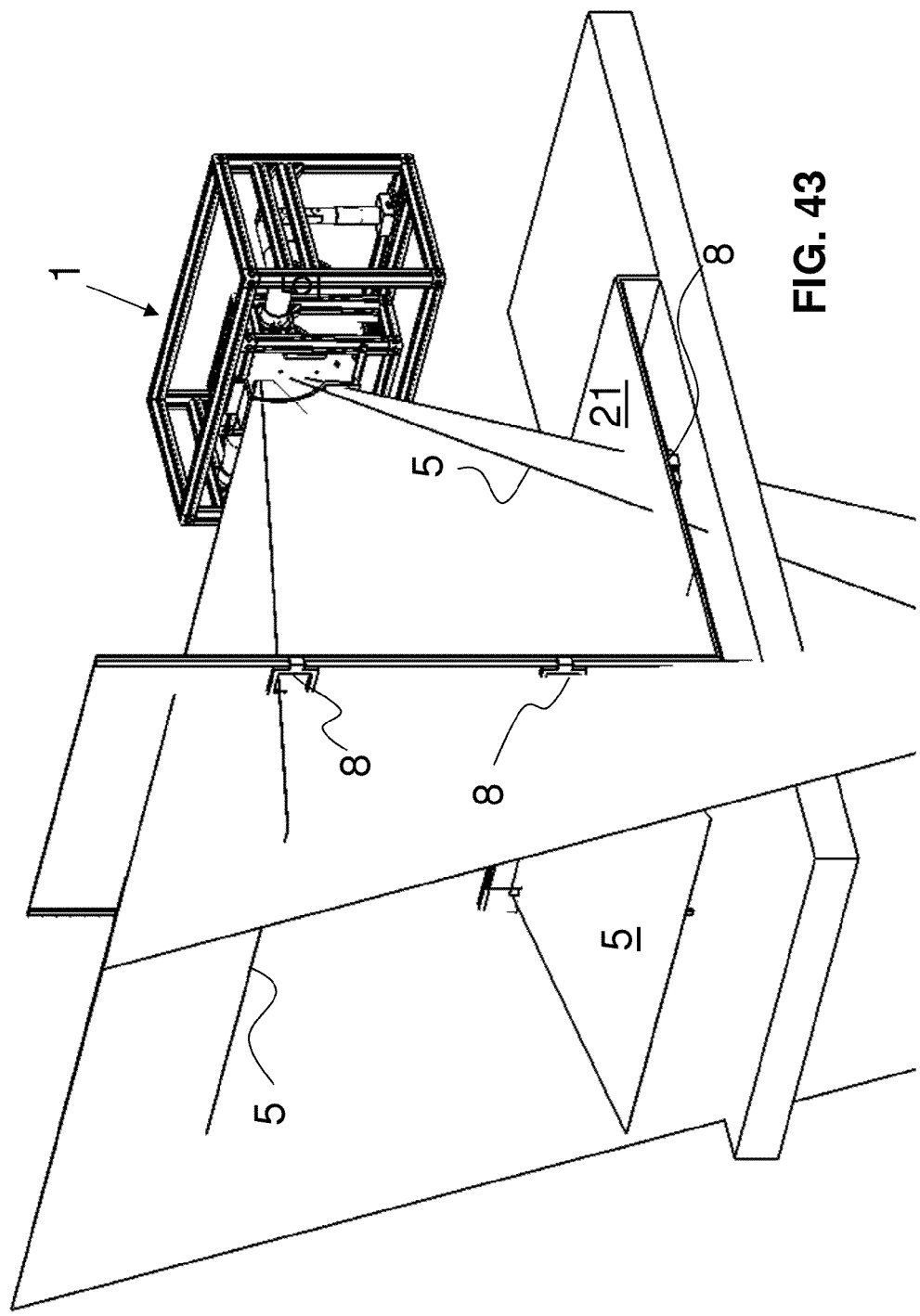
FIG. 43 is a perspective view of the multi-linear x-ray scanner of FIG. 40 with the collimator and detector arrays in an intermediate position.
Figure 44:
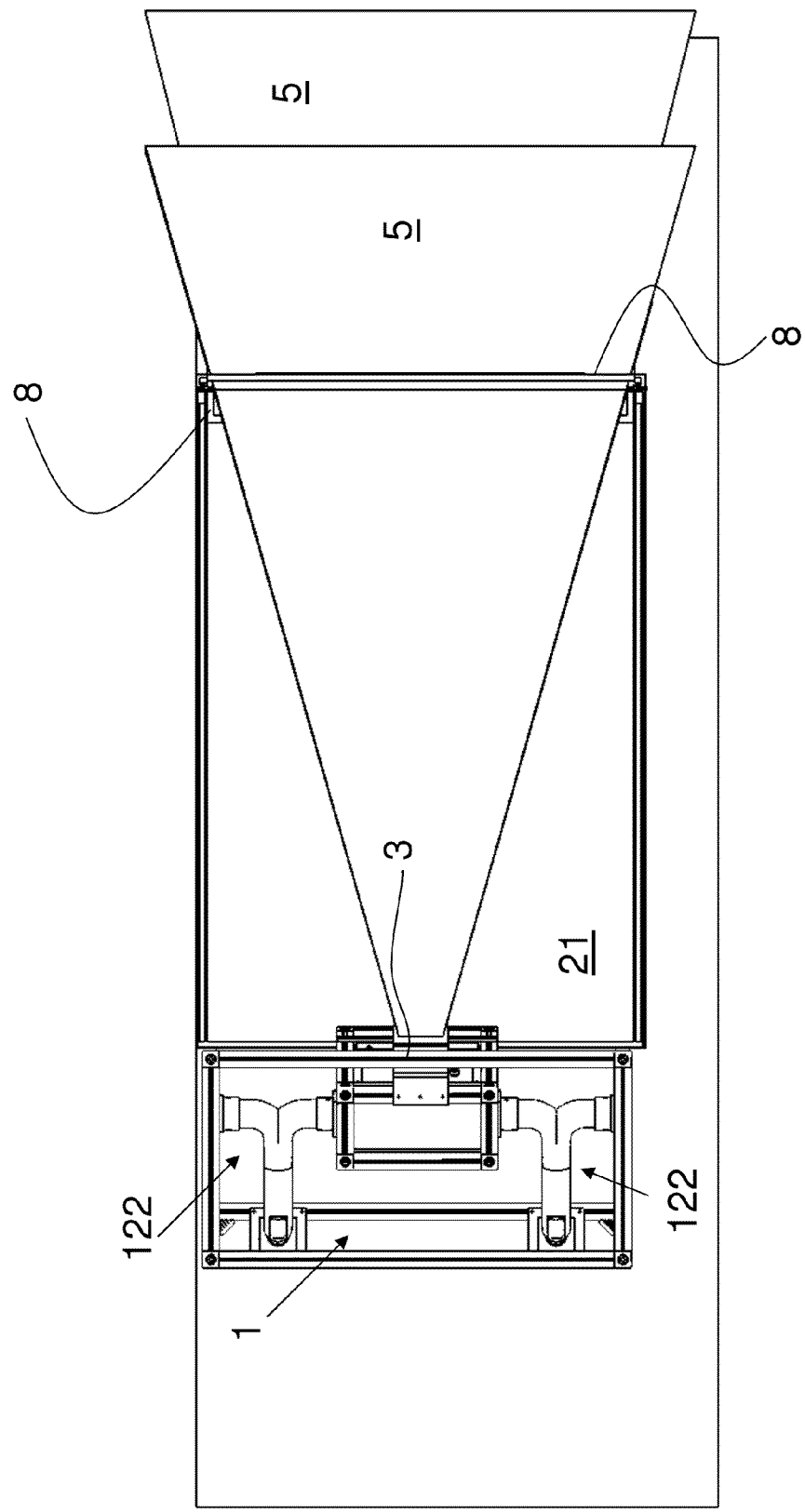
FIG. 44 is a top plan view of the multi-linear x-ray scanner of FIG. 40 with the collimator and detector arrays in a raised position.
Figure 45:
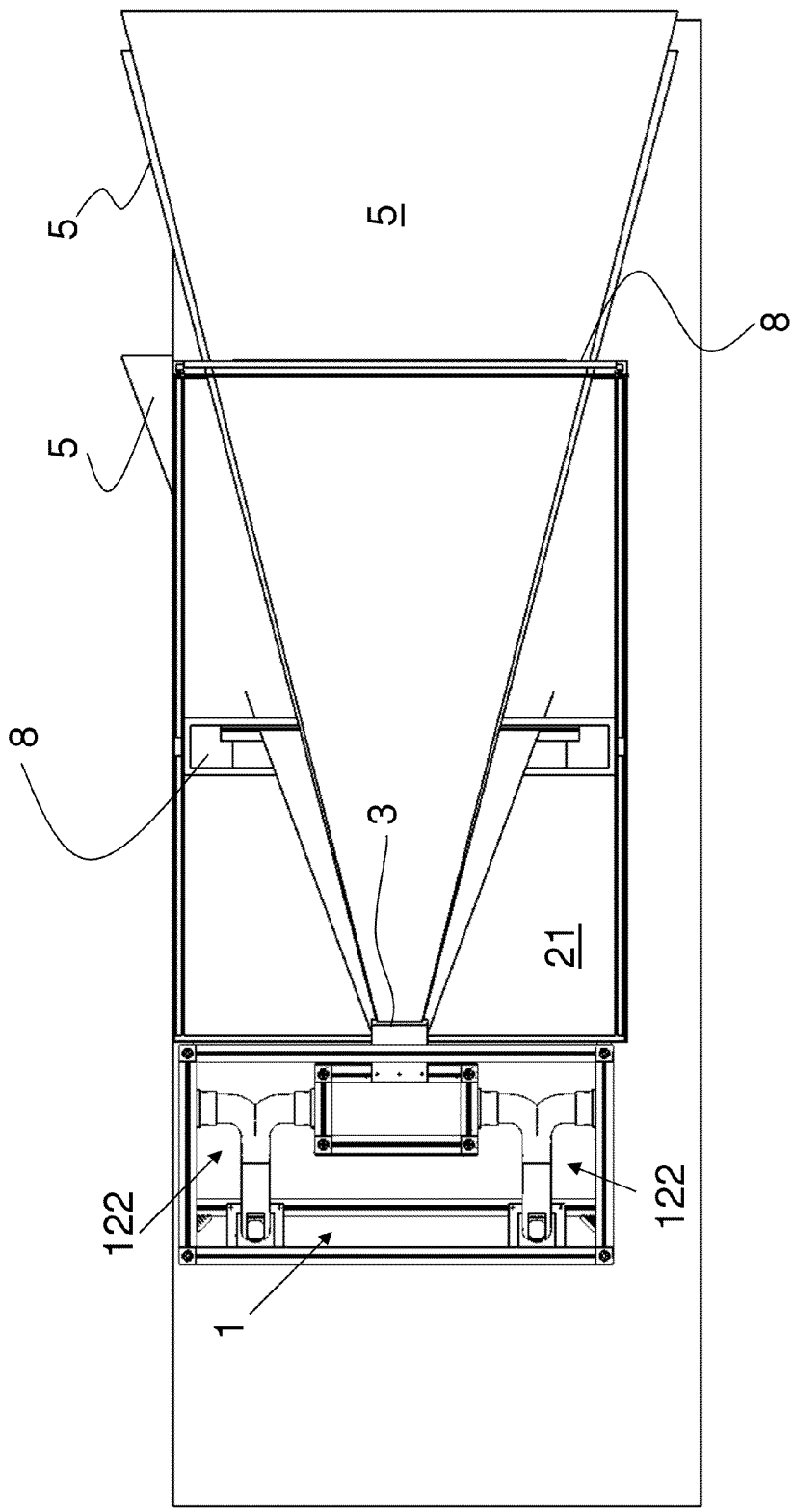
FIG. 45 is a top plan view of the multi-linear x-ray scanner of FIG. 40 with the collimator and detector arrays in an intermediate position.
Figure 46:
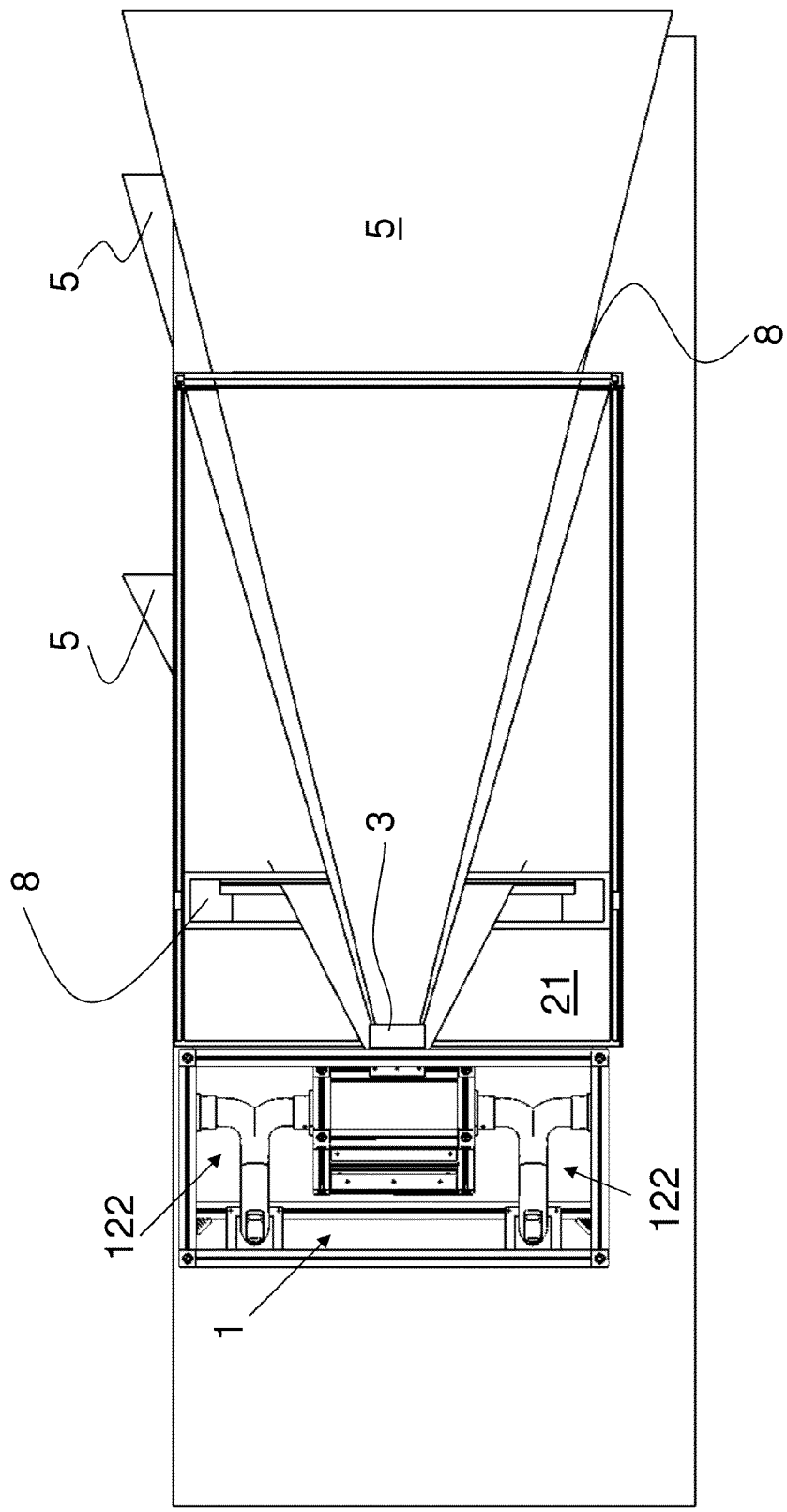
FIG. 46 is a top plan view of the multi-linear x-ray scanner of FIG. 40 with the collimator and detector arrays in a lowered position.
Figure 48:
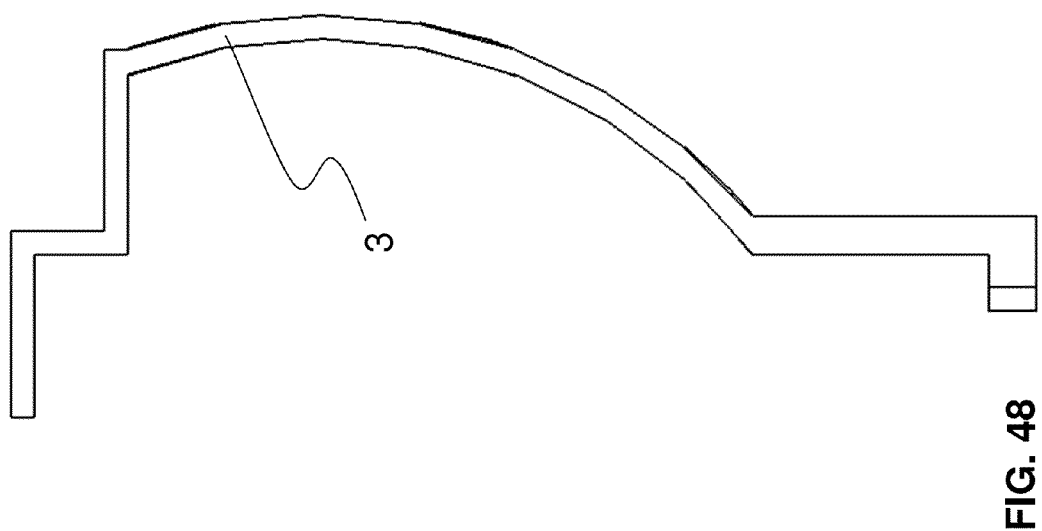
FIG. 48 is a left side elevational view of the collimator of the multi-linear x-ray scanner of FIG. 40.
Figure 47:
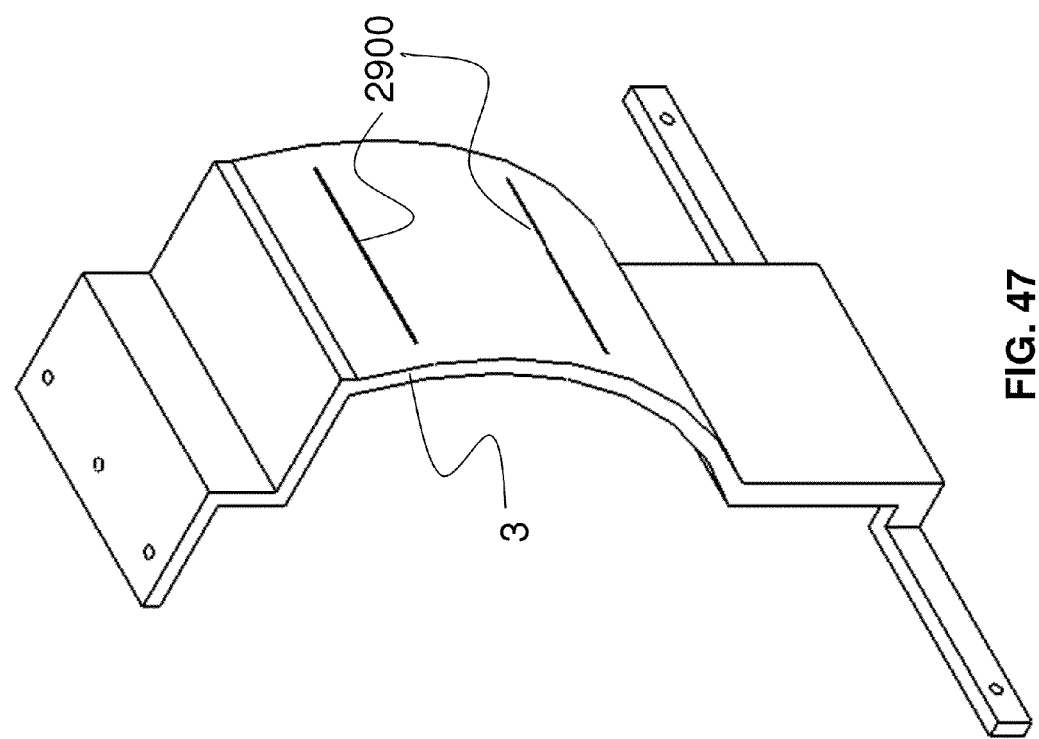
FIG. 47 is a perspective view of the collimator of the multi-linear x-ray scanner of FIG. 40.
Figure 50:
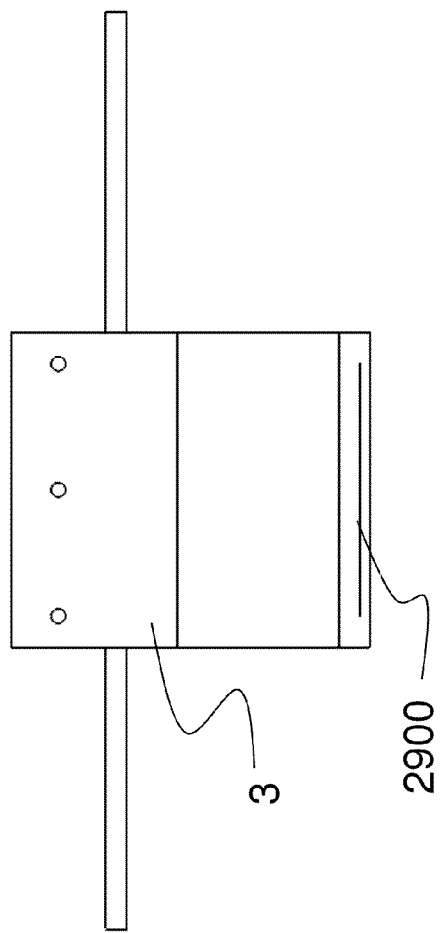
FIG. 50 is a top plan side view of the collimator of the multi-linear x-ray scanner of FIG. 40 from a left side thereof.
Figure 49:
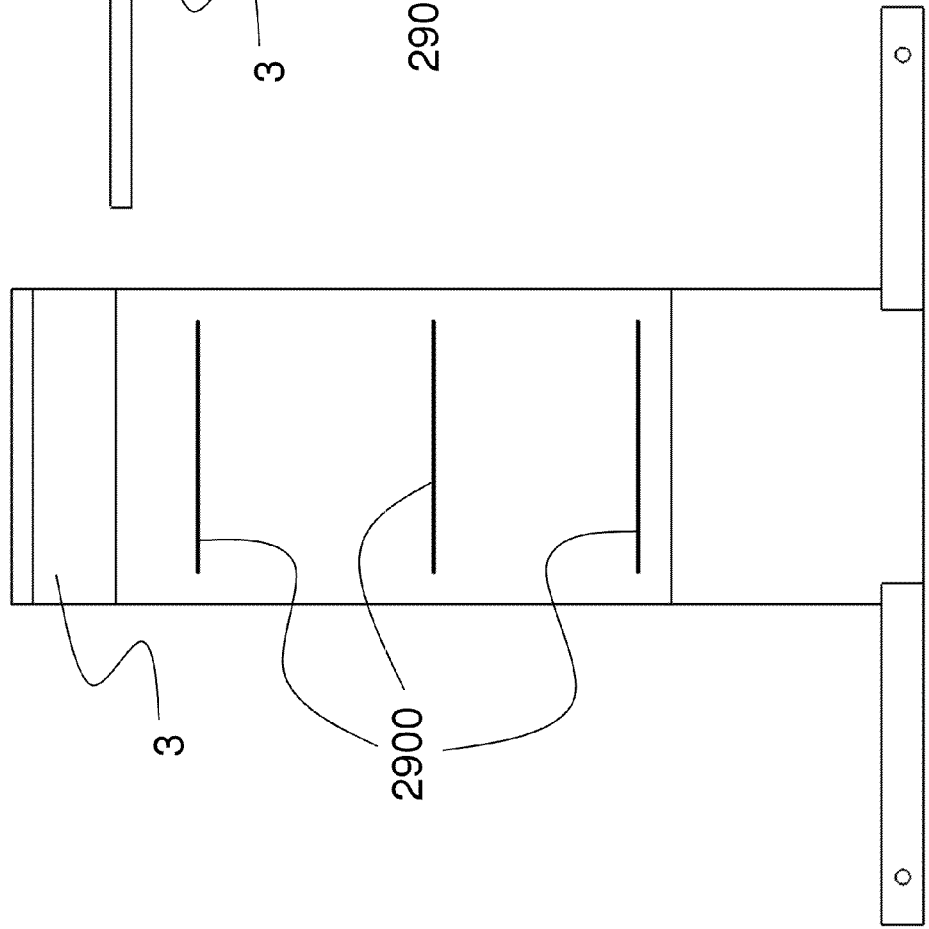
FIG. 49 is a front side elevational view of the collimator of the multi-linear x-ray scanner of FIG. 40.

FIG. 42 illustrates the drive motor 128 having pivoted the pivot arms 123 downwards to rock the x-ray source 1 upwards so that the x-ray beams 5 are generated to impinge the vertical-moving arrays 8 at their upper-most position and the horizontal-moving array 8 at its distal-most position. In contrast, FIG. 43 illustrates the drive motor 128 having pivoted the pivot arms 123 upwards to rock the x-ray source 1 downwards so that the x-ray beams 5 are generated to impinge the vertical-moving arrays 8 at a lower position and the horizontal-moving array 8 at an intermediate position. Similarly, FIGS. 44 to 47 illustrate similar motion of this embodiment of the x-ray source 1. FIG. 44 illustrates the drive motor 128 having pivoted the pivot arms 123 downwards to rock the x-ray source 1 upwards so that the x-ray beams 5 are generated to impinge the vertical-moving arrays 8 at an upper-most position and the horizontal-moving array 8 at its distal-most position. FIG. 45 illustrates the drive motor 128 having pivoted the pivot arms 123 slightly upwards to rock the x-ray source 1 downwards so that the x-ray beams 5 are generated to impinge the vertical-moving arrays 8 at a lower position and the horizontal-moving array 8 at an intermediate position. Finally, FIG. 46 illustrates the drive motor 128 having pivoted the pivot arms 123 slightly upwards to rock the x-ray source 1 downwards so that the x-ray beams 5 are generated to impinge the vertical-moving arrays 8 at a lower-most position and the horizontal-moving array 8 at a proximal-most position.

Motion of the x-ray source 1 is controlled by the microcontroller 16 to keep the motion of the arrays 8 in synchronization with the x-ray beams 5. In this embodiment, alignment of the collimator 3 with the x-ray source 1 is assured because the collimator 3 is fixed to the x-ray source 1. The collimator 3 can be made long and wide enough so that it completely blocks all of the x-rays in the emission cone 55 from escaping the x-ray generator cabinet 30. Various views of the collimator are shown in FIGS. 44 to 47. Even though the collimator 3 is shown with open sides in the various figures of the drawings, for example, in FIGS. 40 and 41, to illustrate how the x-rays pass through the slots 2900 of the collimator 3, the x-ray source 1 has shielded sides in use to prevent undesired transmission of x-rays.

Figure 51:
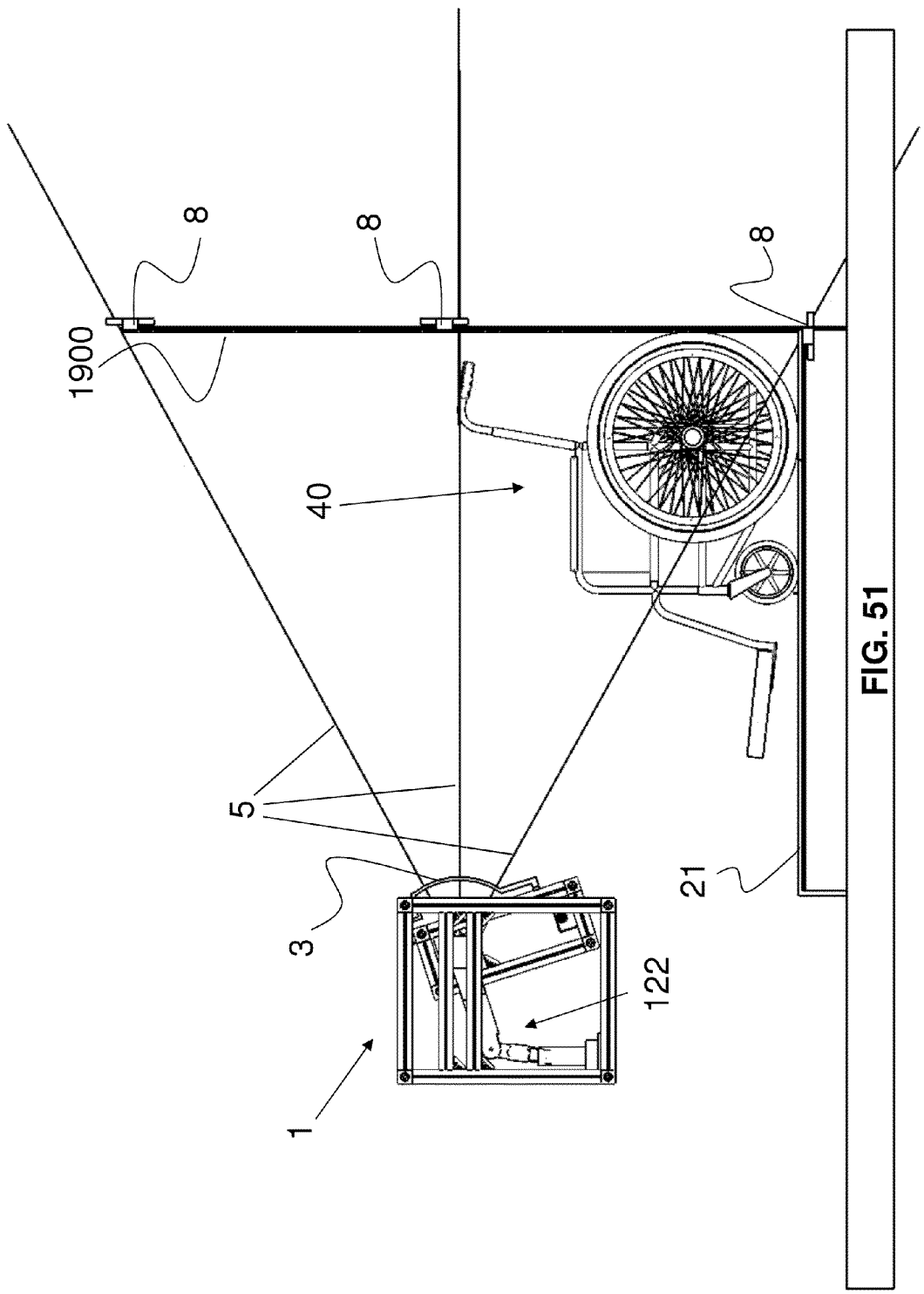
FIG. 51 is a side elevational view of the multi-linear x-ray scanner of FIG. 40 with the collimator pivoted to a raised position to scan a wheelchair.
Figure 52:
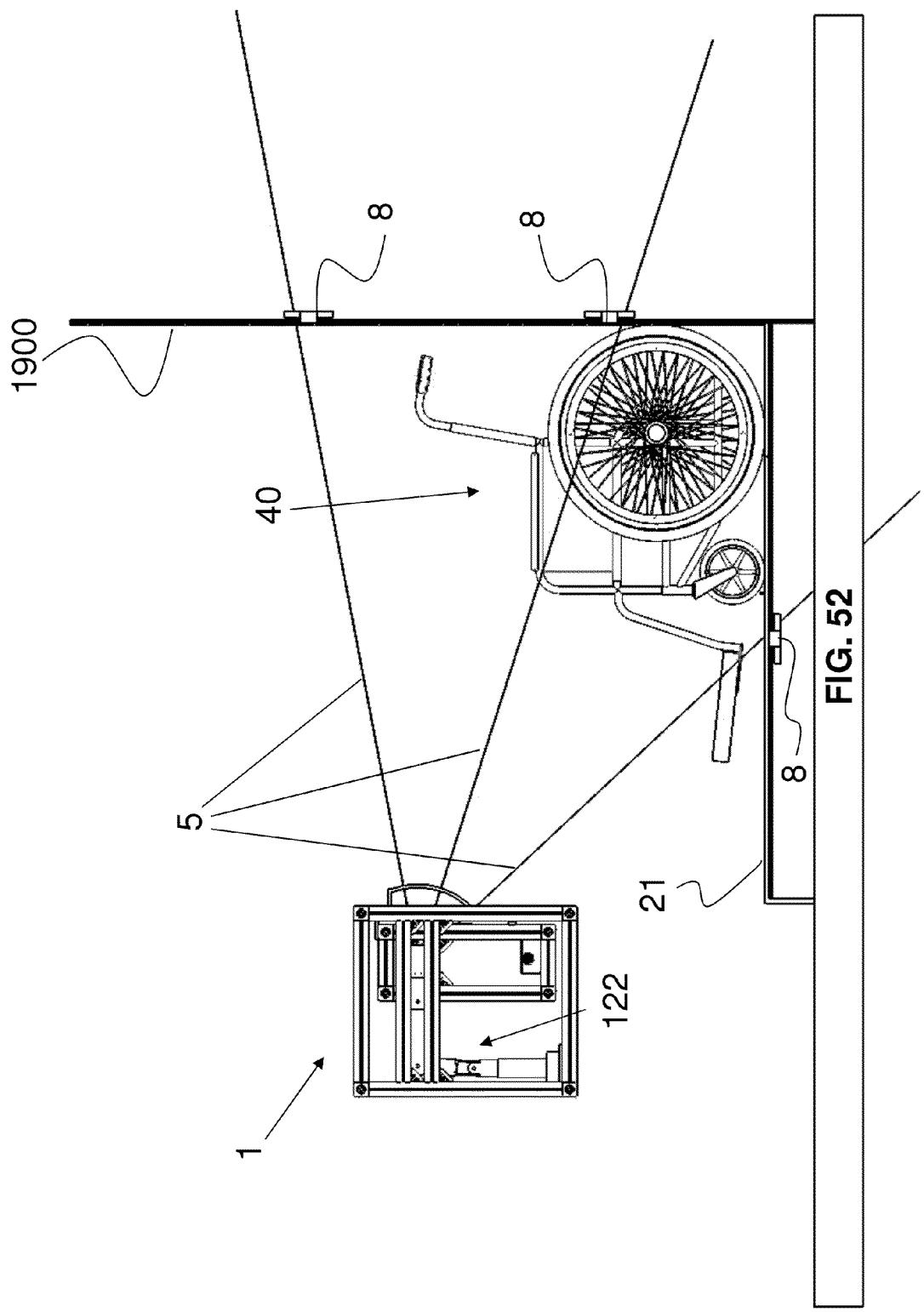
FIG. 52 is a side elevational view of the multi-linear x-ray scanner of FIG. 51 with the collimator pivoted to an intermediate position.
Figure 53:
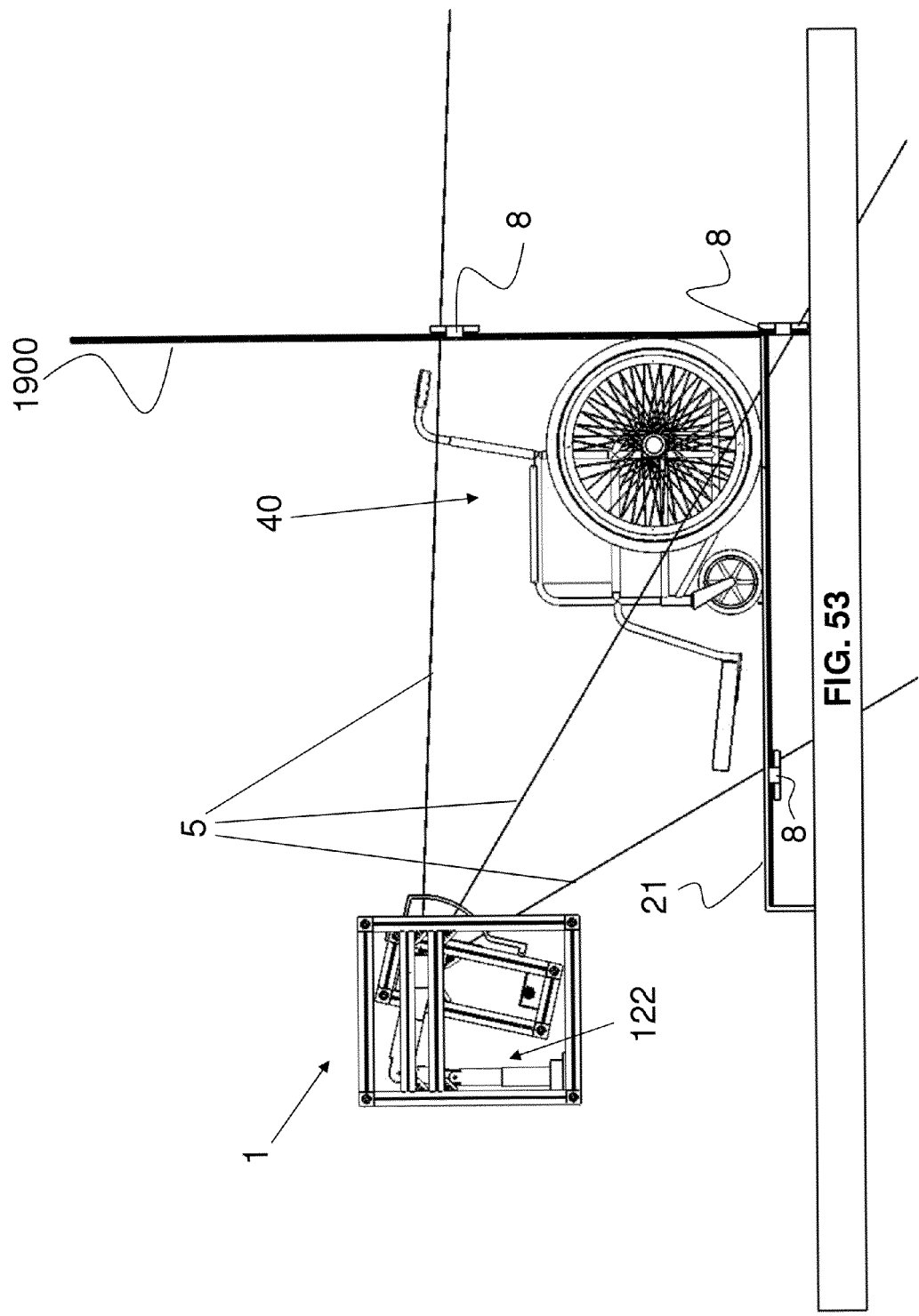
FIG. 53 is a side elevational view of the multi-linear x-ray scanner of FIG. 51 with the collimator pivoted to a lowered position.
Figure 54:
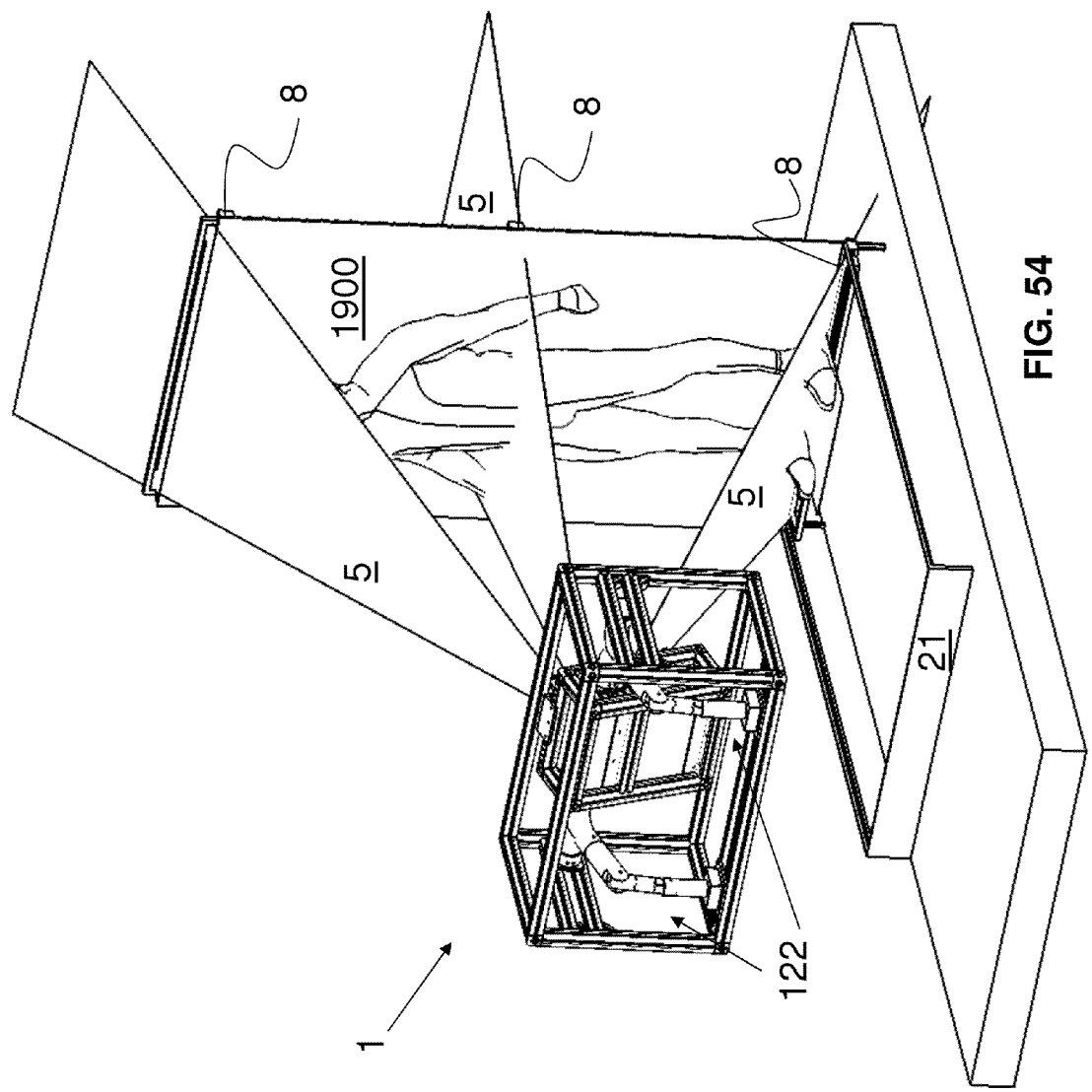
FIG. 54 is a perspective view of the multi-linear x-ray scanner of FIG. 40 with the collimator pivoted to a raised position to scan a person.
Figure 55:
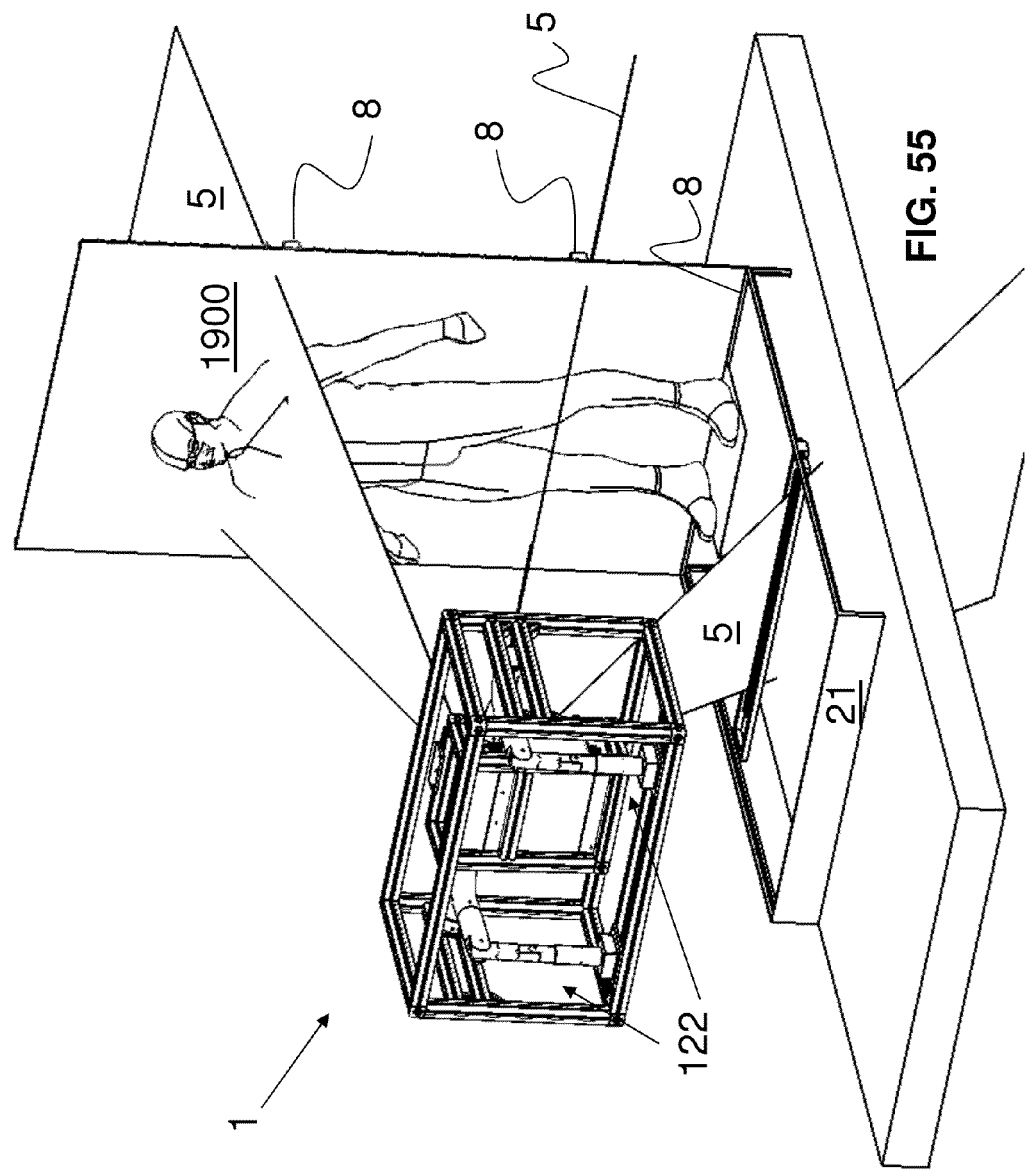
FIG. 55 is a perspective view of the multi-linear x-ray scanner of FIG. 54 with the collimator pivoted to an intermediate position.
Figure 56:
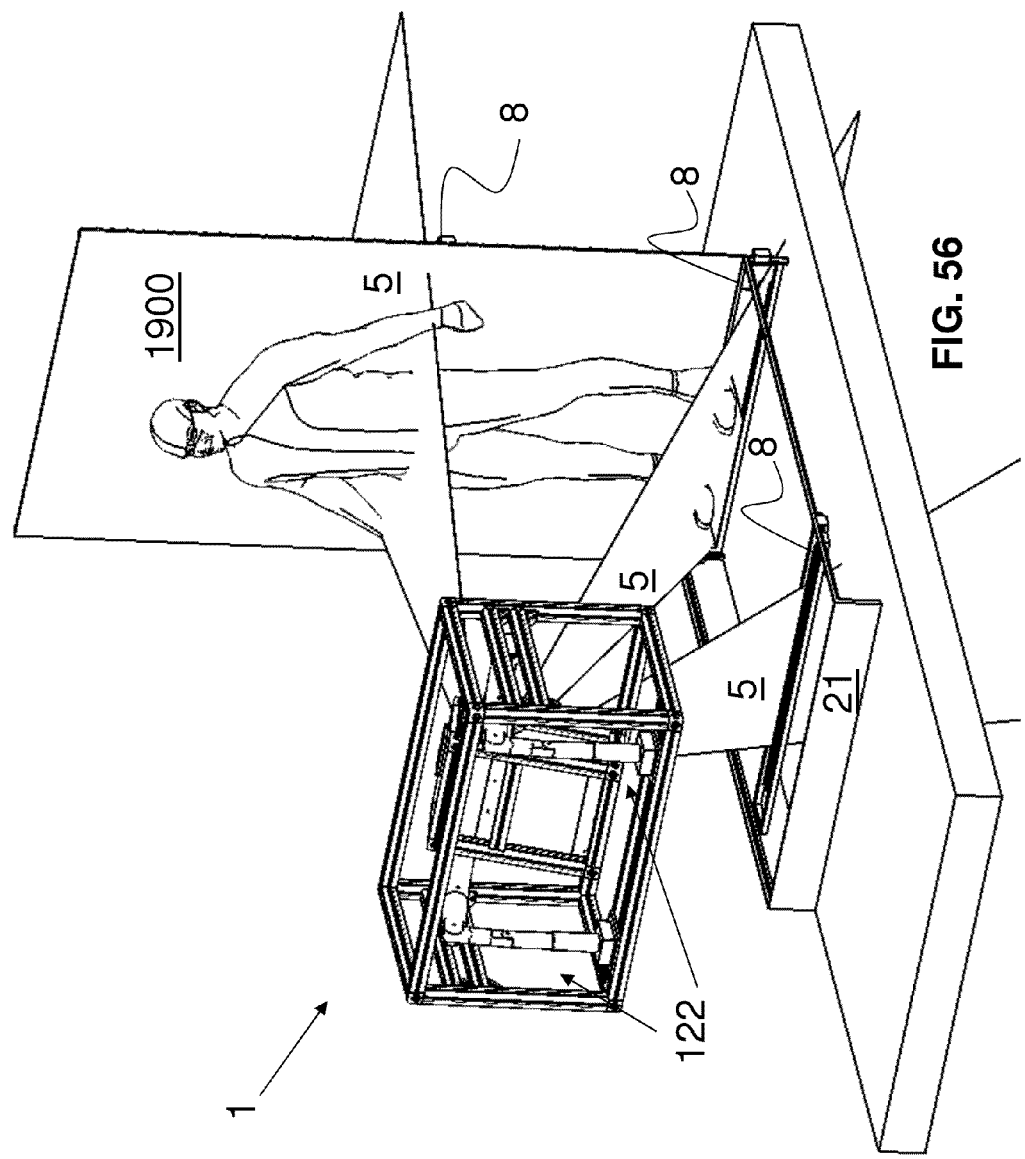
FIG. 56 is a perspective view of the multi-linear x-ray scanner of FIG. 54 with the collimator pivoted to a lowered position.

The mounting frame 120 of the x-ray source 1 is attached to a platform inside the x-ray generator cabinet 30. The platform has adjustable attachment points to secure the x-ray source 1 in a center of rotation of the focal spot at a height above the platform 21 to provide complete coverage of the scanning area. With the configuration described, FIGS. 51 to 53 show how a person in a wheelchair can be scanned completely with the x-ray source 1, and FIGS. 54 to 56 show how a person standing against the wall 1900 can be scanned completely with the x-ray source 1.

It is advantageous to use a mechanical linkage mechanism to align the arrays 8 with the x-ray beams 5 during the scan with a configuration having the mechanical mechanism not interfering with movement into and out from the scanning platform 21. It is also advantageous to mount the collimator 3 onto the x-ray source 1 to eliminate any need to maintain alignment between the collimator 3, the x-ray source 1 focal spot, and the arrays 8 during a scan. An exemplary embodiment having such features is presented in FIGS. 57 through 68. In this embodiment, the x-ray source 101 (which in this embodiment is an x-ray tube) is mounted on a vertical cylindrical support post 130. The support post 130 has an upper support platform 140 for mounting thereon the x-ray source 101. A mounting and alignment bracket 150 connects the x-ray source 101 to the support platform 140 so that the focal spot of the x-ray source 101 is aligned with the central axis of the cylindrical support post 130, also referred to as the x-ray source movement axis. For effecting such alignment, the mounting and alignment bracket 150 can move the x-ray source 101 in both the X and Y directions on the support platform 140.

Figure 58:
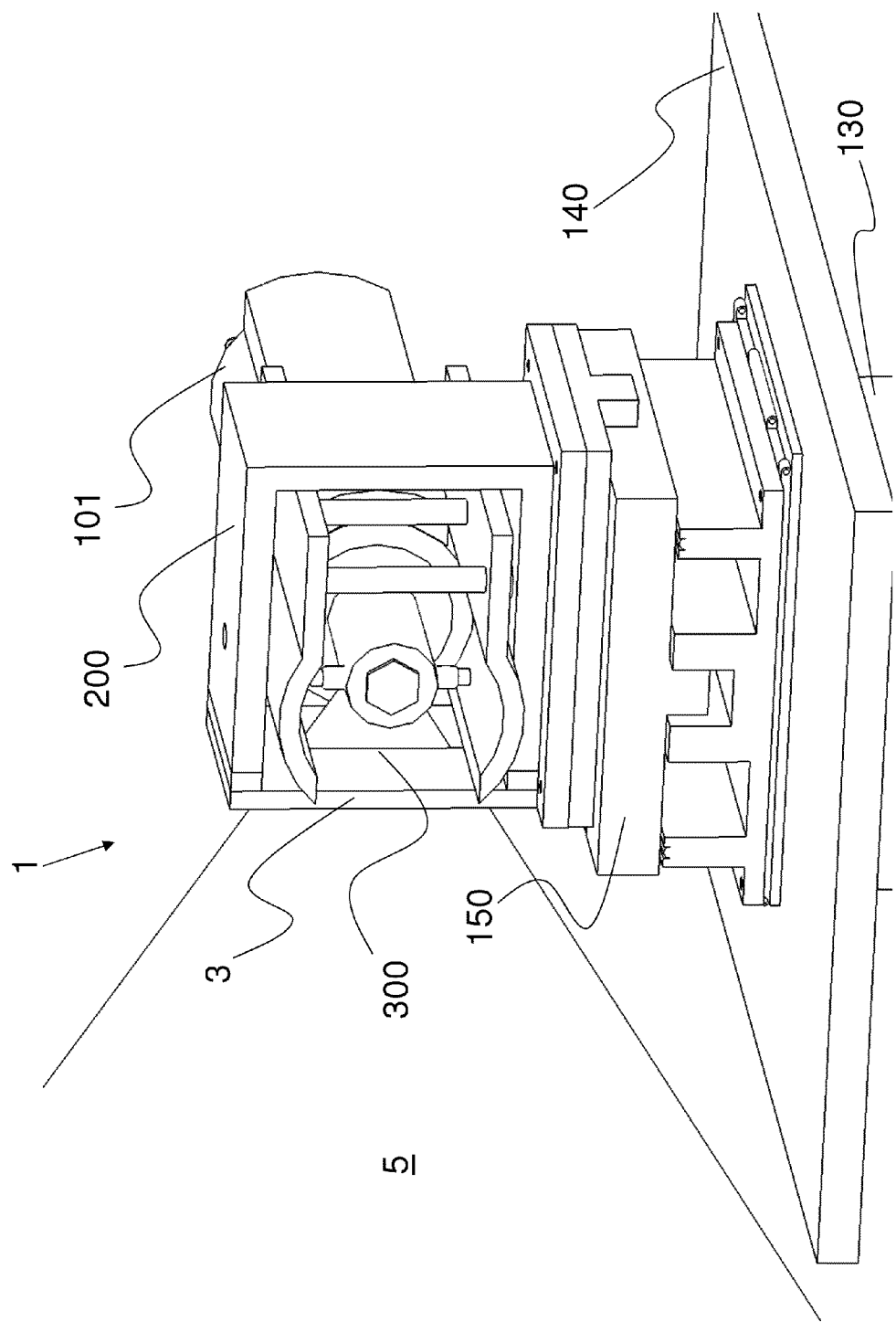
FIG. 58 is a fragmentary, enlarged, perspective view of the multi-linear x-ray scanner of FIG. 57 from behind a left side thereof.
Figure 59:
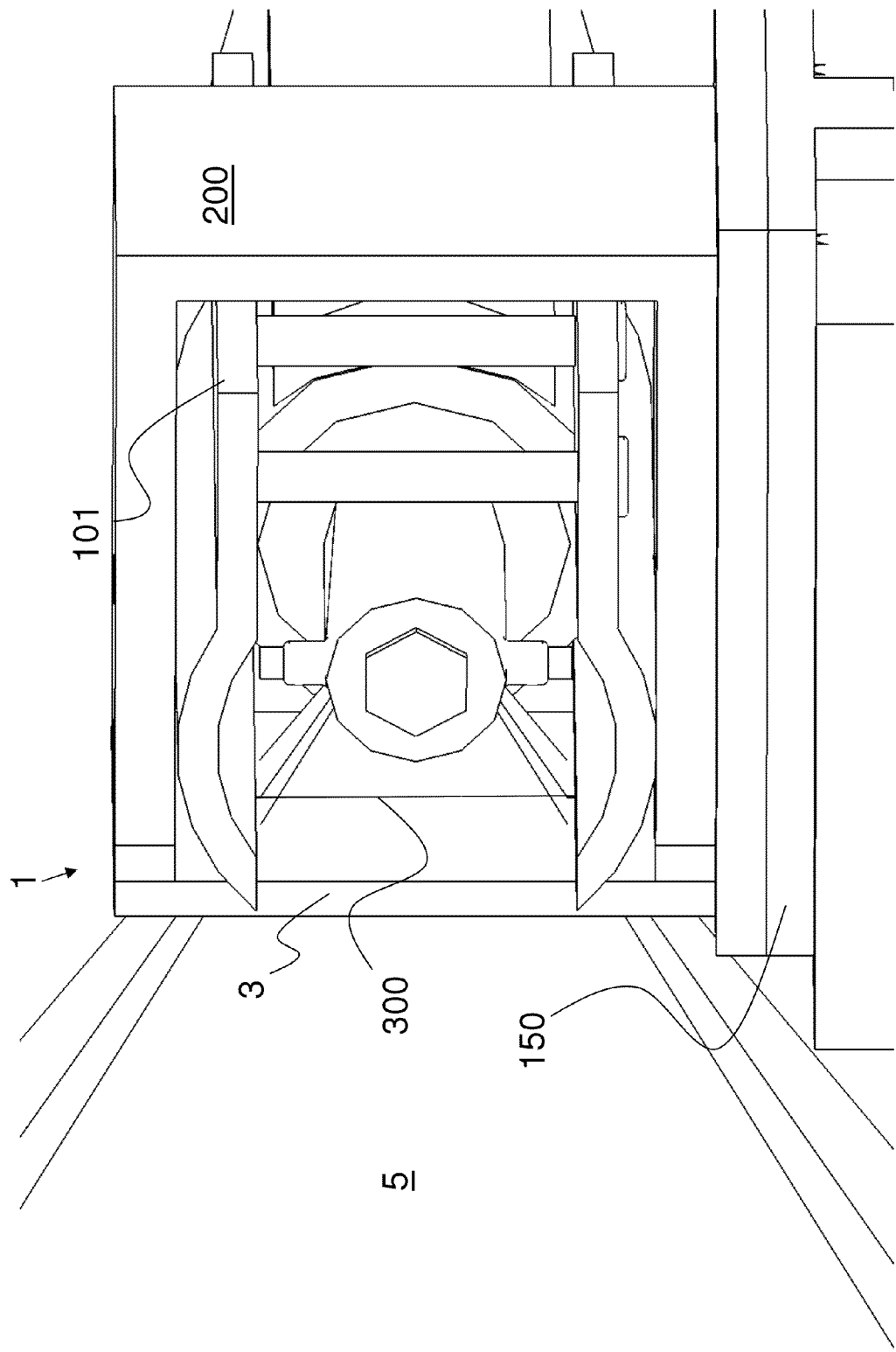
FIG. 59 is a fragmentary, further enlarged, perspective view of the multi-linear x-ray scanner of FIG. 57 from behind a left side thereof.
Figure 60:
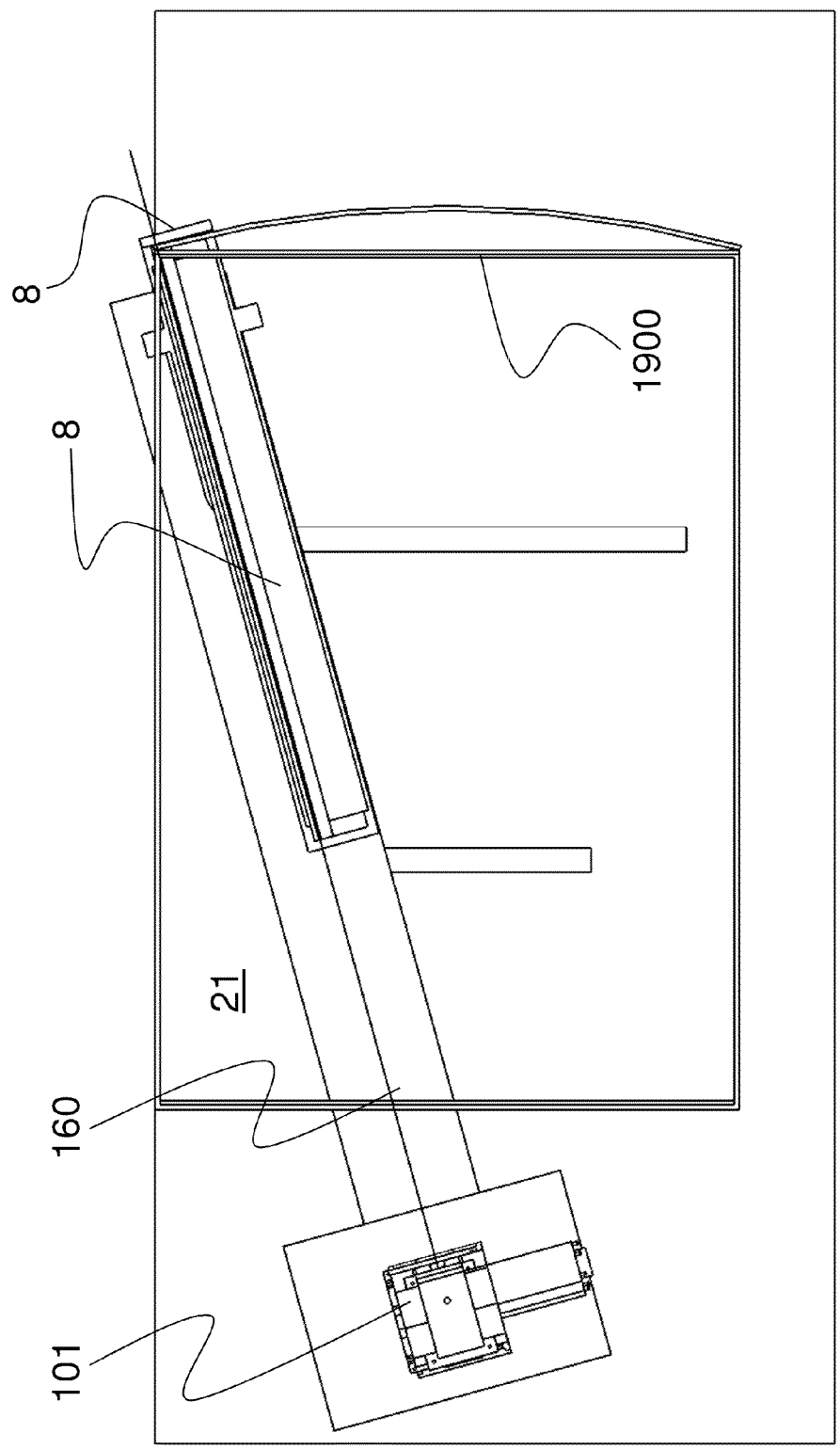
FIG. 60 is a top plan view of the multi-linear x-ray scanner of FIG. 57.
Figure 61:
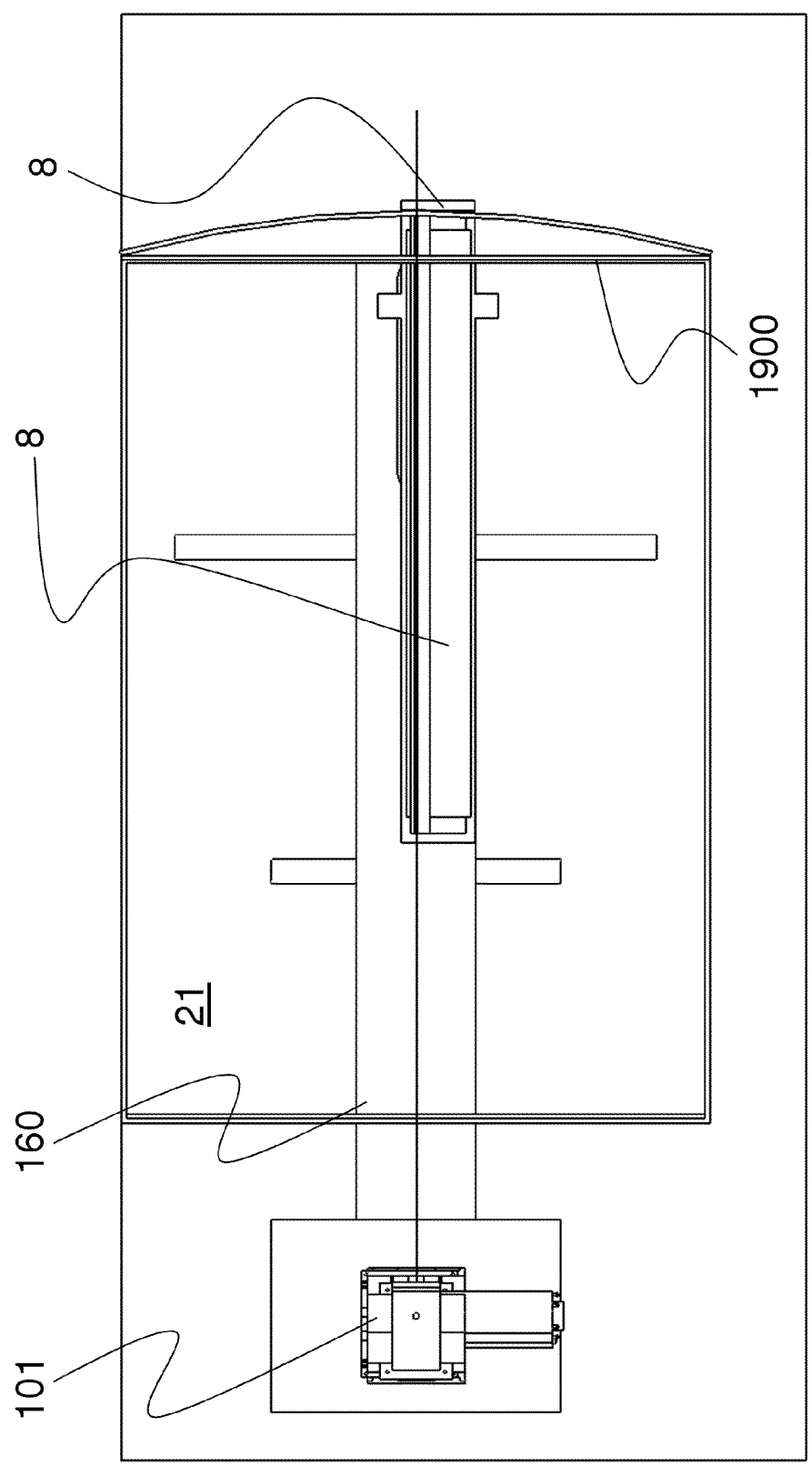
FIG. 61 is a top plan view of the multi-linear x-ray scanner of FIG. 57 with the collimator and scanner arrays pivoted to a centered position.
Figure 62:
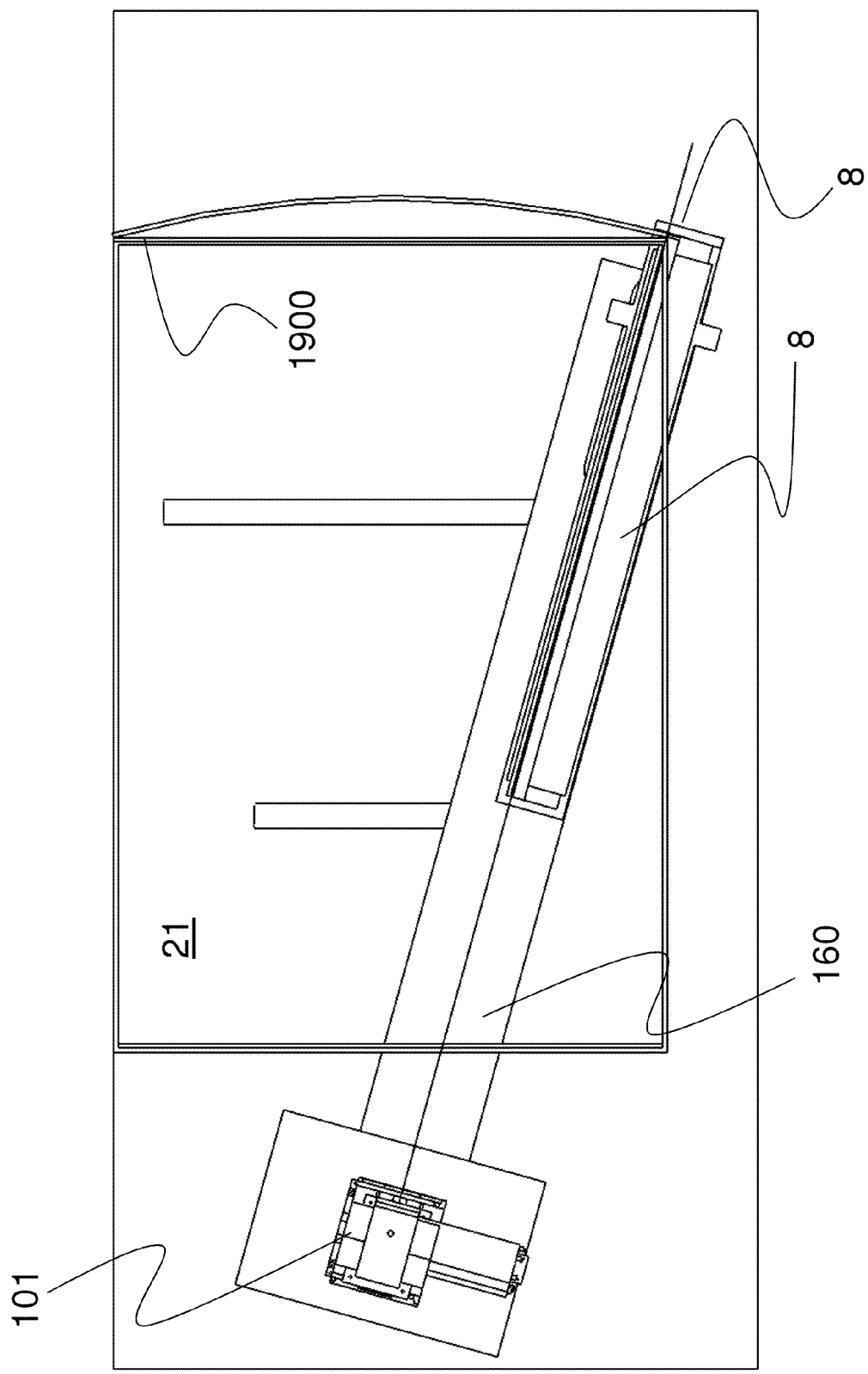
FIG. 62 is a top plan view of the multi-linear x-ray scanner of FIG. 57 with the collimator and scanner arrays pivoted to a right position.
Figure 63:
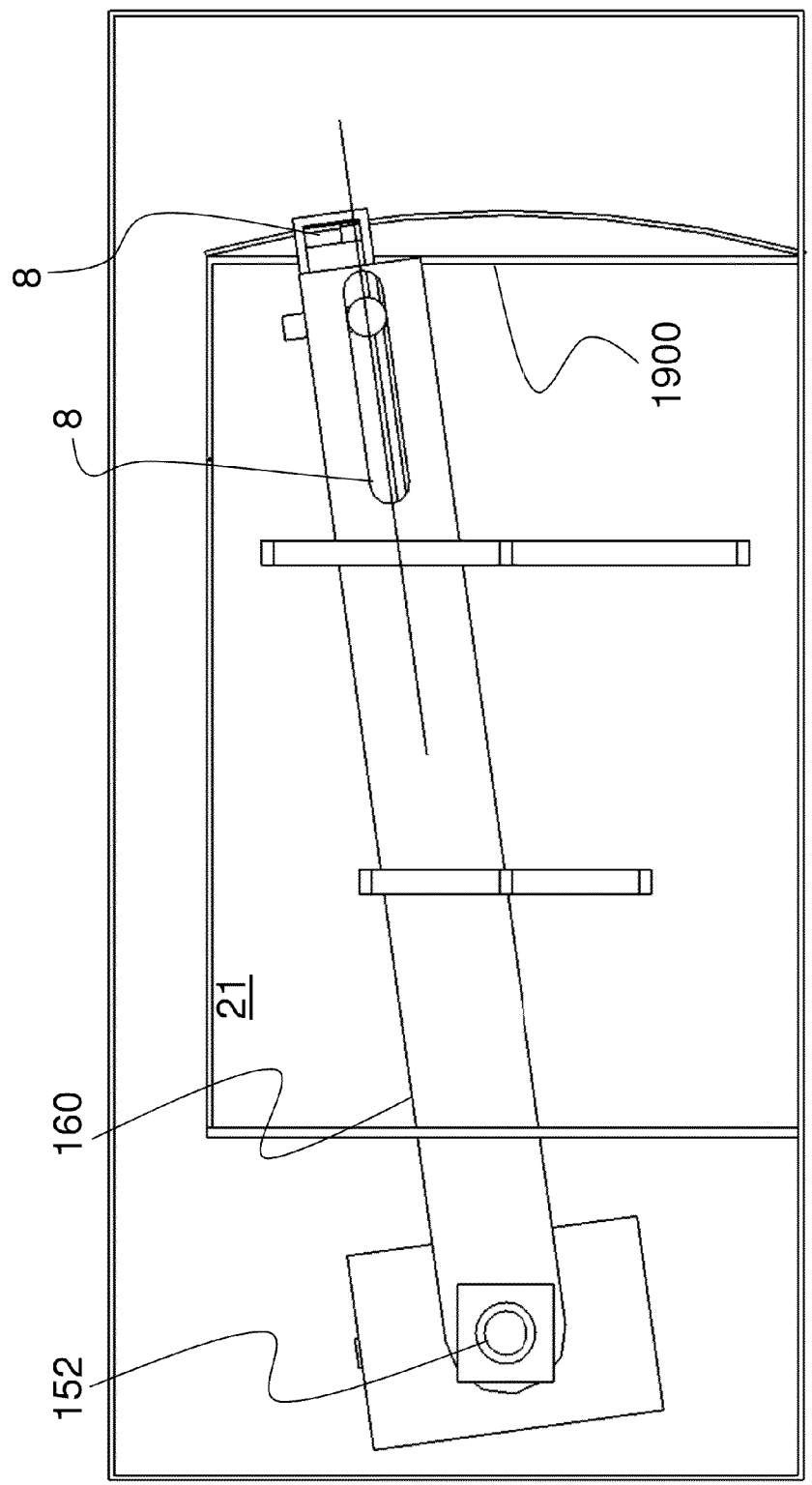
FIG. 63 is a bottom plan view of the multi-linear x-ray scanner of FIG. 57 with the collimator and scanner arrays pivoted to an intermediate right position.

The support post 130 is mounted rotatably on a bearing 132 that allows it to rotate freely about the vertical central axis of the support post 130. An "L-shaped" mechanical arm 160 is attached to the bottom of the support post 130 and has a horizontal portion extending perpendicular to and away from the vertical axis of the support post 130 below the floor of the platform 21. A vertical portion of the arm 160 extends parallel to the vertical axis of the support post 130 behind the wall 1900. In an exemplary configuration, the horizontal portion of the mechanical arm 160 extends away from the support post 130 by approximately 2.2 meters. At the distal end of the horizontal portion, the vertical portion extends vertically upwards for approximately 2.2 meters. The mechanical support arm 160 is fixed to the support post 130 so that it rotates with the support post 150. Such a configuration insures that the arrays 8 are aligned with the x-ray beam(s) 5. A first array 8 is mounted at the horizontal portion beneath the platform 21 on which the person is located. The second array 8 is mounted at the vertical portion of the arm 160. In this configuration, therefore, only a single x-ray beam 5 needs to be emitted through the collimator 3 to intersect with both the horizontal and vertical arrays 8. As the support post 150 is rotated, the x-ray beam 5 sweeps over the platform 21 to produce an image. In this configuration, the mechanical arm 53 that supports and aligns the array 8 moves underneath the platform 21 and behind the wall 1900, thereby eliminating any egress restrictions encountered in previous embodiments described herein. FIGS. 58 and 59 illustrate various views of the system above the platform 160. The collimator 3 has one slit opening 300 and is mounted to the x-ray source 1 with an adjustable mounting bracket 200.

Figure 57:
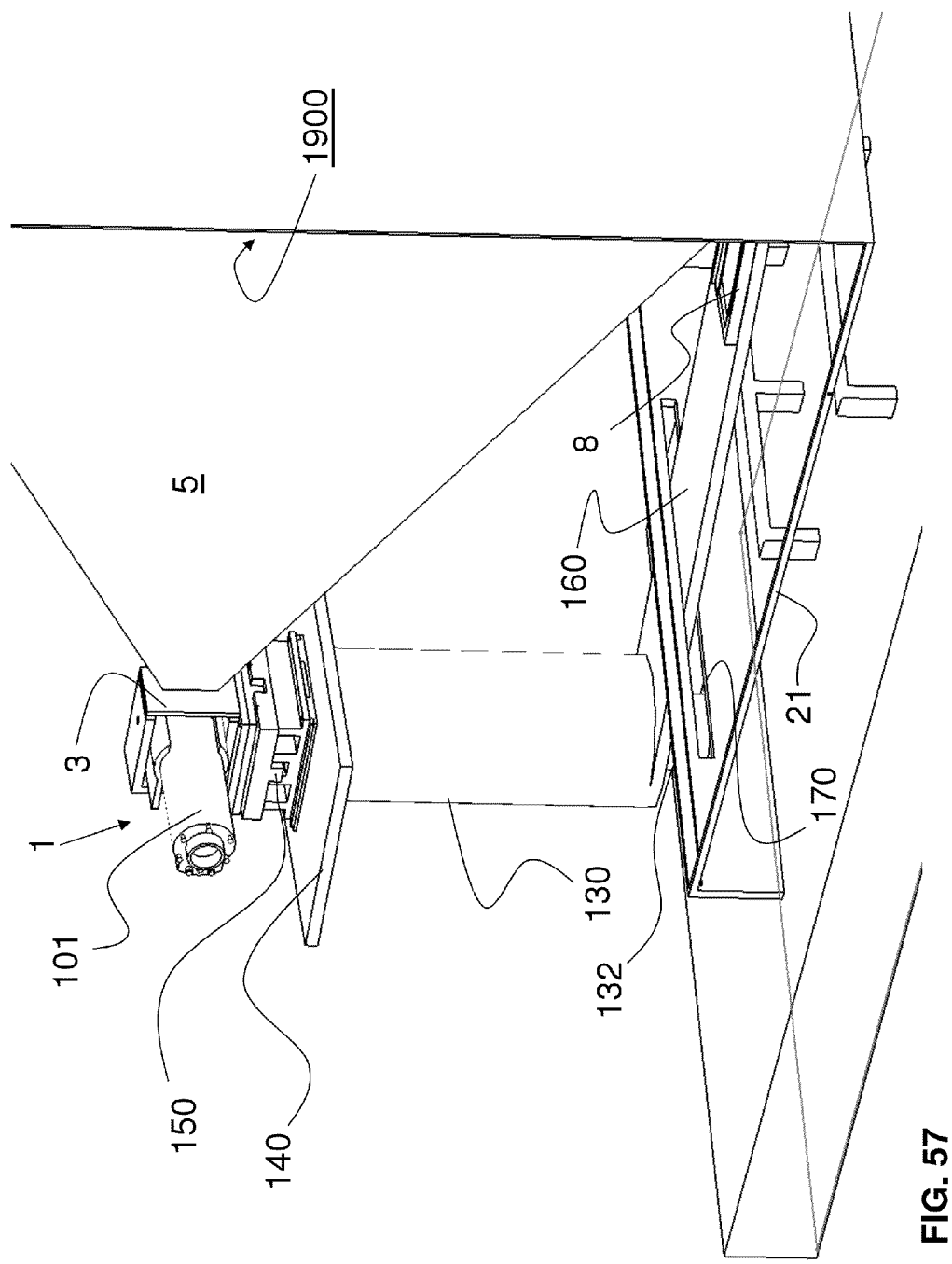
FIG. 57 is a fragmentary, perspective and partially transparent view of an exemplary embodiment of a multi-linear x-ray scanner from a front side thereof with a portion of the generator cabinet removed and with a collimator and scanner arrays pivoted to a left position.

As shown in FIGS. 60 to 63, the mechanical arm 160 is rotated with a single drive motor 111 through an angle sufficient to sweep the array 8 across the entire width of the scanning platform 21 both in the floor and in the rear wall of the imaging cabinet 31. In an exemplary embodiment, the drive motor 111 is connected to a ball screw or other drive mechanism that is further connected to the mechanical arm 160. The position and speed of the drive motor 111 is measured by an encoder. In this embodiment, only one drive motor 11 is required to drive the entire imaging assembly including the collimator 3 and the x-ray source 1. The mechanical arm 160 is supported by bearings and brackets to keep it from flexing and, if desired, a port 170 in the platform can provide support to the horizontal portion as shown in FIG. 57. The weight of the x-ray source 1 is supported by the support column 150, and the mechanical arm 160 is also supported by bearings, greatly reducing the torque and power required by the drive motor 111.

Figure 64:
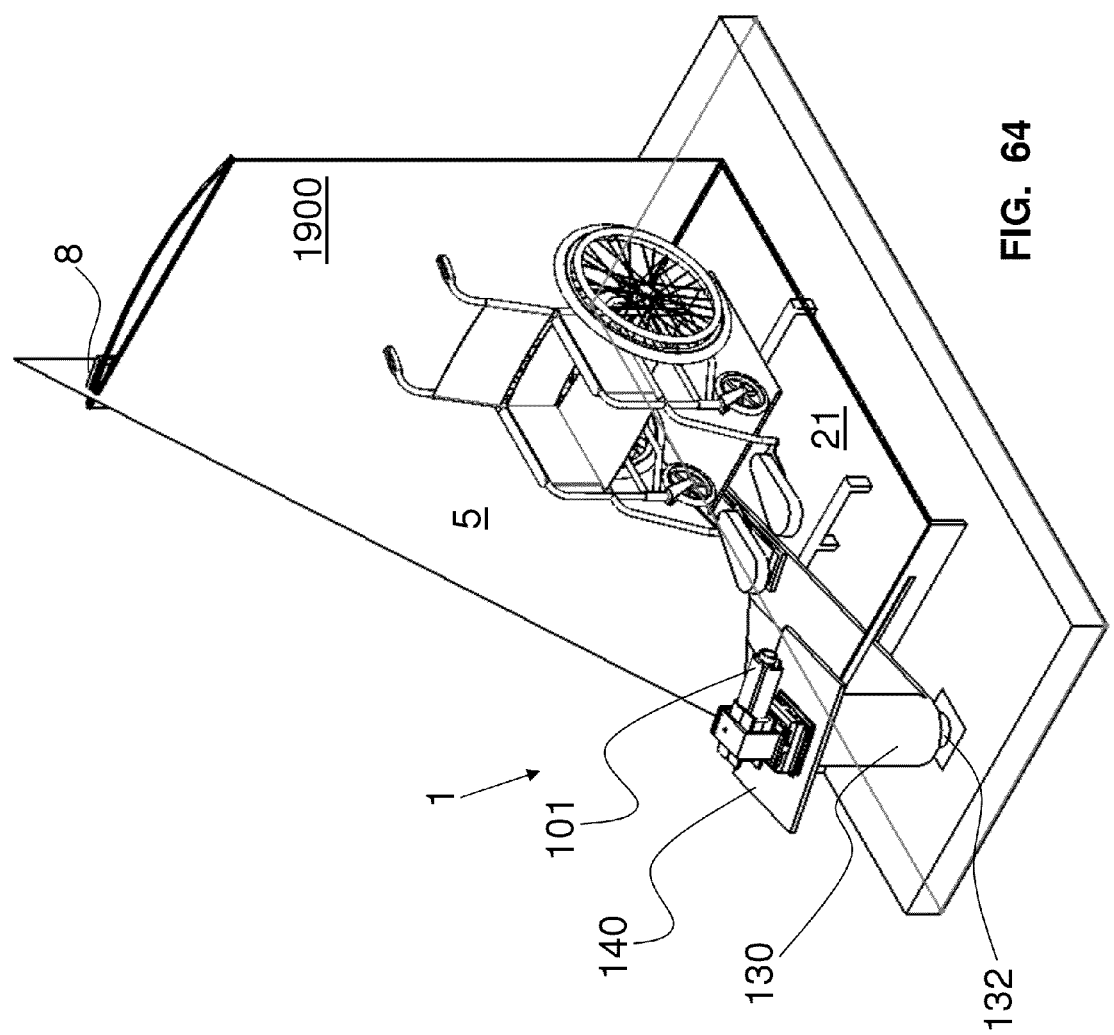
FIG. 64 is a perspective view of the multi-linear x-ray scanner of FIG. 57 from a front right side thereof and scanning a wheelchair with the collimator and scanner arrays pivoted to a left position.
Figure 65:
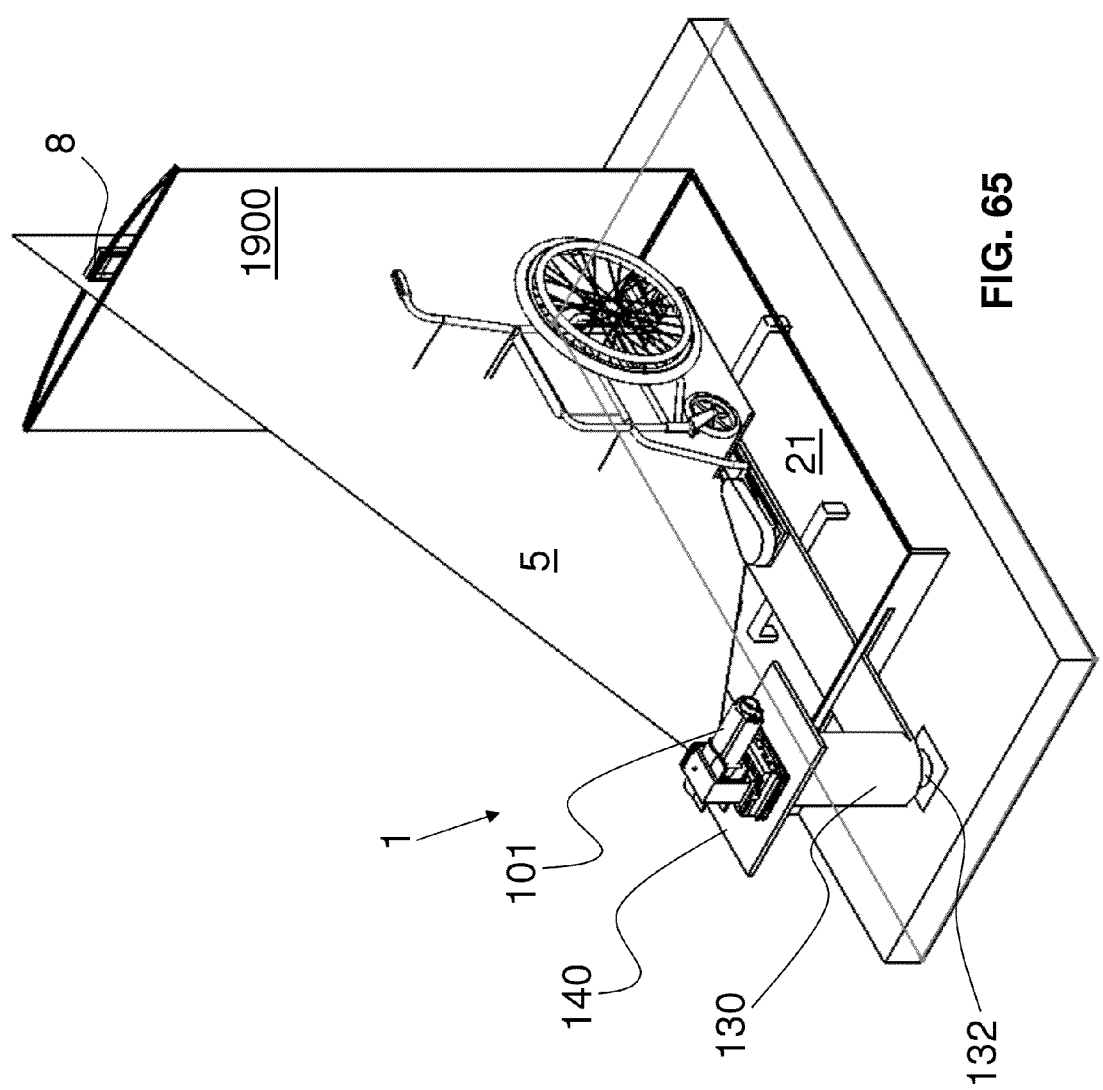
FIG. 65 is a perspective view of the multi-linear x-ray scanner of FIG. 64 with the collimator and scanner arrays pivoted to a centered position.
Figure 66:
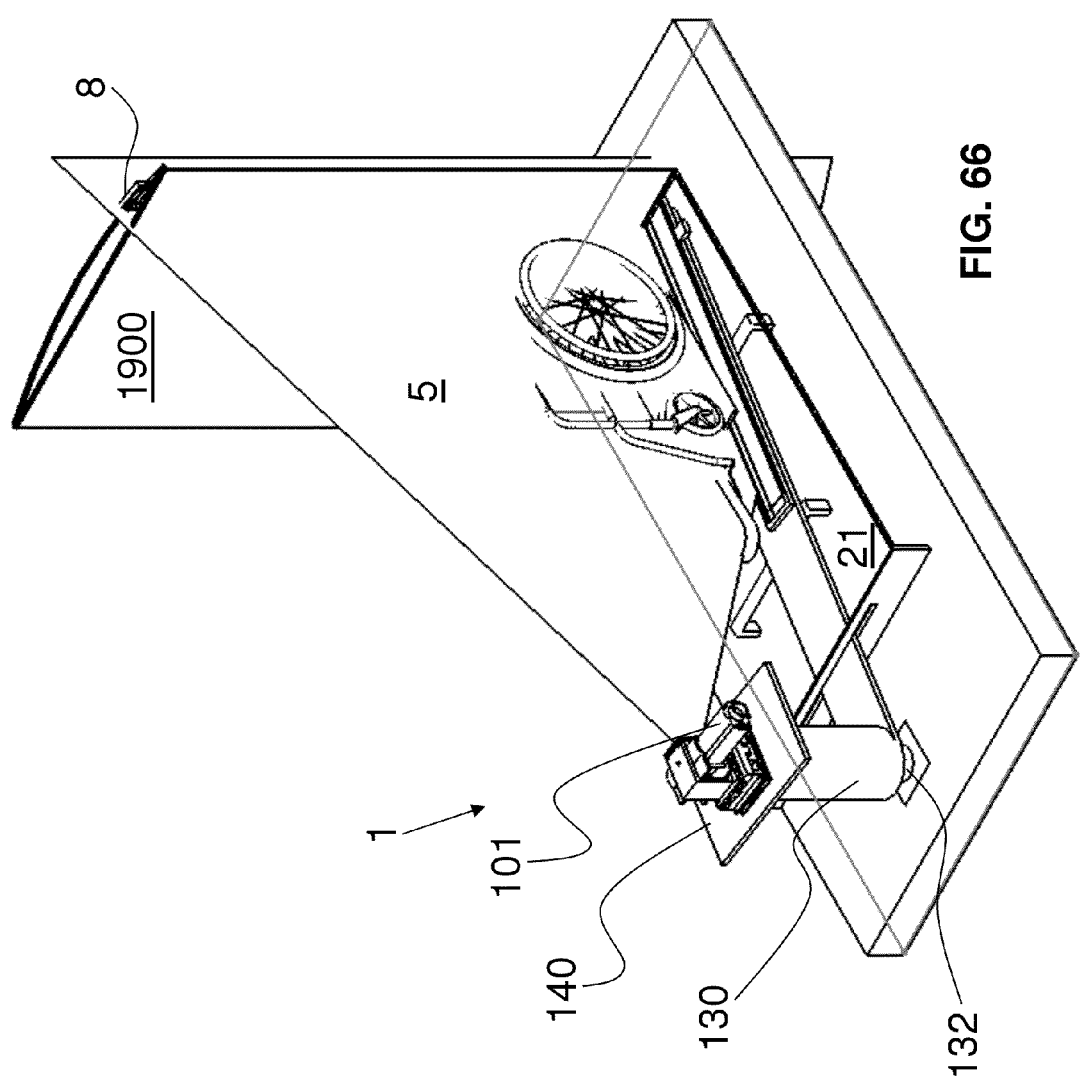
FIG. 66 is a perspective view of the multi-linear x-ray scanner of FIG. 64 with the collimator and scanner arrays pivoted to a right intermediate position.
Figure 67:
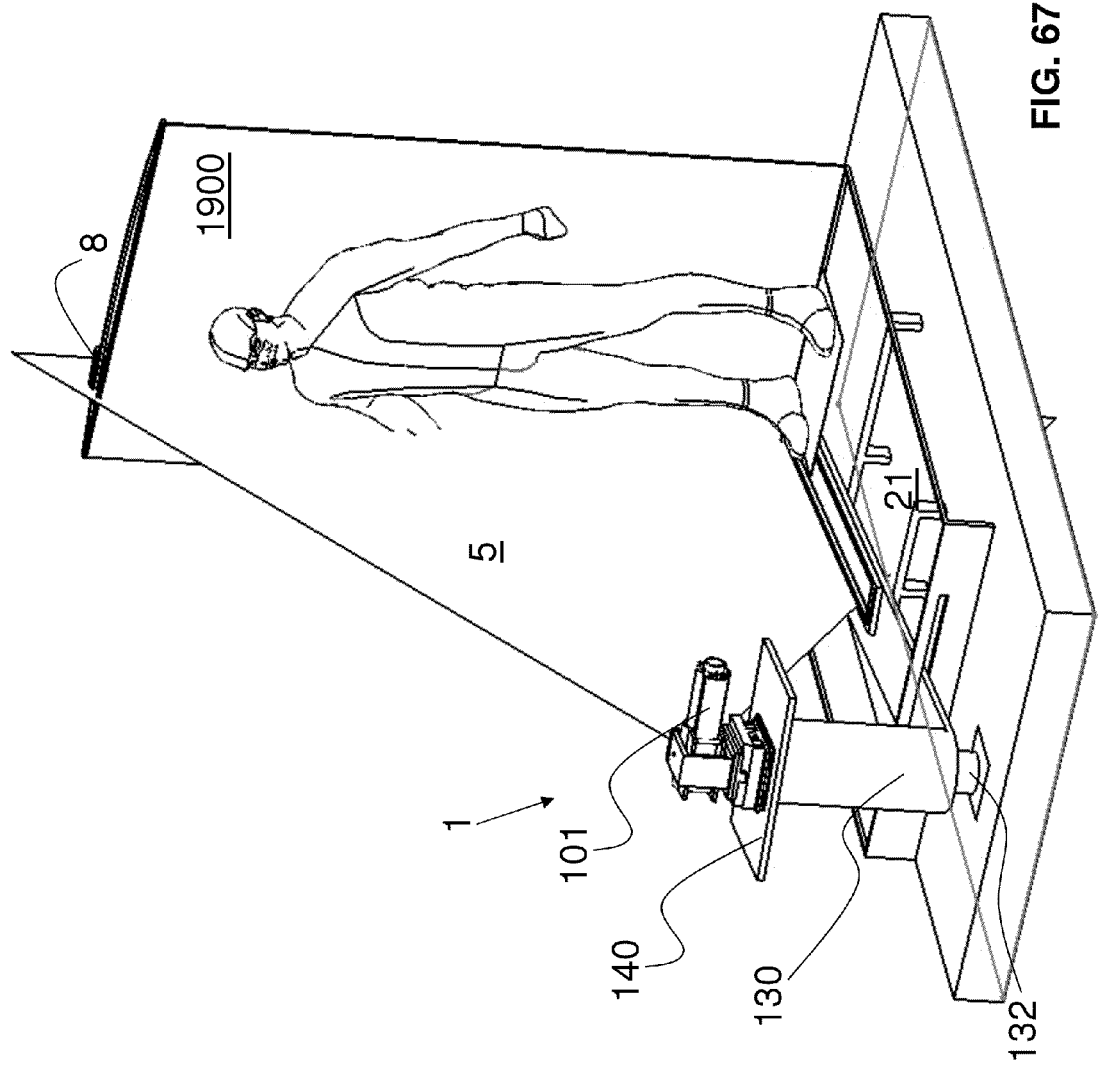
FIG. 67 is a perspective view of the multi-linear x-ray scanner of FIG. 57 from a front right side thereof and scanning a person with the collimator and scanner arrays pivoted to a left intermediate position.
Figure 68:
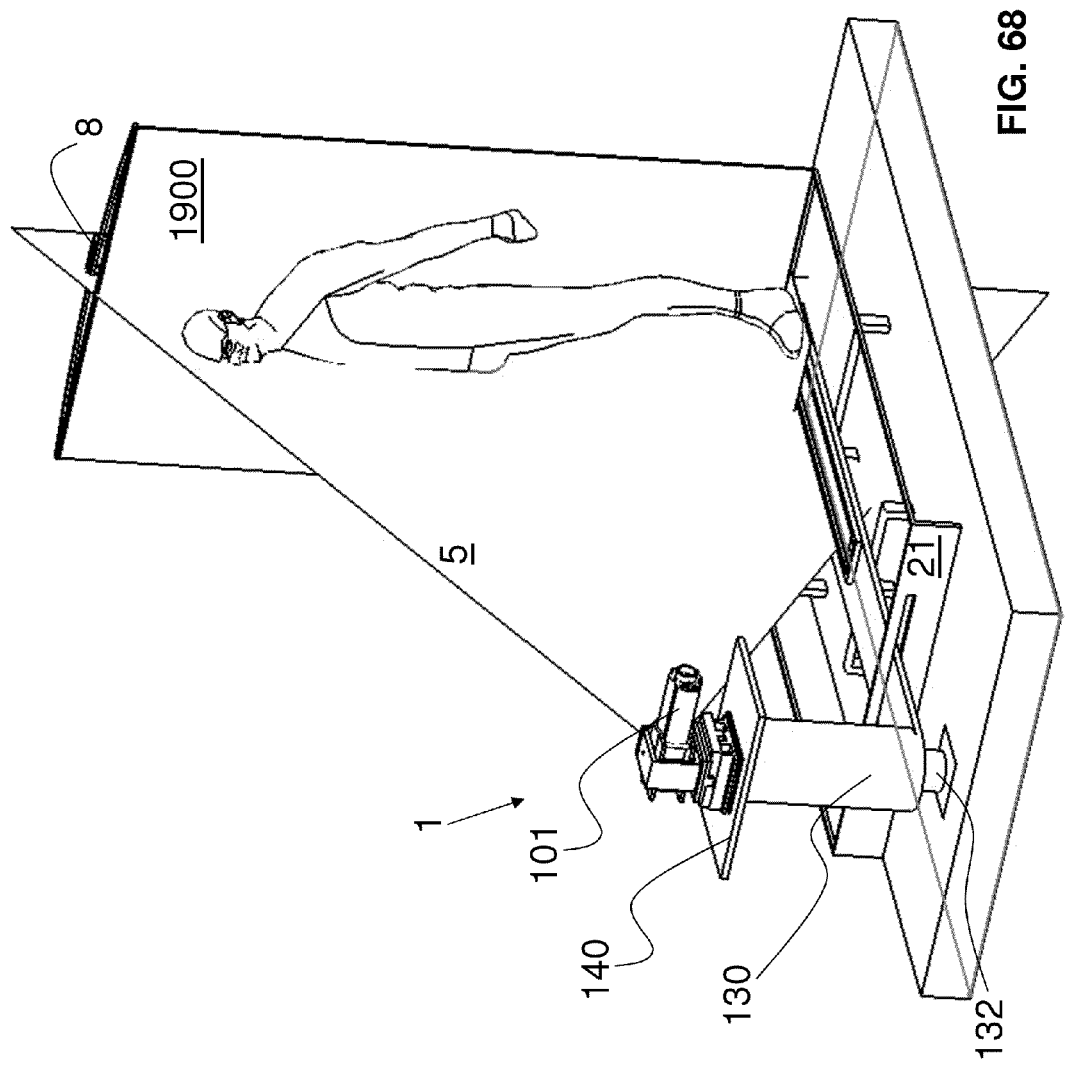
FIG. 68 is a perspective view of the multi-linear x-ray scanner of FIG. 64 with the collimator and scanner arrays pivoted to a centered position.

With the configuration described, FIGS. 64 to 66 show how a person in a wheelchair can be scanned completely with the x-ray source 1, and FIGS. 67 to 68 show how a person standing against the wall 1900 can be scanned completely with the x-ray source 1.

In accordance with another exemplary embodiment of the present invention, the x-ray exposure dose to the person being scanned is monitored and controlled so that each person being scanned receives the lowest possible exposure. It is understood in the medical diagnostic x-ray field that x-ray beam quality plays an important role in simultaneously reducing the exposure dose and improving image quality. X-ray beam quality refers to the x-ray spectrum and intensity used to acquire the image. The x-ray spectrum is determined by the kilo-voltage applied to the x-ray tube, by the anode material of the x-ray tube, and by the filtration used. The intensity of the x-ray beam is determined by the electrical current applied to the tube and by the amount of filtration used. The beam quality that produces the lowest possible dose and highest image quality is a function of the anatomy and mass of the person being exposed. Each person being scanned will have a unique anatomical profile and mass depending on their height and weight. Therefore, in this embodiment, the parameters of the person's anatomical profile are measured before each scan is made in order to determine the required beam quality parameters for administering the lowest possible dose.

In accordance with an exemplary embodiment, a dosimeter is positioned in the x-ray beam 5 to measure and record the x-ray exposure produced during each scan. A set of filters are positioned in front of the collimator 3 to filter the x-ray beam 5. Immediately before a person is scanned, the mechanical arm 50, 160 is positioned in the center of the platform 21 and a single row of image data is acquired using a nominal set of exposure parameters (e.g., 100 kV and 0.3 mA). A histogram of the image data produced is analyzed to determine the amount of attenuation in at least three segmented areas of the line of image data to determine the distance from the top of the head to the abdominal region, the extent of the abdominal region, and the distance to the feet. These data values are used to determine the extent and type of filters to use and the optimum x-ray exposure parameters to use (e.g., kV, mA, and scanning speed) during the scan to produce the lowest dose and best image quality for the person being scanned.

An ideal histogram of image data is one where the average intensity of the pixels within the anatomical region (where x-rays are attenuated by the body) is approximately half of the maximum value and where the distribution of values around the average as large as possible but less than half of the average intensity. Within each line of image data, at least three segmented regions of image values exist: (1) a portion of a line where un-attenuated x-rays impinge on the detectors; (2) a portion of a line where x-rays pass through the extremities (arms, head, and legs) of the person being scanned; and (3) a portion of a line where x-rays pass through the chest and abdominal region. The ideal x-ray spectrum used to image human anatomy is one that has very little soft (low energy) x-rays and has a maximum energy (kV) that is just large enough so that the majority of the x-rays pass through the anatomy. Soft x-rays are absorbed almost entirely by the anatomy and do not reach the detector, so they only contribute to exposure dose but not to the image quality. Higher energy x-rays penetrate better and provide a better dose-to-image quality relationship but also produce a lower detector response as energy is increased. The lower detector response at higher x-ray energy is driven by the response of the scintillating phosphor, which has a reduced efficiency at x-ray energies above 60 keV. Filters such as aluminum and copper are used to optimize beam quality for medical diagnostic x-ray imaging because they preferentially absorb the soft, lower x-ray energies of the x-ray spectrum, thereby reducing the amount of exposure dose and improving the dose efficiency. Accordingly, it is necessary to adjust the maximum kV and spectrum of the x-rays used to image human anatomy in order to maximize the dose efficiency in terms of the amount of x-ray exposure dose used to make a given image quality.

Figure 69:
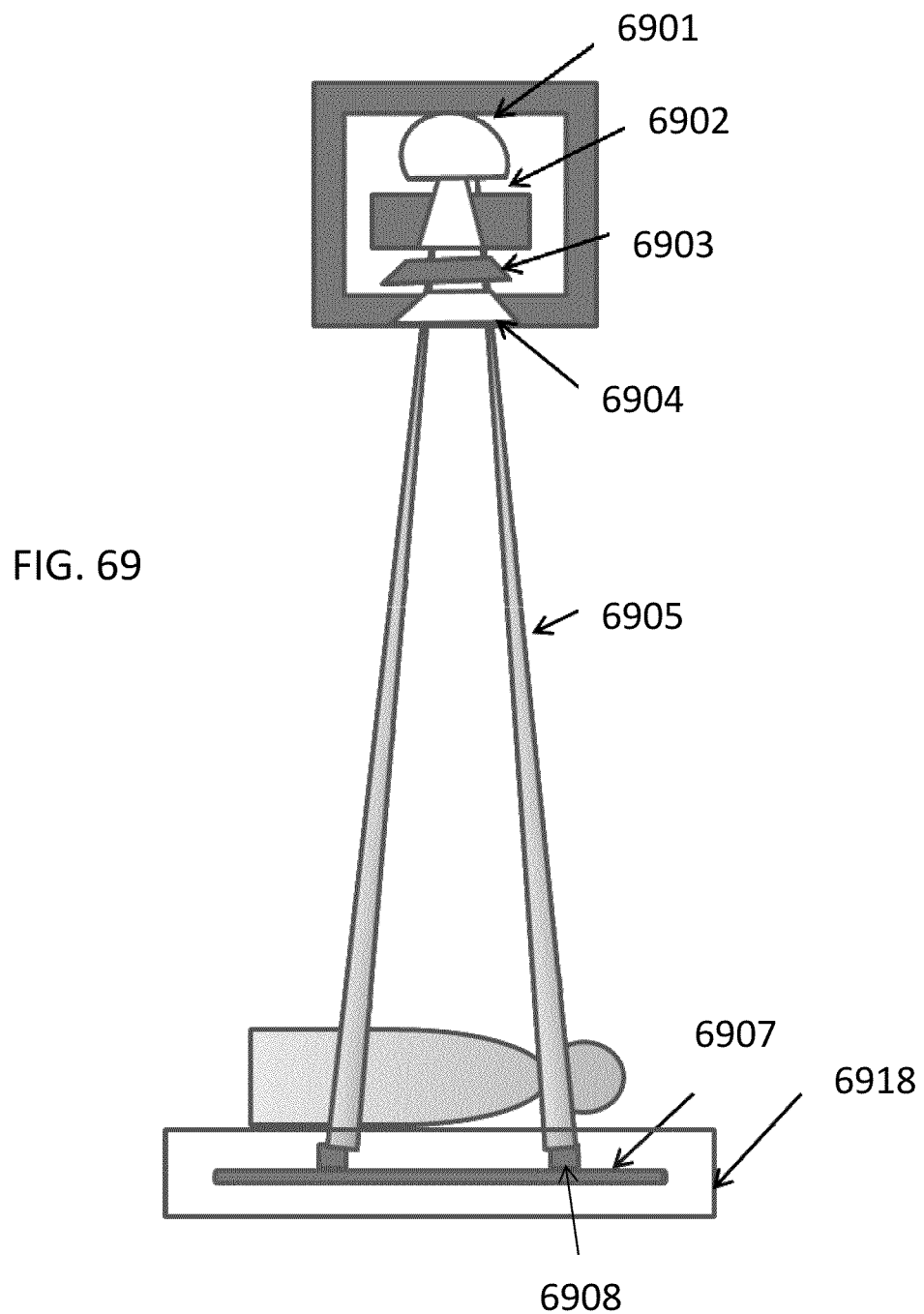
FIG. 69 is a schematic diagram of an exemplary embodiment of an x-ray beam forming and imaging system according to the invention, which includes a shielded housing containing an x-ray generator, filter, dosimeter, and collimator and where a plurality of horizontal x-ray beams pass through a person being scanned and impinge on a detector array including a plurality of x-ray detector arrays.
Figure 70:
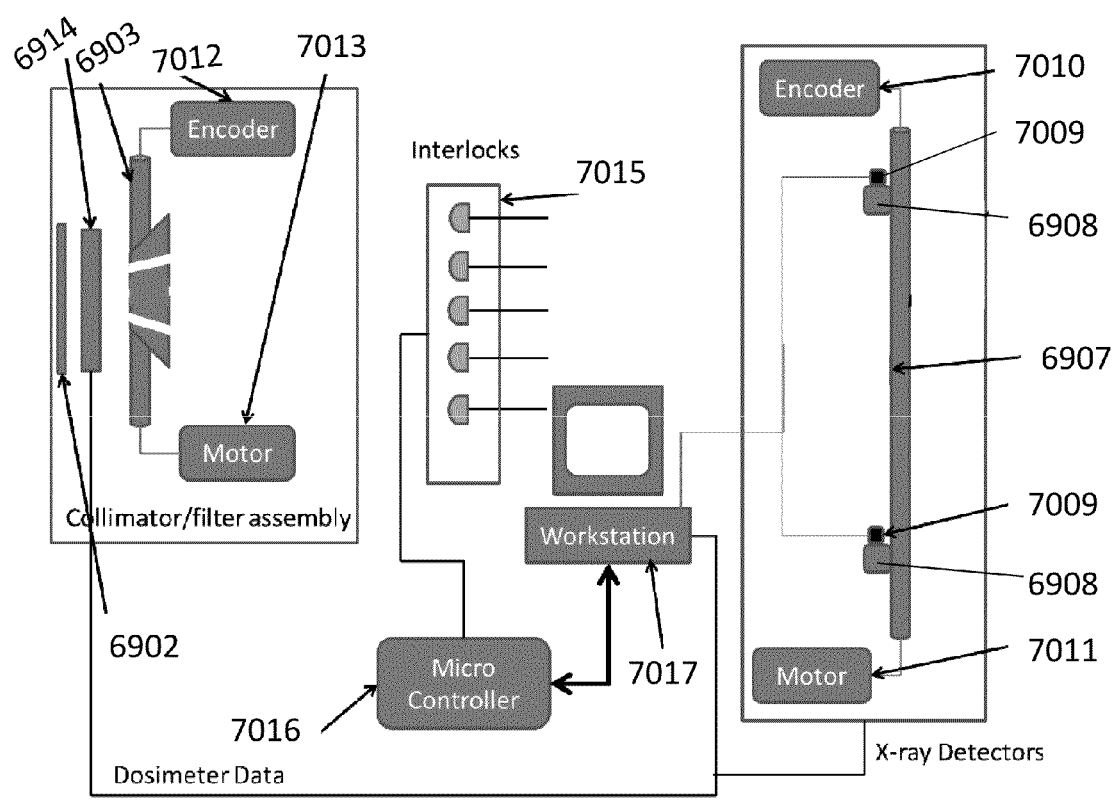
FIG. 70 is a schematic and block circuit diagram of an exemplary embodiment of an image acquisition system and microprocessor controller according to the invention, which systems interact with each other to control production of x-rays and formation of an image, with the x-ray generator not illustrated.

FIGS. 69 to 72 illustrate scanning systems and methods that can be used to provide medical applications. Referring to FIG. 69 and FIG. 70, in accordance with an exemplary embodiment of the present invention, an x-ray source 6901 is a x-ray tube capable of producing a fan beam of x-rays with a maximum energy of at least 150 keV. The x-ray tube 6901 is capable of producing a fan beam of x-rays with a cone angle of at least 69 degrees in the longitudinal axis of the scan and 30 degrees in the transverse axis of the scan. The x-ray tube is connected to an x-ray generator mounted in a lead-lined cabinet with high voltage cables not shown in the drawing. A filter wheel 6902 containing one or more filters made of aluminum and copper of varying thicknesses (Al 1-2 mm, Cu 0.1-0.2 mm) is placed in close proximity (within a few centimeters) to the output of the generator to intercept and filter the x-ray beam. A collimator 6903 containing a plurality of horizontal slits is placed adjacent the filter 6902 to intercept and collimate the filtered x-ray beam into a plurality of horizontal beams of x-rays such that the height of the x-ray beams are the same dimension as the detector arrays 6908. In an exemplary embodiment, CCD TDI arrays are utilized. In another exemplary embodiment, the CCD-TDI array are substituted with a photodiode-CMOS integrated circuit TDI camara array or any similar technology.

The detector arrays 6908 are comprised of one or more TDI sensors. The collimator 6903 is moved up and down by a motor 7013 that is controlled by a microprocessor controller 7016. The microprocessor controller 7016 receives data from an encoder 7012 mounted on the collimator assembly that provides data on a position and speed of the collimator 6903. X-rays emitted by the collimator 6903 pass through an aperture 6904 that confines the dimension and movement of the x-ray beams 6905 within the active area defined by the detector arrays 6908 that are moved along the horizontal supports 6907 by a slide drive motor 7011. The position and speed of the arrays is monitored by an encoder 7010 that sends data to the microprocessor controller 7016. The aperture 6904 can be simply an outwardly expanding frusto-conical opening that creates a rectangular (or square) region of exposure for the entire body of the entity being scanned. However, when radiographic images are required of a specific anatomical region, such as a chest, the abdomen, or an extremity, in an alternative embodiment of the aperture, a second collimator can restrict, in an adjustable manner, the shape, size, and location of the region of the entity being exposed without having to move the entity. Collimators used in such radiographic systems typically have two sets of adjustable lead shutters that can be moved by the operator to control the size and location of the anatomical region of the patient. The collimator adjustment is facilitated by a light field produced within the collimator that, when controlled by the collimator shutters, produces a light field on the patient that is identical to the x-ray exposure area. With a collimator having the adjustable shutters and light field, the operator can restrict the lateral and transverse extent of the exposure. In this way, various anatomical regions can be isolated and scanned to produce radiographic images of only those regions.

In an exemplary embodiment of the present invention using the CCD technology, there are a total of 128 CCD TDI image sensors in each array and a total of 2 individual linear arrays. The length of the individual detector arrays 6908 is approximately 27 inches but they can be shorter or longer depending on the particular application. Each of these linear arrays 6908 is illuminated by the collimated x-ray beams 6905 emitted by the x-ray source 6901. When the amount of x-rays is absorbed in the detector arrays 6908 to produce an adequate exposure, in the CCD TDI array example, the charge accumulated in one row of CCDs is shifted to the next row. Because there are two detector arrays in this embodiment, two segments of the output x-ray image are formed. The slide motor drive 7011 for the CCD TDI array then indexes the size of a CCD pixel (0.05 mm) and rests while each line of CCD sensors acquire another exposure. This process is repeated until the entire length of the image size has been scanned. The slide motor 7011 moves each of the CCD TDI arrays a total distance of approximately 990 mm (39 inches) creating two simultaneous image segments that are approximately 690 mm (27 inches) wide by approximately 990 mm (39 inches) tall. The two image segments are stitched together by the image processing program in the workstation 7017 to produce a composite image that is 2 meters tall (78 inches) by 0.69 meters wide (27 inches).

In accordance with an exemplary embodiment of the present invention, the CCD TDI arrays 6908 are manufactured by Hamamatsu Photonics (Hamamatsu City, Japan) part no. S7199-01. These CCD TDI arrays contain a matrix of 1,536×128 pixels that are 48×48 microns. A fiber optic face plate is cemented to the surface of the CCD array with optical cement and a scintillating phosphor is deposited on the top of the fiber optic plate. A total of 9 CCD TDI image sensors are butted together to form a detector array that is approximately 27 inches long.

The technique factors (filtration, kV, mA, and exposure time) used to expose the entity, e.g., a person, being scanned are optimized by a software program installed on the workstation 7017 or microcontroller 7016. This software program monitors the exposure level of the detector arrays 6908 and other data from the microprocessor controller 7016 while the x-ray beams 6905 are exposing them to adjust the technique factors produced by the x-ray generator 6901 such that the intensity and contrast of the x-ray image is maximized while the exposure dose is minimized for each person being scanned. This program is similar in nature to the programs and devices used by medical diagnostic x-ray equipment for fluoroscopic imaging to dynamically control exposure and image quality commonly known as Automatic Brightness Systems (ABS). Each of the two detector arrays 6908 acquires images of separate anatomical regions. The lower array images the lower extremities (groin, legs, and feet) and the upper array images the abdominal, chest, and skull regions. The collimator 6903 has separate openings, one for each of the two arrays in this example. Because each collimator opening views a specific anatomical region, a different filter element is used for each opening to optimize x-ray beam quality for each region separately.

In accordance with an exemplary embodiment of a method of the present invention, the ABS system operates by taking the digital output value from each TDI pixel after exposure and defining a region of anatomical exposure (those detector arrays 6908 not exposed directly to the x-ray source) and averaging those values into a single value. This single average value is then compared to a target value that is equal to one half of the saturated value (from an exposure just large enough to saturate the photodiode) of the photodiode. If the average value is lower than the target value, then the x-ray intensity (mA) is increased or the kV of the x-ray spectrum is increased to drive the average value to the target value during the next line of exposure. Conversely, if the average value is higher than the target value, then the kV and mA values are lowered. The kV and mA values are changed according to a pre-determined relationship or look-up table (LUT) that is created and optimized by experimentation with the image quality produced at various x-ray technique (kV and mA) values using anatomically correct phantoms.

In an alternative embodiment, individual photodiodes 7009 (one or more) are mounted on each of the individual detector arrays 6908. These individual photodiodes 7009 are exposed and produce the digital output value used to compare with the target value. Accordingly, the shape of the collimator openings has notches in them to permit x-rays to pass through to expose these individual photodiodes 7009.

Figure 71:
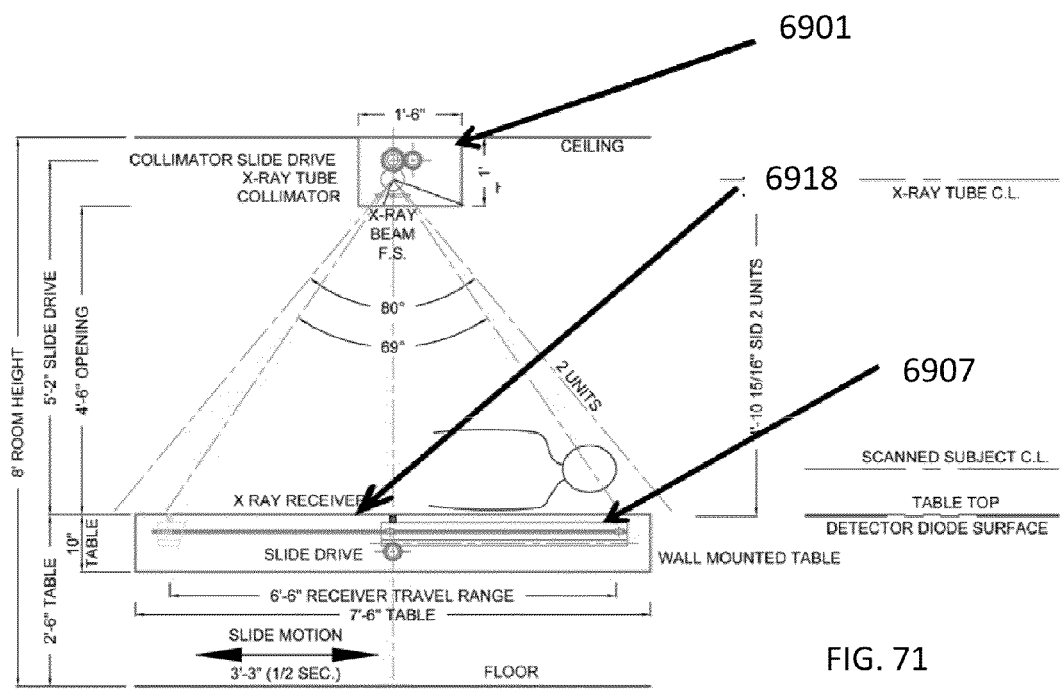
FIG. 71 is a scale drawing showing a side elevational view of an exemplary embodiment of an x-ray scanner according to the invention with the computer workstation not illustrated.
Figure 72:
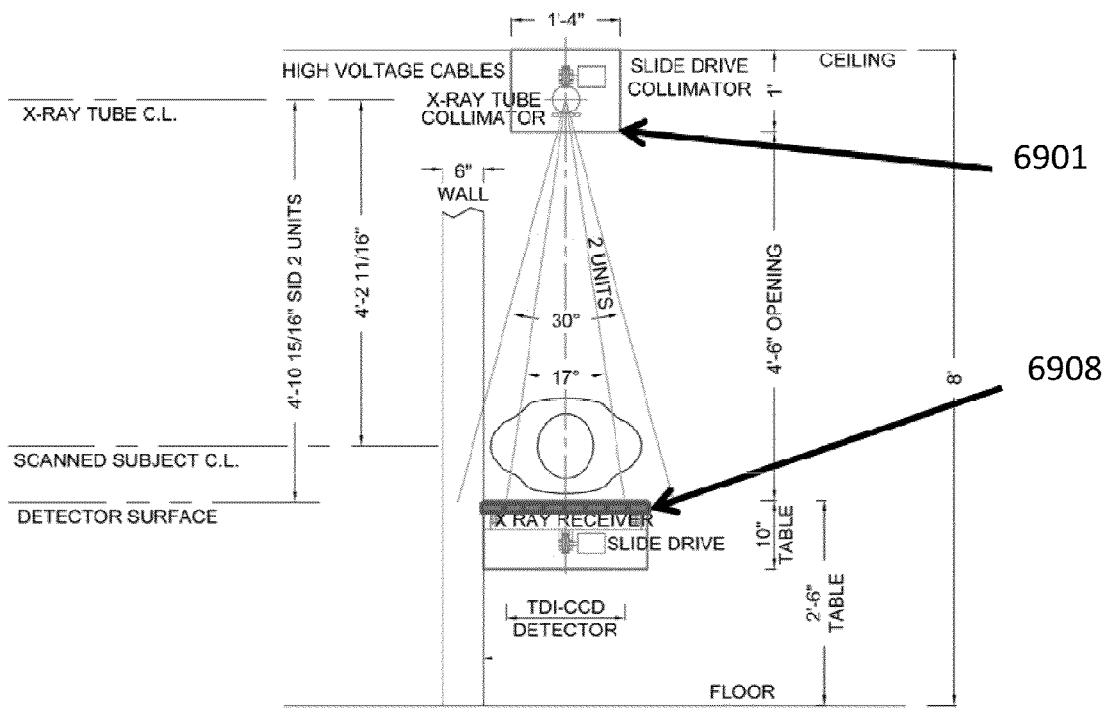
FIG. 72 is a scale drawing showing a side elevational view of an exemplary embodiment of an x-ray scanner according to the invention with the computer workstation not illustrated.

A method for operating the x-ray scanner according to an exemplary embodiment of the present invention begins when the operator initializes the scanner from the GUI on the workstation 7017, for example, in FIGS. 71 and 72. The patient to be scanned (whether ambulatory, unconscious, or unable to move without assistance) is placed on the table 6918. When the patient is properly positioned, an image is acquired of the entire body by energizing the x-ray source 6901 and moving the collimators 6903 and detector arrays 6908.

In alternative embodiment of the present invention, the x-ray source 6901 is mounted horizontally and the x-ray table 6918 is mounted vertically so that images can be acquired from standing patients. In this embodiment, radiographs such as chest, abdominal, and extremity images can be acquired along with images used in orthopedic applications such as scoliosis and long-bone studies from standing patients. This system, in either the horizontal or vertical orientation, can serve as a whole-body trauma radiographic system and provide a full range of radiographic capabilities including specialty orthopedic studies in one room. In yet another embodiment of the present invention, the x-ray source 6901 can pivot to acquire images vertically or horizontally and there are two x-ray tables 6918, one mounted vertically and one mounted horizontally to provide, in a single radiographic room, the capability to acquire substantially all of the standard radiographic imaging exams performed in a hospital or clinic.

The image produced by the scanner can be read by a radiologist to determine the extent and severity of various injuries or trauma sustained by the patient. The images can be saved on a hard drive of the workstation 7017 for later review and can be sent to a PACS archive or viewing station. The dose used to acquire each image is also stored as well.

Safe operation of the scanner is ensured by the use of several interlocks 7015 that are connected to the table 6918, the x-ray generator 6901, the detector array 6908, and other components to ensure that x-rays are not emitted unless the interlocks are satisfied and that x-rays are properly lined up with the operation of the detector arrays 6908. The interlocks 7015 are managed by the microprocessor controller 7016.

The foregoing description and accompanying drawings illustrate the principles, exemplary embodiments, and modes of operation of the invention. However, the invention should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An x-ray scanner, comprising:
    an x-ray source operable to produce a fan beam of x-rays and to move about a source movement axis;
    at least one x-ray detector array:
        having a detector dimension;
        having a plurality of time delay and integration (TDI) detector arrays each having a height dimension; and
        being operable to detect x-rays from the x-ray source along the detector dimension;
    at least one collimator disposed between the x-ray source and the at least one x-ray detector array, fixed to the x-ray source, and defining a plurality of lateral slits to collimate the fan beam of x-rays into a plurality of lateral beams such that the lateral beams have a height dimension that is the same as the height dimension of the TDI detector arrays;
    a first motor operable to move the at least one collimator;
    a second motor operable to move the TDI detector arrays;
    an x-ray processing unit operable:
        to control the first and second motors;
        to process detection of the x-rays by the at least one x-ray detector array; and
        to form an x-ray scanned image of an entity disposed between the at least one collimator and the at least one x-ray detector array such that an intensity and contrast of the x-ray scanned image is maximized while an exposure dose for the entity is minimized.

2. The x-ray scanner according to claim 1, wherein the plurality of TDI detector arrays are a plurality of charge-coupled device (CCD) TDI detector arrays.

3. The x-ray scanner according to claim 1, wherein the plurality of TDI detector arrays are a plurality of photodiode-CMOS integrated circuit TDI camara arrays.

4. The x-ray scanner according to claim 1, wherein the x-ray source comprises an x-ray tube configured to produce the fan beam of x-rays with a maximum energy of at least 150 keV.

5. The x-ray scanner according to claim 4, wherein the x-ray tube is configured to produce the fan beam of x-rays with a cone angle of at least 69 degrees in a longitudinal axis and 30 degrees in a transverse axis.

6. The x-ray scanner according to claim 1, wherein the at least one collimator is two collimator elements, a first of the collimator elements defining the plurality of lateral slits to collimate the fan beam of x-rays into the plurality of lateral beams such that the lateral beams have a height dimension that is the same as the height dimension of the TDI detector arrays and a second of the collimator elements defining an extent of an area to be exposed.

7. The x-ray scanner according to claim 4, wherein:
    the plurality of TDI detector arrays are a plurality of charge-coupled device (CCD) TDI detector arrays; and
    the at least one x-ray detector array has 128 CCD TDI image sensors and 2 individual linear arrays.

8. The x-ray scanner according to claim 7, wherein each of the linear arrays is illuminated by at least one of the lateral beams.

9. The x-ray scanner according to claim 2, wherein the at least one x-ray detector array has 9 CCD TDI image sensors.

10. The x-ray scanner according to claim 1, wherein the x-ray processing unit is operable to apply technique factors that are used to expose the entity being scanned, and further comprising a microcontroller operably associated with the x-ray processing unit and operable to optimize the technique factors.

11. The x-ray scanner according to claim 10, wherein the technique factors comprise filtration, kV, mA, and exposure time.

12. The x-ray scanner according to claim 10, wherein the microcontroller is operable to monitor an exposure level of the CCD TDI arrays.

13. The x-ray scanner according to claim 1, further comprising a filter wheel having at least one filter, the filter wheel being placed between the x-ray source and the at least one collimator.

14. The x-ray scanner according to claim 13, wherein the plurality of TDI detector arrays operable to acquire images of separate anatomical regions of the entity.

15. The x-ray scanner according to claim 14, wherein the at least one x-ray detector array comprises a lower array operable to image a lower extremities region of the entity and an upper array operable to image abdominal, chest, and skull regions of the entity.

16. The x-ray scanner according to claim 15, wherein the at least one collimator has separate openings corresponding to each of the plurality of TDI detector arrays.

17. The x-ray scanner according to claim 16, wherein the at least one filter is a plurality of different filters and one of the different filters is used for each opening to optimize x-ray beam quality separately for each of the lower extremities region and the abdominal, chest, and skull regions.

18. A radiographic imaging system, comprising:
a horizontally disposed radiographic table having:
at least one horizontal x-ray detector array:
having a first detector dimension;
having a plurality of time delay and integration (TDI) detector arrays each having a height dimension; and
being operable to detect x-rays from an x-ray source along the first detector dimension;
a first motor operable to move the at least one horizontal x-ray detector array in a horizontal direction;
a vertically disposed radiographic table adjacent the horizontally disposed radiographic table, the vertically disposed radiographic table having:
at least one vertical x-ray detector array:
having a second detector dimension;
having a plurality of TDI detector arrays each having the height dimension; and
being operable to detect x-rays from an x-ray source along the second detector dimension;
a second motor operable to move the at least one vertical x-ray detector array in a vertical direction;
an x-ray scanner pivotable between a vertical scanning orientation in which the x-ray scanner is directed at the vertically disposed radiographic table and a horizontal scanning orientation in which the x-ray scanner is directed at the horizontally disposed radiographic table, the x-ray scanner having;
an x-ray source operable to produce a fan beam of x-rays and to move about a source movement axis;
at least one collimator:
fixed to the x-ray source and disposed between the x-ray source and the at least one horizontal x-ray detector array in the horizontal scanning orientation and between the x-ray source and the at least one vertical x-ray detector array in the vertical scanning orientation; and
defining a plurality of horizontal slits to collimate the fan beam of x-rays into a plurality of lateral beams such that the lateral beams have a height dimension that is the same as the height dimension of the TDI detector arrays; and
a third motor operable to move the at least one collimator;
an x-ray processing unit operably connected to both the horizontally and vertically disposed radiographic tables and operable:
to control the first, second, and third motors;
to process detection of the x-rays by the at least one vertical x-ray detector array and the at least one horizontal x-ray detector array; and
to form an x-ray scanned image of an entity disposed between the at least one collimator and one of the at least one vertical x-ray detector array and the at least one horizontal x-ray detector array such that an intensity and contrast of the x-ray scanned image is maximized while an exposure dose for the entity is minimized; and
the horizontally disposed radiographic table, the vertically disposed radiographic table, the x-ray scanner, and the x-ray processing unit are all sized to fit within a single radiographic room.

\* \* \* \* \*